US006719979B2

(12) United States Patent
Peeters et al.

(10) Patent No.: US 6,719,979 B2
(45) Date of Patent: Apr. 13, 2004

(54) NEWCASTLE DISEASE VIRUS INFECTIOUS CLONES, VACCINES AND DIAGNOSTIC ASSAYS

(75) Inventors: Bernardus Petrus Hubertus Peeters, Lelystad (NL); Olav Sven de Leeuw, Almere (NL); Arnoud Leonard Josef Gielkens, Lelystad (NL)

(73) Assignee: ID-Lelystad, Instituut voor Dierhouderij en Diergezondheid B.V., Lelystad (NL)

( * ) Notice: Subject to any disclaimer, the term of this patent is extended or adjusted under 35 U.S.C. 154(b) by 0 days.

(21) Appl. No.: 09/741,744

(22) Filed: Dec. 19, 2000

(65) Prior Publication Data

US 2003/0087417 A1 May 8, 2003

Related U.S. Application Data

(63) Continuation of application No. PCT/NL99/00377, filed on Jun. 7, 1999.

(30) Foreign Application Priority Data

Jun. 19, 1998 (EP) .............................................. 98202054

(51) Int. Cl.$^7$ ...................... A61K 39/12; A61K 39/295; C12P 21/04; C12H 7/01; C07H 21/04
(52) U.S. Cl. ................................ 424/214.1; 424/186.1; 424/199.1; 424/202.1; 424/204.1; 435/235.1; 435/70.1; 536/23.1; 536/23.72
(58) Field of Search .......................... 435/235.1, 172.3, 435/70.1, 205.1, 211.1, 212.1, 224.1, 236, 235, 172.1; 424/186.1, 199.1, 202.1, 204.1, 214.1; 536/23.1, 23.72

(56) References Cited

U.S. PATENT DOCUMENTS 6,033,886 A  *  3/2000  Conzelmann ............ 435/172.3
6,146,642 A     11/2000 Garcia-Sastre et al.

OTHER PUBLICATIONS

Philips et al. Archives of Virology. Oct., 1998; 143 (10): 1993–2002.*
sequence alignment of SEQ ID No: 82 with GenEmbl database accession No. AJ225128 of Phillips et al. submitted to database Dec. 11, 1998.*
Kurilla et al. (Virology. 1985; 145: 203–212) teach SEQ ID NO: 80 (see the sequence alignment provided from the GenEmbl database accession No.*
sequence alignment of SEQ ID NO: 80 with GenEmbl database accession No. U25283 of Kurilla et al. submitted to database Aug, 2, 1993.*
Pokric et al. Vaccine. 1993; 11(6): 655–659.*
Fields et al. Virology, 3rd edition. 1995. vol. 1. Philadelphia: Lippencott Williams and Wilkins, pp. 1181, 1187.*
Vindevogel et al., "Panzootic Newcastle Disease Virus in Pigeons", undated, pp. 184–196.
Spradbrow, P. B., "Geographical Distribution", undated, pp. 247–255.
Rott et al., "Molecular Basis of Infectivity and Pathogenicity of Newcastle Disease Virus", undated, pp. 98–113.
Peeples, Mark E., "Newcastle Disease Virus Replication", undated, pp. 45–79.
Kaleta et al., "Newcastle Disease in Free–Living and Pet Birds", undated, pp. 197–245.
Hanson, Robert P., "Heterogeneity within Strains of Newcastle Disease Virus: Key to Survival", undated, pp. 113–131.
Doyle, T. M., "A Hitherto Unrecorded Disease of Fowls Due to a Filter–Passing Virus", undated, pp. 144–169.
Beaudette et al., Newcastle Disease Immunization with Live Virus, undated, pp. 302–334.
Beard et al., "Newcastle Disease", undated, Chapter 19, pp. 452–470.
Alexander, D. J., "Paramyxovirus Infection", *Virus Infections of birds*, undated, Chapter 22, pp. 321–340.
Hitchner et al., "A Virus of Low Virulence for Immunizing Fowls against Newcastle Disease", Dec. 1948, pp. 525–530.
Hofstad, M. S., "Immunization of Chickens Against Newcastle Disease by Fomalin–Inactivated Vaccine", Oct. 1953, pp. 586–589.
Heuschele et al., "Local Immunity and Persistence of Virus in the Tracheas of Chickens Following Infection with Newcastle Disease Virus", May 1970, vol. 121, No. 5, pp. 497–504.
Smith et al., "Isolation and Assay of Rabies Serogroup Viruses in CER Cells", 1977, *Intervirology*, vol. 8, pp. 92–99.
Moscovici, Carlo, "Continuous Tissue Culture Cell Lines Derived from Chemically Induced Tumors of Japanese Quail", May 1977, *Cell*, vol. 11, pp. 95–103.
Madansky et al., "Noncytopathis Mutants of Newcastle Disease Virus", Jun. 1978, vol. 26, No. 3, pp. 724–729.
Chang et al., "Construction and Characterization of Amplifiable Multicopy DNA Cloning Vehicles Derived from the P15A Cryptic Miniplasmid", Jun. 1978, vol. 134, No. 3, pp. 1141–1156.

(List continued on next page.)

*Primary Examiner*—James Housel
*Assistant Examiner*—Shanon Foley
(74) *Attorney, Agent, or Firm*—TraskBritt

(57) ABSTRACT

The invention relates to the process for generating infectious Newcastle disease virus (NDV) entirely from cloned full-length cDNA and to the use of vaccines and diagnostic assays generated with and derived from the process. The process offers the possibility to modify the NDV genome by means of genetic modification and allows the introduction of mutations, deletions and/or insertions. The process can be used to modify the antigenic makeup of NDV, thus allowing the generation of live NDV marker vaccines which can be serologically distinguished from NDV field strains.

42 Claims, 25 Drawing Sheets

OTHER PUBLICATIONS

Goldhaft, Tevis M., "Guest Editorial Historical Note on the Origin of the LaSota Strain of Newcastle Disease Virus", Oct. 1, 1979, *Avian Diseases*, vol. 24, No. 2, pp. 297–301.

Garten et al., "Mutational Changes of the Protease Susceptibility of Glycoprotein F of Newcastle Disease Virus: Effects of Pathogenicity", 1980, *J. gen. Virol.*, vol. 50, pp. 135–147.

Madansky et al., "Noncytopathic Mutants of Newcastle Disease Virus Are Defective in Virus–Specific RNA Synthesis", Jan. 1981, *Journal of Virology*, vol. 31, No. 1, pp. 317–327.

Madansky et al., "Relationship Among Virus Spread, Cytopathogenicity, and Virulence as Revealed by the Noncytopathic Mutants of Newcastle Disease Virus", Dec. 1981, *Journal of Virology*, vol. 40, No. 3, pp. 691–702.

Cho, B. R., "Cytopathic Effects and Focus Formation by Reticuloendotheliosis Viruses in a Quail Fibroblast Cell Line", Aug. 25, 1982, *Avian Diseases*, vol. 27, No. 1, pp. 261–270.

Russell et al., "The Characterization of Monoclonal Antibodies to Newcastle Disease Virus", 1983, *J. gen. Virol.*, vol. 64, pp. 2069–2072.

Wensvoort et al., "Production of Monoclonal Antibodies Against Swine Fever Virus and their use in Laboratory Diagnosis", Nov. 14, 1986, *Veterinary Microbiology*, vol. 12, pp. 101–108.

Chambers et al., "Molecular Cloning of Complementary DNA to Newcastle Disease Virus, and Nucleotide Sequence Analysis of the Junction between the Genes encoding the Haemagglutinin–Neuraminidase and the Large Protein", 1986, vol. 67, pp. 475–486.

Long et al., "Monoclonal Antibodies to Hemagglutin-–Neuraminidase and Fusion Glycoproteins of Newcastle Disease Virus: Relationship between Glycosylation and Reactivity", Mar. 1986, *Journal of Virology*, pp. 1198–1202.

Tessier et al., "Ligation of Single–Stranded Oligodeoxyribonucleotides by T4 RNA Ligase", 1986, vol. 158, *Analytical Biochemistry*, pp. 171–177.

Meulemans et al., "Protective Effects of HN and F Glycoprotein–specific Monoclonal Antibodies on Experimental Newcastle Disease", 1986, *Avian Pathology*, vol. 15, pp. 761–768.

Ishida et al., "Sequence of 2,617 nucleotides from the 3' end of Newcastle disease virus genome RNA and the predicted amino acid sequence of viral NP protein", 1986, *Nucleic Acids Research*, vol. 14, No. 16, no pertinent pages listed.

Yusoff et al., "Nucleoside sequence analysis of the L gene of Newcastle disease virus: homologies with Sendai and vesicular stomatitis viruses", Apr. 23, 1987, pp. 2961–3976.

Cowen et al., "The Propagation of Avian Viruses in a Continuous Cell Line (QT35) of Japanese Quail Origin", 1988, *Avian Diseases*, vol. 32, pp. 282–297.

Millar et al., "Nucleotide Sequence of the Fusion and Haemagglutinin–Neuraminidase Glycoprotein Genes of Newcastle Disease Virus, Strain Ulster: Molecular Basis for Variations in Pathogenicity between Strains", 1988, *J. gen. Virol.*, vol. 69, pp. 613–620.

Boursnell et al., "A Recombinant Fowlpox Virus Expressing the Hemagglutinin–Neuramindase Gene of Newcastle Disease Virus (NDV) Protects Chickens against Challenge by NDV", 1990, *Virology*, vol. 178, pp. 297–300.

Taylor et al., "Newcastle Disease Virus Fusion Protein Expressed in a Fowlpox Virus Recombinant Confers Protection in Chickens", Apr. 1990, *Journal of Virology*, pp. 1441–1450.

Vieira et al., "New pUC–derived cloning vectors with different selectable markers and DNA replication origins", 1991, *Gene*, vol. 100, pp. 189–194.

Antin et al., "Isolation and Characterization of an Avian Myogenic Cell Line", 1991, *Developmental Biology*, vol. 143, pp. 111–121.

Peeters et al., "Pseudorabies Virus Envelope Glycoproteins gp50 and gII Are Essential for Virus Penetration, but Only gII Is Involved in Membrane Fusion", Feb. 1992, *Journal of Virology*, pp. 894–905.

Pattnaik et al., "Infectious Defective Interfering Particles of VSV from Transcripts of a cDNA Clone", Jun. 12, 1992, *Cell*, vol. 69, pp. 1011–1020.

Morgan et al., "Protection of Chickens from Newcastle and Marek's Diseases with a Recombinant Herpervirus of Turkeys Vaccine Expressing the Newcastle Disease Virus Fusion Protein", 1992, *Avian Diseases*, vol. 36, pp. 858–870.

Burke Jr., A. A., "Application of an electrochemical arsine generator on a high throughout MOVPE reactor", 1992, *Journal of Crystal Growth*, vol. 124, pp. 292–299.

Ichihara et al., "Construction of new T Vectors for direct cloning of PCR products", 1993, *Gene*, vol. 130, pp. 153–154.

Steward et al., "RNA editing in Newcastle disease virus", 1993, *Journal of General Virology*, vol. 74, pp. 2539–2547.

Morgan et al., "Efficacy in Chickens of a Herpesvirus of Turkeys Recombinant Vaccine Containing the Fusion Gene of Newcastle Disease Virus: Onset of Protection and Effect of Maternal Antibodies", 1993, *Avian Diseases*, vol. 37, pp. 1032–1040.

Calain et al., "The Rule of Six, a Basic Feature for Efficient Replication of Sendai Virus Defective Interfering RNA", Aug. 1993, *Journal of Virology*, vol. 67, No. 8, pp. 4822–4830.

Schnell et al., "Infectious rabies viruses from cloned cDNA", 1994, *The EMBO Journal*, vol. 13, No. 18, pp. 4195–4203.

Whelen et al., "Efficient recovery of infectious vesicular stomatitis virus entirely from cDNA clones", Aug. 1995, *Proc. Natl. Acad. Sci. USA*, vol. 92, 99.8388–8392.

Stäuber et al., "Detection of Newcastle disease virus in poultry vaccines using the polymerase chain reaction and direct sequencing of amplified cDNA", 1995, *Vaccine*, vol. 13, No. 4, pp. 360–364.

Schütze et al., "Complete genomic sequence of the fish rhabdovirus infectious haematopeietic necrosis virus", 1995, *Journal of General Virology*, vol. 76, pp. 2519–2527.

Radecke et al., "Rescue of measles viruses from cloned DNA", 1995, *The EMBO Journal*, vol. 14, No. 23, pp. 5773–5784.

Lawson et al., "Recombinant vesicular atomatitis viruses from DNA", May 1995, *Proc. Natl. Acad. Sci. USA*, vol. 92, pp. 4477–4481.

Harty et al., "Mutations within Noncoding Terminal Sequences of Model RNAs of Sendai Virus: Influence on Reporter Gene Expression", Aug. 1995, *Journal of Virology*, pp. 5128–5131.

Garcin et al., "A highly recombinogenic system for the recovery of infectious Sendai paramyxovirus from cDNA: generation of a novel copy–back nondefective interfering virus", 1995, *The EMBO Journal*, vol. 14, No. 24, pp. 6087–6094.

Deng et al., "Localization of a Domain on the Paramyxovirus Attachment Protein Required for the Promotion of Cellular Fusion by Its Homologous Fusion Protein Spike", 1995, *Biology*, vol. 209, pp. 457–469.

Collins et al., "Production of infections human respiratory virus from cloned cDNA confirms an essential role for the transcription elongation factor from the 5' proximal open reading frame of the M2 mRNA in gene expression and provides a capability for vaccine development", Dec. 1995, *Proc. Natl. Acad. Sci. USA*, vol. 92, pp. 11563–11567.

Conzelman, Karl–Klaus, "Genetic manipulation of non–segmented negative–strand RNA viruses", 1996, *Journal of General Virology*, vol. 77, pp. 381–389.

Stäuber et al., "Detection of Newcastle disease virus in poultry vaccines using the polymerase chain reaction and direct sequencing of amplified cDNA", 1995, *Vaccine*, vol. 13, No. 4, pp. 360–364.

Heckert et al., "Onset of Protective Immunity in Chicks after Vaccination with a Recombinant Herpesvirus of Turkeys Vaccine Expressing Newcastle Disease Virus Fusion and Hemagglutinin–Neuraminidase Antigens", 1996, *Avian Diseases*, vol. 40, pp. 770–777.

Britton et al., "Expression of bacteriophage T7 RNA polymerase in avian and mammalian cells by a recombinant fowlpox virus", 1996, *Journal of General Virology*, vol. 77, pp. 963–967.

Schneider et al., "Rescue of measles virus using a replication–deficient vaccinia–T7 vector", 1997, *Journal of Virological Methods*, vol. 64, pp. 57–64.

Lamb et al., "Paramyxoviridae: The Viruses and Their Replication", 1996, *Fundamental Virology, Third Edition*, Chapter 20, pp. 577–604.

Kant et al., "Differentiation of virulent and non–virulent strains of Newcastle disease virus within 24 hours by polymerase chain reaction", 1997, *Avian Pathology*, vol. 26, pp. 837–849.

Hoffman et al., "An infectious Clone of Human Parainfluence Virus Type 3", Jun. 1997, *Journal of Virology*, pp. 4272–4277.

Baron et al., "Rescue of Rinderpest Virus from Cloned cDNA", Feb. 1997, *Journal of Virology*, pp. 1265–1271.

Schirrmacher et al., "Immunization With Virus–Modified Tumor Cells", Dec. 1998, *Seminars in Oncology*, vol. 25, No. 6, pp. 677–696.

Kolakofsky et al., "Paramyxovirus RNA Synthesis and the Requirement for Hexamer Genome Length: the Rule of Six Revisited", Feb. 1998, *Journal of Virology*, pp. 891–899.

Leeuw et al., "Complete nucleotide sequence of Newcastle disease virus: evidence for the existence of a new genus within the subfamily Paramyxovirinae", 1999, *Journal of General Virology*, vol. 80, pp. 131–136.

Peeters et al., "Rescue of Newcastle Disease Virus from Cloned cDNA: Evidence that Cleavability of the Fusion Protein Is a Major Determinant for Virulence", Jun. 1999, *Journal of Virology*, pp. 5001–5009.

Oberdörfer et al., "Generation of recombinant ientogenic Newcastle disease virus from cDNA", 1999, *Journal of General Virology*, vol. 80, pp. 2987–2995.

\* cited by examiner

Fig. 3 Nucleotide sequence of NDV strain LaSota

```
  1 accaaacagagaatccgtgagttacgataaaaggcgaaggagcaattgaagtcgcacgggtagaaggtgtgaatctcgag  80

81 tgcgagcccgaagcacaaactcgagaaagccttctgccaac ATG TCT TCC GTA TTT GAT GAG TAC GAA    148
  1                                            M   S   S   V   F   D   E   Y   E      9

149 CAG CTC CTC GCG GCT CAG ACT CGC CCC AAT GGA GCT CAT GGA GGG GGA GAA AAA GGG AGT   208
 10  Q   L   L   A   A   Q   T   R   P   N   G   A   H   G   G   G   E   K   G   S    29

209 ACC TTA AAA GTA GAC GTC CCG GTA TTC ACT CTT AAC AGT GAT GAC CCA GAA GAT AGA TGG   268
 30  T   L   K   V   D   V   P   V   F   T   L   N   S   D   D   P   E   D   R   W    49

269 AGC TTT GTG GTA TTC TGC CTC CGG ATT GCT GTT AGC GAA GAT GCC AAC AAA CCA CTC AGG   328
 50  S   F   V   V   F   C   L   R   I   A   V   S   E   D   A   N   K   P   L   R    69

329 CAA GGT GCT CTC ATA TCT CTT TTA TGC TCC CAC TCA CAG GTA ATG AGG AAC CAT GTT GCC   388
 70  Q   G   A   L   I   S   L   L   C   S   H   S   Q   V   M   R   N   H   V   A    89

389 ATT GCA GGG AAA CAG AAT GAA GCC ACA TTG GCC GTG CTT GAG ATT GAT GGC TTT GCC AAC   448
 90  I   A   G   K   Q   N   E   A   T   L   A   V   L   E   I   D   G   F   A   N   109

449 GGC ACG CCC CAG TTC AAC AAT AGG AGT GGA GTG TCT GAA GAG AGA GCA CAG AGA TTT GCG   508
110  G   T   P   Q   F   N   N   R   S   G   V   S   E   E   R   A   Q   R   F   A   129

509 ATG ATA GCA GGA TCT CTC CCT CGG GCA TGC AGC AAC GGA ACC CCG TTC GTC ACA GCC GGG   568
130  M   I   A   G   S   L   P   R   A   C   S   N   G   T   P   F   V   T   A   G   149

569 GCA GAA GAT GAT GCA CCA GAA GAC ATC ACC GAT ACC CTG GAG AGG ATC CTC TCT ATC CAG   628
150  A   E   D   D   A   P   E   D   I   T   D   T   L   E   R   I   L   S   I   Q   169

629 GCT CAA GTA TGG GTC ACA GTA GCA AAA GCC ATG ACT GCG TAT GAG ACT GCA GAT GAG TCG   688
170  A   Q   V   W   V   T   V   A   K   A   M   T   A   Y   E   T   A   D   E   S   189

689 GAA ACA AGG CGA ATC AAT AAG TAT ATG CAG CAA GGC AGG GTC CAA AAG AAA TAC ATC CTC   748
190  E   T   R   R   I   N   K   Y   M   Q   Q   G   R   V   Q   K   K   Y   I   L   209

749 TAC CCC GTA TGC AGG AGC ACA ATC CAA CTC ACG ATC AGA CAG TCT CTT GCA GTC CGC ATC   808
210  Y   P   V   C   R   S   T   I   Q   L   T   I   R   Q   S   L   A   V   R   I   229

809 TTT TTG GTT AGC GAG CTC AAG AGA GGC CGC AAC ACG GCA GGT GGT ACC TCT ACT TAT TAT   868
230  F   L   V   S   E   L   K   R   G   R   N   T   A   G   G   T   S   T   Y   Y   249

869 AAC CTG GTA GGG GAC GTA GAC TCA TAC ATC AGG AAT ACC GGG CTT ACT GCA TTC TTC TTG   928
250  N   L   V   G   D   V   D   S   Y   I   R   N   T   G   L   T   A   F   F   L   269

929 ACA CTC AAG TAC GGA ATC AAC ACC AAG ACA TCA GCC CTT GCA CTT AGT AGC CTC TCA GGC   988
270  T   L   K   Y   G   I   N   T   K   T   S   A   L   A   L   S   S   L   S   G   289

989 GAC ATC CAG AAG ATG AAG CAG CTC ATG CGT TTG TAT CGG ATG AAA GGA GAT AAT GCG CCG  1048
290  D   I   Q   K   M   K   Q   L   M   R   L   Y   R   M   K   G   D   N   A   P   309

1049 TAC ATG ACA TTA CTT GGT GAT AGT GAC CAG ATG AGC TTT GCG CCT GCC GAG TAT GCA CAA 1108
310  Y   M   T   L   L   G   D   S   D   Q   M   S   F   A   P   A   E   Y   A   Q   329
```

Fig. 3 continued

```
1109 CTT TAC TCC TTT GCC ATG GGT ATG GCA TCA GTC CTA GAT AAA GGT ACT GGG AAA TAC CAA 1168
330  L   Y   S   F   A   M   G   M   A   S   V   L   D   K   G   T   G   K   Y   Q   349

1169 TTT GCC AGG GAC TTT ATG AGC ACA TCA TTC TGG AGA CTT GGA GTA GAG TAC GCT CAG GCT 1228
350  F   A   R   D   F   M   S   T   S   F   W   R   L   G   V   E   Y   A   Q   A   369

1229 CAG GGA AGT AGC ATT AAC GAG GAT ATG GCT GCC GAG CTA AAG CTA ACC CCA GCA GCA ATG 1288
370  Q   G   S   S   I   N   E   D   M   A   A   E   L   K   L   T   P   A   A   M   389

1289 AAG GGC CTG GCA GCT GCT GCC CAA CGG GTC TCC GAC GAT ACC AGC AGC ATA TAC ATG CCT 1348
390  K   G   L   A   A   A   A   Q   R   V   S   D   D   T   S   S   I   Y   M   P   409

1349 ACT CAA CAA GTC GGA GTC CTC ACT GGG CTT AGC GAG GGG GGG TCC CAA GCT CTA CAA GGC 1408
410  T   Q   Q   V   G   V   L   T   G   L   S   E   G   G   S   Q   A   L   Q   G   429

1409 GGA TCG AAT AGA TCG CAA GGG CAA CCA GAA GCC GGG GAT GGG GAG ACC CAA TTC CTG GAT 1468
430  G   S   N   R   S   Q   G   Q   P   E   A   G   D   G   E   T   Q   F   L   D   449

1469 CTG ATG AGA GCG GTA GCA AAT AGC ATG AGG GAG GCG CCA AAC TCT GCA CAG GGC ACT CCC 1528
450  L   M   R   A   V   A   N   S   M   R   E   A   P   N   S   A   Q   G   T   P   469

1529 CAA TCG GGG CCT CCC CCA ACT CCT GGG CCA TCC CAA GAT AAC GAC ACC GAC TGG GGG TAT 1588
470  Q   S   G   P   P   P   T   P   G   P   S   Q   D   N   D   T   D   W   G   Y   489

1589 TGA tggacaaaacccagcctgcttccacaaaaacatcccaatgccctcacccgtagtcgaccctcgatttgcggctct 1667
490  *                                                                              490

1668 atatgaccacaccctcaaacaaacatcccctcttcctcccctccccctgctgtacaactccgcacgccctagataccac 1747

1748 aggcacaatgcggctcactaacaatcaaaacagagccgagggaattagaaaaaagtacgggtagaagagggatattcaga 1827

1828 gatcagggcaagtctcccgagtctctgctctctcctctacctgatagaccaggacaaac ATG GCC ACC TTT ACA 1901
1                                                               M   A   T   F   T   5

1902 GAT GCA GAG ATC GAC GAG CTA TTT GAG ACA AGT GGA ACT GTC ATT GAC AAC ATA ATT ACA 1961
6    D   A   E   I   D   E   L   F   E   T   S   G   T   V   I   D   N   I   I   T   25

1962 GCC CAG GGT AAA CCA GCA GAG ACT GTT GGA AGG AGT GCA ATC CCA CAA GGC AAG ACC AAG 2021
26   A   Q   G   K   P   A   E   T   V   G   R   S   A   I   P   Q   G   K   T   K   45

2022 GTG CTG AGC GCA GCA TGG GAG AAG CAT GGG AGC ATC CAG CCA CCG GCC AGT CAA GAC AAC 2081
46   V   L   S   A   A   W   E   K   H   G   S   I   Q   P   P   A   S   Q   D   N   65

2082 CCC GAT CGA CAG GAC AGA TCT GAC AAA CAA CCA TCC ACA CCC GAG CAA ACG ACC CCG CAT 2141
66   P   D   R   Q   D   R   S   D   K   Q   P   S   T   P   E   Q   T   T   P   H   85

2142 GAC AGC CCG CCG GCC ACA TCC GCC GAC CAG CCC CCC ACC CAG GCC ACA GAC GAA GCC GTC 2201
86   D   S   P   P   A   T   S   A   D   Q   P   P   T   Q   A   T   D   E   A   V   105

2202 GAC ACA CAG TTC AGG ACC GGA GCA AGC AAC TCT CTG CTG TTG ATG CTT GAC AAG CTC AGC 2261
106  D   T   Q   F   R   T   G   A   S   N   S   L   L   L   M   L   D   K   L   S   125

2262 AAT AAA TCG TCC AAT GCT AAA AAG GGC CCA TGG TCG AGC CCC CAA GAG GGG AAT CAC CAA 2321
126  N   K   S   S   N   A   K   K   G   P   W   S   S   P   Q   E   G   N   H   Q   145

2322 CGT CCG ACT CAA CAG CAG GGG AGT CAA CCC AGT CGC GGA AAC AGT CAG GAA AGA CCG CAG 2381
146  R   P   T   Q   Q   Q   G   S   Q   P   S   R   G   N   S   Q   E   R   P   Q   165
```

Fig. 3 continued

```
2382 AAC CAA GTC AAG GCC GCC CCT GGA AAC CAG GGC ACA GAC GTG AAC ACA GCA TAT CAT GGA 2441
 166 N   Q   V   K   A   A   P   G   N   Q   G   T   D   V   N   T   A   Y   H   G   185

2442 CAA TGG GAG GAG TCA CAA CTA TCA GCT GGT GCA ACC CCT CAT GCT CTC CGA TCA AGG CAG 2501
 186 Q   W   E   E   S   Q   L   S   A   G   A   T   P   H   A   L   R   S   R   Q   205

2502 AGC CAA GAC AAT ACC CTT GTA TCT GCG GAT CAT GTC CAG CCA CCT GTA GAC TTT GTG CAA 2561
 206 S   Q   D   N   T   L   V   S   A   D   H   V   Q   P   P   V   D   F   V   Q   225

2562 GCG ATG ATG TCT ATG ATG GAG GCG ATA TCA CAG AGA GTA AGT AAG GTT GAC TAT CAG CTA 2621
 226 A   M   M   S   M   M   E   A   I   S   Q   R   V   S   K   V   D   Y   Q   L   245

2622 GAT CTT GTC TTG AAA CAG ACA TCC TCC ATC CCT ATG ATG CGG TCC GAA ATC CAA CAG CTG 2681
 246 D   L   V   L   K   Q   T   S   S   I   P   M   M   R   S   E   I   Q   Q   L   265

2682 AAA ACA TCT GTT GCA GTC ATG GAA GCC AAC TTG GGA ATG ATG AAG ATT CTG GAT CCC GGT 2741
 266 K   T   S   V   A   V   M   E   A   N   L   G   M   M   K   I   L   D   P   G   285

2742 TGT GCC AAC ATT TCA TCT CTG AGT GAT CTA CGG GCA GTT GCC CGA TCT CAC CCG GTT TTA 2801
 286 C   A   N   I   S   S   L   S   D   L   R   A   V   A   R   S   H   P   V   L   305

2802 GTT TCA GGC CCT GGA GAC CCC TCT CCC TAT GTG ACA CAA GGA GGC GAA ATG GCA CTT AAT 2861
 306 V   S   G   P   G   D   P   S   P   Y   V   T   Q   G   G   E   M   A   L   N   325

2862 AAA CTT TCG CAA CCA GTG CCA CAT CCA TCT GAA TTG ATT AAA CCC GCC ACT GCA TGC GGG 2921
 326 K   L   S   Q   P   V   P   H   P   S   E   L   I   K   P   A   T   A   C   G   345

2922 CCT GAT ATA GGA GTG GAA AAG GAC ACT GTC CGT GCA TTG ATC ATG TCA CGC CCA ATG CAC 2981
 346 P   D   I   G   V   E   K   D   T   V   R   A   L   I   M   S   R   P   M   H   365

2982 CCG AGT TCT TCA GCC AAG CTC CTA AGC AAG TTA GAT GCA GCC GGG TCG ATC GAG GAA ATC 3041
 366 P   S   S   S   A   K   L   L   S   K   L   D   A   A   G   S   I   E   E   I   385

3042 AGG AAA ATC AAG CGC CTT GCT CTA AAT GGC TAA ttactactgccacacgtagcgggtccctgtccactc 3110
 386 R   K   I   K   R   L   A   L   N   G   *                                        396

3111 ggcatcacacggaatctgcaccgagttccccccgcagacccaaggtccaactctccaagcggcaatcctctctcgcttc 3190

3191 ctcagccccactgaatggtcgcgtaaccgtaattaatctagctacatttaagattaagaaaaaatacgggtagaattgga 3270

3271 gtgccccaattgtgccaag ATG GAC TCA TCT AGG ACA ATT GGG CTG TAC TTT GAT TCT GCC CAT 3334
   1                   M   D   S   S   R   T   I   G   L   Y   F   D   S   A   H   15

3335 TCT TCT AGC AAC CTG TTA GCA TTT CCG ATC GTC CTA CAA GGC ACA GGA GAT GGG AAG AAG 3394
  16 S   S   S   N   L   L   A   F   P   I   V   L   Q   G   T   G   D   G   K   K   35

3395 CAA ATC GCC CCG CAA TAT AGG ATC CAG CGC CTT GAC TTG TGG ACT GAT AGT AAG GAG GAC 3454
  36 Q   I   A   P   Q   Y   R   I   Q   R   L   D   L   W   T   D   S   K   E   D   55

3455 TCA GTA TTC ATC ACC ACC TAT GGA TTC ATC TTT CAA GTT GGG AAT GAA GAA GCC ACT GTC 3514
  56 S   V   F   I   T   T   Y   G   F   I   F   Q   V   G   N   E   E   A   T   V   75

3515 GGC ATG ATC GAT GAT AAA CCC AAG CGC GAG TTA CTT TCC GCT GCG ATG CTC TGC CTA GGA 3574
  76 G   M   I   D   D   K   P   K   R   E   L   L   S   A   A   M   L   C   L   G   95

3575 AGC GTC CCA AAT ACC GGA GAC CTT ATT GAG CTG GCA AGG GCC TGT CTC ACT ATG ATA GTC 3634
  96 S   V   P   N   T   G   D   L   I   E   L   A   R   A   C   L   T   M   I   V   115
```

Fig. 3 continued

```
3635 ACA TGC AAG AAG AGT GCA ACT AAT ACT GAG AGA ATG GTT TTC TCA GTA GTG CAG GCA CCC 3694
116  T   C   K   K   S   A   T   N   T   E   R   M   V   F   S   V   V   Q   A   P   135

3695 CAA GTG CTG CAA AGC TGT AGG GTT GTG GCA AAC AAA TAC TCA TCA GTG AAT GCA GTC AAG 3754
136  Q   V   L   Q   S   C   R   V   V   A   N   K   Y   S   S   V   N   A   V   K   155

3755 CAC GTG AAA GCG CCA GAG AAG ATT CCC GGG AGT GGA ACC CTA GAA TAC AAG GTG AAC TTT 3814
156  H   V   K   A   P   E   K   I   P   G   S   G   T   L   E   Y   K   V   N   F   175

3815 GTC TCC TTG ACT GTG GTA CCG AAG AAG GAT GTC TAC AAG ATC CCA GCT GCA GTA TTG AAG 3874
176  V   S   L   T   V   V   P   K   K   D   V   Y   K   I   P   A   A   V   L   K   195

3875 GTT TCT GGC TCG AGT CTG TAC AAT CTT GCG CTC AAT GTC ACT ATT AAT GTG GAG GTA GAC 3934
196  V   S   G   S   S   L   Y   N   L   A   L   N   V   T   I   N   V   E   V   D   215

3935 CCG AGG AGT CCT TTG GTT AAA TCT TTG TCT AAG TCT GAC AGC GGA TAC TAT GCT AAC CTC 3994
216  P   R   S   P   L   V   K   S   L   S   K   S   D   S   G   Y   Y   A   N   L   235

3995 TTC TTG CAT ATT GGA CTT ATG ACC ACC GTA GAT AGG AAG GGG AAG AAA GTG ACA TTT GAC 4054
236  F   L   H   I   G   L   M   T   T   V   D   R   K   G   K   K   V   T   F   D   255

4055 AAG CTG GAA AAG AAA ATA AGG AGC CTT GAT CTA TCT GTC GGG CTC AGT GAT GTG CTC GGG 4114
256  K   L   E   K   K   I   R   S   L   D   L   S   V   G   L   S   D   V   L   G   275

4115 CCT TCC GTG TTG GTA AAA GCA AGA GGT GCA CGG ACT AAG CTT TTG GCA CCT TTC TTC TCT 4174
276  P   S   V   L   V   K   A   R   G   A   R   T   K   L   L   A   P   F   F   S   295

4175 AGC AGT GGG ACA GCC TGC TAT CCC ATA GCA AAT GCT TCT CCT CAG GTG GCC AAG ATA CTC 4234
296  S   S   G   T   A   C   Y   P   I   A   N   A   S   P   Q   V   A   K   I   L   315

4235 TGG AGT CAA ACC GCG TGC CTG CGG AGC GTT AAA ATC ATT ATC CAA GCA GGT ACC CAA CGC 4294
316  W   S   Q   T   A   C   L   R   S   V   K   I   I   I   Q   A   G   T   Q   R   335

4295 GCT GTC GCA GTG ACC GCC GAC CAC GAG GTT ACC TCT ACT AAG CTG GAG AAG GGG CAC ACC 4354
336  A   V   A   V   T   A   D   H   E   V   T   S   T   K   L   E   K   G   H   T   355

4355 CTT GCC AAA TAC AAT CCT TTT AAG AAA TAA gctgcgtctctgagattgcgctccgcccactcacccagat 4424
356  L   A   K   Y   N   P   F   K   K   *                                           365

4425 catcatgacacaaaaaactaatctgtcttgattatttacagttagtttacctgtctatcaagttagaaaaaacacgggta 4504

4505 gaagattctggatcccggttggcgccctccaggtgcaag ATG GGC TCC AGA CCT TCT ACC AAG AAC CCA 4573
  1                                         M   G   S   R   P   S   T   K   N   P   10

4574 GCA CCT ATG ATG CTG ACT ATC CGG GTT GCG CTG GTA CTG AGT TGC ATC TGT CCG GCA AAC 4633
 11  A   P   M   M   L   T   I   R   V   A   L   V   L   S   C   I   C   P   A   N   30

4634 TCC ATT GAT GGC AGG CCT CTT GCA GCT GCA GGA ATT GTG GTT ACA GGA GAC AAA GCC GTC 4693
 31  S   I   D   G   R   P   L   A   A   A   G   I   V   V   T   G   D   K   A   V   50

4694 AAC ATA TAC ACC TCA TCC CAG ACA GGA TCA ATC ATA GTT AAG CTC CTC CCG AAT CTG CCC 4753
 51  N   I   Y   T   S   S   Q   T   G   S   I   I   V   K   L   L   P   N   L   P   70

4754 AAG GAT AAG GAG GCA TGT GCG AAA GCC CCC TTG GAT GCA TAC AAC AGG ACA TTG ACC ACT 4813
 71  K   D   K   E   A   C   A   K   A   P   L   D   A   Y   N   R   T   L   T   T   90

4814 TTG CTC ACC CCC CTT GGT GAC TCT ATC CGT AGG ATA CAA GAG TCT GTG ACT ACA TCT GGA 4873
 91  L   L   T   P   L   G   D   S   I   R   R   I   Q   E   S   V   T   T   S   G   110
```

Fig. 3 continued

```
4874 GGG GGG AGA CAG GGG CGC CTT ATA GGC GCC ATT ATT GGC GGT GTG GCT CTT GGG GTT GCA 4933
111  G   G   R   Q   G   R   L   I   G   A   I   I   G   G   V   A   L   G   V   A   130

4934 ACT GCC GCA CAA ATA ACA GCG GCC GCA GCT CTG ATA CAA GCC AAA CAA AAT GCT GCC AAC 4993
131  T   A   A   Q   I   T   A   A   A   A   L   I   Q   A   K   Q   N   A   A   N   150

4994 ATC CTC CGA CTT AAA GAG AGC ATT GCC GCA ACC AAT GAG GCT GTG CAT GAG GTC ACT GAC 5053
151  I   L   R   L   K   E   S   I   A   A   T   N   E   A   V   H   E   V   T   D   170

5054 GGA TTA TCG CAA CTA GCA GTG GCA GTT GGG AAG ATG CAG CAG TTT GTT AAT GAC CAA TTT 5113
171  G   L   S   Q   L   A   V   A   V   G   K   M   Q   Q   F   V   N   D   Q   F   190

5114 AAT AAA ACA GCT CAG GAA TTA GAC TGC ATC AAA ATT GCA CAG CAA GTT GGT GTA GAG CTC 5173
191  N   K   T   A   Q   E   L   D   C   I   K   I   A   Q   Q   V   G   V   E   L   210

5174 AAC CTG TAC CTA ACC GAA TTG ACT ACA GTA TTC GGA CCA CAA ATC ACT TCA CCT GCT TTA 5233
211  N   L   Y   L   T   E   L   T   T   V   F   G   P   Q   I   T   S   P   A   L   230

5234 AAC AAG CTG ACT ATT CAG GCA CTT TAC AAT CTA GCT GGT GGA AAT ATG GAT TAC TTA TTG 5293
231  N   K   L   T   I   Q   A   L   Y   N   L   A   G   G   N   M   D   Y   L   L   250

5294 ACT AAG TTA GGT GTA GGG AAC AAT CAA CTC AGC TCA TTA ATC GGT AGC GGC TTA ATC ACC 5353
251  T   K   L   G   V   G   N   N   Q   L   S   S   L   I   G   S   G   L   I   T   270

5354 GGT AAC CCT ATT CTA TAC GAC TCA CAG ACT CAA CTC TTG GGT ATA CAG GTA ACT CTA CCT 5413
271  G   N   P   I   L   Y   D   S   Q   T   Q   L   L   G   I   Q   V   T   L   P   290

5414 TCA GTC GGG AAC CTA AAT AAT ATG CGT GCC ACC TAC TTG GAA ACC TTA TCC GTA AGC ACA 5473
291  S   V   G   N   L   N   N   M   R   A   T   Y   L   E   T   L   S   V   S   T   310

5474 ACC AGG GGA TTT GCC TCG GCA CTT GTC CCC AAA GTG GTG ACA CAG GTC GGT TCT GTG ATA 5533
311  T   R   G   F   A   S   A   L   V   P   K   V   V   T   Q   V   G   S   V   I   330

5534 GAA GAA CTT GAC ACC TCA TAC TGT ATA GAA ACT GAC TTA GAT TTA TAT TGT ACA AGA ATA 5593
331  E   E   L   D   T   S   Y   C   I   E   T   D   L   D   L   Y   C   T   R   I   350

5594 GTA ACG TTC CCT ATG TCC CCT GGT ATT TAT TCC TGC TTG AGC GGC AAT ACG TCG GCC TGT 5653
351  V   T   F   P   M   S   P   G   I   Y   S   C   L   S   G   N   T   S   A   C   370

5654 ATG TAC TCA AAG ACC GAA GGC GCA CTT ACT ACA CCA TAC ATG ACT ATC AAA GGT TCA GTC 5713
371  M   Y   S   K   T   E   G   A   L   T   T   P   Y   M   T   I   K   G   S   V   390

5714 ATC GCC AAC TGC AAG ATG ACA ACA TGT AGA TGT GTA AAC CCC CCG GGT ATC ATA TCG CAA 5773
391  I   A   N   C   K   M   T   T   C   R   C   V   N   P   P   G   I   I   S   Q   410

5774 AAC TAT GGA GAA GCC GTG TCT CTA ATA GAT AAA CAA TCA TGC AAT GTT TTA TCC TTA GGC 5833
411  N   Y   G   E   A   V   S   L   I   D   K   Q   S   C   N   V   L   S   L   G   430

5834 GGG ATA ACT TTA AGG CTC AGT GGG GAA TTC GAT GTA ACT TAT CAG AAG AAT ATC TCA ATA 5893
431  G   I   T   L   R   L   S   G   E   F   D   V   T   Y   Q   K   N   I   S   I   450

5894 CAA GAT TCT CAA GTA ATA ATA ACA GGC AAT CTT GAT ATC TCA ACT GAG CTT GGG AAT GTC 5953
451  Q   D   S   Q   V   I   I   T   G   N   L   D   I   S   T   E   L   G   N   V   470

5954 AAC AAC TCG ATC AGT AAT GCT TTG AAT AAG TTA GAG GAA AGC AAC AGA AAA CTA GAC AAA 6013
471  N   N   S   I   S   N   A   L   N   K   L   E   E   S   N   R   K   L   D   K   490

6014 GTC AAT GTC AAA CTG ACT AGC ACA TCT GCT CTC ATT ACC TAT ATC GTT TTG ACT ATC ATA 6073
491  V   N   V   K   L   T   S   T   S   A   L   I   T   Y   I   V   L   T   I   I   510
```

Fig. 3 continued

```
6074 TCT CTT GTT TTT GGT ATA CTT AGC CTG ATT CTA GCA TGC TAC CTA ATG TAC AAG CAA AAG 6133
511  S   L   V   F   G   I   L   S   L   I   L   A   C   Y   L   M   Y   K   Q   K   530

6134 GCG CAA CAA AAG ACC TTA TTA TGG CTT GGG AAT AAT ACT CTA GAT CAG ATG AGA GCC ACT 6193
531  A   Q   Q   K   T   L   L   W   L   G   N   N   T   L   D   Q   M   R   A   T   550

6194 ACA AAA ATG TGA acacagatgaggaacgaaggtttccctaatagtaatttgtgtgaaagttctggtagtctgtcag 6269
551  T   K   M   *                                                                  554

6270 ttcagagagttaagaaaaaactaccggttgtagatgaccaaaggacgatatacgggtagaacggtaagagaggccgcccc 6349

6350 tcaattgcgagccaggcttcacaacctccgttctaccgcttcaccgacaacagtcctcaatc ATG GAC CGC GCC 6423
   1                                                                M   D   R   A   4

6424 GTT AGC CAA GTT GCG TTA GAG AAT GAT GAA AGA GAG GCA AAA AAT ACA TGG CGC TTG ATA 6483
  5  V   S   Q   V   A   L   E   N   D   E   R   E   A   K   N   T   W   R   L   I   24

6484 TTC CGG ATT GCA ATC TTA TTC TTA ACA GTA GTG ACC TTG GCT ATA TCT GTA GCC TCC CTT 6543
 25  F   R   I   A   I   L   F   L   T   V   V   T   L   A   I   S   V   A   S   L   44

6544 TTA TAT AGC ATG GGG GCT AGC ACA CCT AGC GAT CTT GTA GGC ATA CCG ACT AGG ATT TCC 6603
 45  L   Y   S   M   G   A   S   T   P   S   D   L   V   G   I   P   T   R   I   S   64

6604 AGG GCA GAA GAA AAG ATT ACA TCT ACA CTT GGT TCC AAT CAA GAT GTA GTA GAT AGG ATA 6663
 65  R   A   E   E   K   I   T   S   T   L   G   S   N   Q   D   V   V   D   R   I   84

6664 TAT AAG CAA GTG GCC CTT GAG TCT CCG TTG GCA TTG TTA AAT ACT GAG ACC ACA ATT ATG 6723
 85  Y   K   Q   V   A   L   E   S   P   L   A   L   L   N   T   E   T   T   I   M   104

6724 AAC GCA ATA ACA TCT CTC TCT TAT CAG ATT AAT GGA GCT GCA AAC AAC AGT GGG TGG GGG 6783
105  N   A   I   T   S   L   S   Y   Q   I   N   G   A   A   N   N   S   G   W   G   124

6784 GCA CCT ATC CAT GAC CCA GAT TAT ATA GGG GGG ATA GGC AAA GAA CTC ATT GTA GAT GAT 6843
125  A   P   I   H   D   P   D   Y   I   G   G   I   G   K   E   L   I   V   D   D   144

6844 GCT AGT GAT GTC ACA TCA TTC TAT CCC TCT GCA TTT CAA GAA CAT CTG AAT TTT ATC CCG 6903
145  A   S   D   V   T   S   F   Y   P   S   A   F   Q   E   H   L   N   F   I   P   164

6904 GCG CCT ACT ACA GGA TCA GGT TGC ACT CGA ATA CCC TCA TTT GAC ATG AGT GCT ACC CAT 6963
165  A   P   T   T   G   S   G   C   T   R   I   P   S   F   D   M   S   A   T   H   184

6964 TAC TGC TAC ACC CAT AAT GTA ATA TTG TCT GGA TGC AGA GAT CAC TCA CAT TCA TAT CAG 7023
185  Y   C   Y   T   H   N   V   I   L   S   G   C   R   D   H   S   H   S   Y   Q   204

7024 TAT TTA GCA CTT GGT GTG CTC CGG ACA TCT GCA ACA GGG AGG GTA TTC TTT TCT ACT CTG 7083
205  Y   L   A   L   G   V   L   R   T   S   A   T   G   R   V   F   F   S   T   L   224

7084 CGT TCC ATC AAC CTG GAC GAC ACC CAA AAT CGG AAG TCT TGC AGT GTG AGT GCA ACT CCC 7143
225  R   S   I   N   L   D   D   T   Q   N   R   K   S   C   S   V   S   A   T   P   244

7144 CTG GGT TGT GAT ATG CTG TGC TCG AAA GTC ACG GAG ACA GAG GAA GAA GAT TAT AAC TCA 7203
245  L   G   C   D   M   L   C   S   K   V   T   E   T   E   E   E   D   Y   N   S   264

7204 GCT GTC CCT ACG CGG ATG GTA CAT GGG AGG TTA GGG TTC GAC GGC CAG TAC CAC GAA AAG 7263
265  A   V   P   T   R   M   V   H   G   R   L   G   F   D   G   Q   Y   H   E   K   284

7264 GAC CTA GAT GTC ACA ACA TTA TTC GGG GAC TGG GTG GCC AAC TAC CCA GGA GTA GGG GGT 7323
285  D   L   D   V   T   T   L   F   G   D   W   V   A   N   Y   P   G   V   G   G   304
```

Fig. 3 continued

```
7324 GGA TCT TTT ATT GAC AGC CGC GTA TGG TTC TCA GTC TAC GGA GGG TTA AAA CCC AAT TCA 7383
305  G   S   F   I   D   S   R   V   W   F   S   V   Y   G   G   L   K   P   N   S   324

7384 CCC AGT GAC ACT GTA CAG GAA GGG AAA TAT GTG ATA TAC AAG CGA TAC AAT GAC ACA TGC 7443
325  P   S   D   T   V   Q   E   G   K   Y   V   I   Y   K   R   Y   N   D   T   C   344

7444 CCA GAT GAG CAA GAC TAC CAG ATT CGA ATG GCC AAG TCT TCG TAT AAG CCT GGA CGG TTT 7503
345  P   D   E   Q   D   Y   Q   I   R   M   A   K   S   S   Y   K   P   G   R   F   364

7504 GGT GGG AAA CGC ATA CAG CAG GCT ATC TTA TCT ATC AAG GTG TCA ACA TCC TTA GGC GAA 7563
365  G   G   K   R   I   Q   Q   A   I   L   S   I   K   V   S   T   S   L   G   E   384

7564 GAC CCG GTA CTG ACT GTA CCG CCC AAC ACA GTC ACA CTC ATG GGG GCC GAA GGC AGA ATT 7623
385  D   P   V   L   T   V   P   P   N   T   V   T   L   M   G   A   E   G   R   I   404

7624 CTC ACA GTA GGG ACA TCT CAT TTC TTG TAT CAA CGA GGG TCA TCA TAC TTC TCT CCC GCG 7683
405  L   T   V   G   T   S   H   F   L   Y   Q   R   G   S   S   Y   F   S   P   A   424

7684 TTA TTA TAT CCT ATG ACA GTC AGC AAC AAA ACA GCC ACT CTT CAT AGT CCT TAT ACA TTC 7743
425  L   L   Y   P   M   T   V   S   N   K   T   A   T   L   H   S   P   Y   T   F   444

7744 AAT GCC TTC ACT CGG CCA GGT AGT ATC CCT TGC CAG GCT TCA GCA AGA TGC CCC AAC TCG 7803
445  N   A   F   T   R   P   G   S   I   P   C   Q   A   S   A   R   C   P   N   S   464

7804 TGT GTT ACT GGA GTC TAT ACA GAT CCA TAT CCC CTA ATC TTC TAT AGA AAC CAC ACC TTG 7863
465  C   V   T   G   V   Y   T   D   P   Y   P   L   I   F   Y   R   N   H   T   L   484

7864 CGA GGG GTA TTC GGG ACA ATG CTT GAT GGT GTA CAA GCA AGA CTT AAC CCT GCG TCT GCA 7923
485  R   G   V   F   G   T   M   L   D   G   V   Q   A   R   L   N   P   A   S   A   504

7924 GTA TTC GAT AGC ACA TCC CGC AGT CGC ATT ACT CGA GTG AGT TCA AGC AGT ACC AAA GCA 7983
505  V   F   D   S   T   S   R   S   R   I   T   R   V   S   S   S   S   T   K   A   524

7984 GCA TAC ACA ACA TCA ACT TGT TTT AAA GTG GTC AAG ACT AAT AAG ACC TAT TGT CTC AGC 8043
525  A   Y   T   T   S   T   C   F   K   V   V   K   T   N   K   T   Y   C   L   S   544

8044 ATT GCT GAA ATA TCT AAT ACT CTC TTC GGA GAA TTC AGA ATC GTC CCG TTA CTA GTT GAG 8103
545  I   A   E   I   S   N   T   L   F   G   E   F   R   I   V   P   L   L   V   E   564

8104 ATC CTC AAA GAT GAC GGG GTT AGA GAA GCC AGG TCT GGC TAG ttgagtcaattataaaggagttgg 8169
565  I   L   K   D   D   G   V   R   E   A   R   S   G   *                            578

8170 aaagatggcattgtatcacctatcttctgcgacatcaagaatcaaaccgaatgccggcgcgtgctcgaattccatgttgc 8249

8250 cagttgaccacaatcagccagtgctcatgcgatcagattaagccttgtcattaatctcttgattaagaaaaaatgtaagt 8329

8330 ggcaatgagatacaaggcaaaacagctcatggtaaataatacgggtaggac ATG GCG AGC TCC GGT CCT GAA 8401
1                                                      M   A   S   S   G   P   E   7

8402 AGG GCA GAG CAT CAG ATT ATC CTA CCA GAG CCA CAC CTG TCT TCA CCA TTG GTC AAG CAC 8461
8    R   A   E   H   Q   I   I   L   P   E   P   H   L   S   S   P   L   V   K   H   27

8462 AAA CTA CTC TAT TAC TGG AAA TTA ACT GGG CTA CCG CTT CCT GAT GAA TGT GAC TTC GAC 8521
28   K   L   L   Y   Y   W   K   L   T   G   L   P   L   P   D   E   C   D   F   D   47

8522 CAC CTC ATT CTC AGC CGA CAA TGG AAA AAA ATA CTT GAA TCG GCC TCT CCT GAT ACT GAG 8581
48   H   L   I   L   S   R   Q   W   K   K   I   L   E   S   A   S   P   D   T   E   67
```

Fig. 3 continued

```
8582 AGA ATG ATA AAA CTC GGA AGG GCA GTA CAC CAA ACT CTT AAC CAC AAT TCC AGA ATA ACC 8641
  68 R   M   I   K   L   G   R   A   V   H   Q   T   L   N   H   N   S   R   I   T    87

8642 GGA GTG CTC CAC CCC AGG TGT TTA GAA CAA CTG GCT AAT ATT GAG GTC CCA GAT TCA ACC 8701
  88 G   V   L   H   P   R   C   L   E   Q   L   A   N   I   E   V   P   D   S   T   107

8702 AAC AAA TTT CGG AAG ATT GAG AAG AAG ATC CAA ATT CAC AAC ACG AGA TAT GGA GAA CTG 8761
 108 N   K   F   R   K   I   E   K   K   I   Q   I   H   N   T   R   Y   G   E   L   127

8762 TTC ACA AGG CTG TGT ACG CAT ATA GAG AAG AAA CTG CTG GGG TCA TCT TGG TCT AAC AAT 8821
 128 F   T   R   L   C   T   H   I   E   K   K   L   L   G   S   S   W   S   N   N   147

8822 GTC CCC CGG TCA GAG GAG TTC AGC AGC ATT CGT ACG GAT CCG GCA TTC TGG TTT CAC TCA 8881
 148 V   P   R   S   E   E   F   S   S   I   R   T   D   P   A   F   W   F   H   S   167

8882 AAA TGG TCC ACA GCC AAG TTT GCA TGG CTC CAT ATA AAA CAG ATC CAG AGG CAT CTG ATG 8941
 168 K   W   S   T   A   K   F   A   W   L   H   I   K   Q   I   Q   R   H   L   M   187

8942 GTG GCA GCT AAG ACA AGG TCT GCG GCC AAC AAA TTG GTG ATG CTA ACC CAT AAG GTA GGC 9001
 188 V   A   A   K   T   R   S   A   A   N   K   L   V   M   L   T   H   K   V   G   207

9002 CAA GTC TTT GTC ACT CCT GAA CTT GTC GTT GTG ACG CAT ACG AAT GAG AAC AAG TTC ACA 9061
 208 Q   V   F   V   T   P   E   L   V   V   V   T   H   T   N   E   N   K   F   T   227

9062 TGT CTT ACC CAG GAA CTT GTA TTG ATG TAT GCA GAT ATG ATG GAG GGC AGA GAT ATG GTC 9121
 228 C   L   T   Q   E   L   V   L   M   Y   A   D   M   M   E   G   R   D   M   V   247

9122 AAC ATA ATA TCA ACC ACG GCG GTG CAT CTC AGA AGC TTA TCA GAG AAA ATT GAT GAC ATT 9181
 248 N   I   I   S   T   T   A   V   H   L   R   S   L   S   E   K   I   D   D   I   267

9182 TTG CGG TTA ATA GAC GCT CTG GCA AAA GAC TTG GGT AAT CAA GTC TAC GAT GTT GTA TCA 9241
 268 L   R   L   I   D   A   L   A   K   D   L   G   N   Q   V   Y   D   V   V   S   287

9242 CTA ATG GAG GGA TTT GCA TAC GGA GCT GTC CAG CTA CTC GAG CCG TCA GGT ACA TTT GCA 9301
 288 L   M   E   G   F   A   Y   G   A   V   Q   L   L   E   P   S   G   T   F   A   307

9302 GGA GAT TTC TTC GCA TTC AAC CTG CAG GAG CTT AAA GAC ATT CTA ATT GGC CTC CTC CCC 9361
 308 G   D   F   F   A   F   N   L   Q   E   L   K   D   I   L   I   G   L   L   P   327

9362 AAT GAT ATA GCA GAA TCC GTG ACT CAT GCA ATC GCT ACT GTA TTC TCT GGT TTA GAA CAG 9421
 328 N   D   I   A   E   S   V   T   H   A   I   A   T   V   F   S   G   L   E   Q   347

9422 AAT CAA GCA GCT GAG ATG TTG TGT CTG TTG CGT CTG TGG GGT CAC CCA CTG CTT GAG TCC 9481
 348 N   Q   A   A   E   M   L   C   L   L   R   L   W   G   H   P   L   L   E   S   367

9482 CGT ATT GCA GCA AAG GCA GTC AGG AGC CAA ATG TGC GCA CCG AAA ATG GTA GAC TTT GAT 9541
 368 R   I   A   A   K   A   V   R   S   Q   M   C   A   P   K   M   V   D   F   D   387

9542 ATG ATC CTT CAG GTA CTG TCT TTC TTC AAG GGA ACA ATC ATC AAC GGG TAC AGA AAG AAG 9601
 388 M   I   L   Q   V   L   S   F   F   K   G   T   I   I   N   G   Y   R   K   K   407

9602 AAT GCA GGT GTG TGG CCG CGA GTC AAA GTG GAT ACA ATA TAT GGG AAG GTC ATT GGG CAA 9661
 408 N   A   G   V   W   P   R   V   K   V   D   T   I   Y   G   K   V   I   G   Q   427

9662 CTA CAT GCA GAT TCA GCA GAG ATT TCA CAC GAT ATC ATG TTG AGA GAG TAT AAG AGT TTA 9721
 428 L   H   A   D   S   A   E   I   S   H   D   I   M   L   R   E   Y   K   S   L   447

9722 TCT GCA CTT GAA TTT GAG CCA TGT ATA GAA TAT GAC CCT GTC ACC AAC CTG AGC ATG TTC 9781
 448 S   A   L   E   F   E   P   C   I   E   Y   D   P   V   T   N   L   S   M   F   467
```

Fig. 3 continued

```
9782  CTA AAA GAC AAG GCA ATC GCA CAC CCC AAC GAT AAT TGG CTT GCC TCG TTT AGG CGG AAC  9841
468    L   K   D   K   A   I   A   H   P   N   D   N   W   L   A   S   F   R   R   N   487

9842  CTT CTC TCC GAA GAC CAG AAG AAA CAT GTA AAA GAA GCA ACT TCG ACT AAT CGC CTC TTG  9901
488    L   L   S   E   D   Q   K   K   H   V   K   E   A   T   S   T   N   R   L   L   507

9902  ATA GAG TTT TTA GAG TCA AAT GAT TTT GAT CCA TAT AAA GAG ATG GAA TAT CTG ACG ACC  9961
508    I   E   F   L   E   S   N   D   F   D   P   Y   K   E   M   E   Y   L   T   T   527

9962  CTT GAG TAC CTT AGA GAT GAC AAT GTG GCA GTA TCA TAC TCG CTC AAG GAG AAG GAA GTG  10021
528    L   E   Y   L   R   D   D   N   V   A   V   S   Y   S   L   K   E   K   E   V   547

10022 AAA GTT AAT GGA CGG ATC TTC GCT AAG CTG ACA AAG AAG TTA AGG AAC TGT CAG GTG ATG  10081
548    K   V   N   G   R   I   F   A   K   L   T   K   K   L   R   N   C   Q   V   M   567

10082 GCG GAA GGG ATC CTA GCC GAT CAG ATT GCA CCT TTC TTT CAG GGA AAT GGA GTC ATT CAG  10141
568    A   E   G   I   L   A   D   Q   I   A   P   F   F   Q   G   N   G   V   I   Q   587

10142 GAT AGC ATA TCC TTG ACC AAG AGT ATG CTA GCG ATG AGT CAA CTG TCT TTT AAC AGC AAT  10201
588    D   S   I   S   L   T   K   S   M   L   A   M   S   Q   L   S   F   N   S   N   607

10202 AAG AAA CGT ATC ACT GAC TGT AAA GAA AGA GTA TCT TCA AAC CGC AAT CAT GAT CCG AAA  10261
608    K   K   R   I   T   D   C   K   E   R   V   S   S   N   R   N   H   D   P   K   627

10262 AGC AAG AAC CGT CGG AGA GTT GCA ACC TTC ATA ACA ACT GAC CTG CAA AAG TAC TGT CTT  10321
628    S   K   N   R   R   R   V   A   T   F   I   T   T   D   L   Q   K   Y   C   L   647

10322 AAT TGG AGA TAT CAG ACA ATC AAA TTG TTC GCT CAT GCC ATC AAT CAG TTG ATG GGC CTA  10381
648    N   W   R   Y   Q   T   I   K   L   F   A   H   A   I   N   Q   L   M   G   L   667

10382 CCT CAC TTC TTC GAA TGG ATT CAC CTA AGA CTG ATG GAC ACT ACG ATG TTC GTA GGA GAC  10441
668    P   H   F   F   E   W   I   H   L   R   L   M   D   T   T   M   F   V   G   D   687

10442 CCT TTC AAT CCT CCA AGT GAC CCT ACT GAC TGT GAC CTC TCA AGA GTC CCT AAT GAT GAC  10501
688    P   F   N   P   P   S   D   P   T   D   C   D   L   S   R   V   P   N   D   D   707

10502 ATA TAT ATT GTC AGT GCC AGA GGG GGT ATC GAA GGA TTA TGC CAG AAG CTA TGG ACA ATG  10561
708    I   Y   I   V   S   A   R   G   G   I   E   G   L   C   Q   K   L   W   T   M   727

10562 ATC TCA ATT GCT GCA ATC CAA CTT GCT GCA GCT AGA TCG CAT TGT CGT GTT GCC TGT ATG  10621
728    I   S   I   A   A   I   Q   L   A   A   A   R   S   H   C   R   V   A   C   M   747

10622 GTA CAG GGT GAT AAT CAA GTA ATA GCA GTA ACG AGA GAG GTA AGA TCA GAC GAC TCT CCG  10681
748    V   Q   G   D   N   Q   V   I   A   V   T   R   E   V   R   S   D   D   S   P   767

10682 GAG ATG GTG TTG ACA CAG TTG CAT CAA GCC AGT GAT AAT TTC TTC AAG GAA TTA ATT CAT  10741
768    E   M   V   L   T   Q   L   H   Q   A   S   D   N   F   F   K   E   L   I   H   787

10742 GTC AAT CAT TTG ATT GGC CAT AAT TTG AAG GAT CGT GAA ACC ATC AGG TCA GAC ACA TTC  10801
788    V   N   H   L   I   G   H   N   L   K   D   R   E   T   I   R   S   D   T   F   807

10802 TTC ATA TAC AGC AAA CGA ATC TTC AAA GAT GGA GCA ATC CTC AGT CAA GTC CTC AAA AAT  10861
808    F   I   Y   S   K   R   I   F   K   D   G   A   I   L   S   Q   V   L   K   N   827

10862 TCA TCT AAA TTA GTG CTA GTG TCA GGT GAT CTC AGT GAA AAC ACC GTA ATG TCC TGT GCC  10921
828    S   S   K   L   V   L   V   S   G   D   L   S   E   N   T   V   M   S   C   A   847
```

Fig. 3 continued

```
10922 AAC ATT GCC TCT ACT GTA GCA CGG CTA TGC GAG AAC GGG CTT CCC AAA GAC TTC TGT TAC 10981
  848 N   I   A   S   T   V   A   R   L   C   E   N   G   L   P   K   D   F   C   Y    867

10982 TAT TTA AAC TAT ATA ATG AGT TGT GTG CAG ACA TAC TTT GAC TCT GAG TTC TCC ATC ACC 11041
  868 Y   L   N   Y   I   M   S   C   V   Q   T   Y   F   D   S   E   F   S   I   T    887

11042 AAC AAT TCG CAC CCC GAT CTT AAT CAG TCG TGG ATT GAG GAC ATC TCT TTT GTG CAC TCA 11101
  888 N   N   S   H   P   D   L   N   Q   S   W   I   E   D   I   S   F   V   H   S    907

11102 TAT GTT CTG ACT CCT GCC CAA TTA GGG GGA CTG AGT AAC CTT CAA TAC TCA AGG CTC TAC 11161
  908 Y   V   L   T   P   A   Q   L   G   G   L   S   N   L   Q   Y   S   R   L   Y    927

11162 ACT AGA AAT ATC GGT GAC CCG GGG ACT ACT GCT TTT GCA GAG ATC AAG CGA CTA GAA GCA 11221
  928 T   R   N   I   G   D   P   G   T   T   A   F   A   E   I   K   R   L   E   A    947

11222 GTG GGA TTA CTG AGT CCT AAC ATT ATG ACT AAT ATC TTA ACT AGG CCG CCT GGG AAT GGA 11281
  948 V   G   L   L   S   P   N   I   M   T   N   I   L   T   R   P   P   G   N   G    967

11282 GAT TGG GCC AGT CTG TGC AAC GAC CCA TAC TCT TTC AAT TTT GAG ACT GTT GCA AGC CCA 11341
  968 D   W   A   S   L   C   N   D   P   Y   S   F   N   F   E   T   V   A   S   P    987

11342 AAT ATT GTT CTT AAG AAA CAT ACG CAA AGA GTC CTA TTT GAA ACT TGT TCA AAT CCC TTA 11401
  988 N   I   V   L   K   K   H   T   Q   R   V   L   F   E   T   C   S   N   P   L   1007

11402 TTG TCT GGA GTG CAC ACA GAG GAT AAT GAG GCA GAA GAG AAG GCA TTG GCT GAA TTC TTG 11461
 1008 L   S   G   V   H   T   E   D   N   E   A   E   E   K   A   L   A   E   F   L   1027

11462 CTT AAT CAA GAG GTG ATT CAT CCC CGC GTT GCG CAT GCC ATC ATG GAG GCA AGC TCT GTA 11521
 1028 L   N   Q   E   V   I   H   P   R   V   A   H   A   I   M   E   A   S   S   V   1047

11522 GGT AGG AGA AAG CAA ATT CAA GGG CTT GTT GAC ACA ACA AAC ACC GTA ATT AAG ATT GCG 11581
 1048 G   R   R   K   Q   I   Q   G   L   V   D   T   T   N   T   V   I   K   I   A   1067

11582 CTT ACT AGG AGG CCA TTA GGC ATC AAG AGG CTG ATG CGG ATA GTC AAT TAT TCT AGC ATG 11641
 1068 L   T   R   R   P   L   G   I   K   R   L   M   R   I   V   N   Y   S   S   M   1087

11642 CAT GCA ATG CTG TTT AGA GAC GAT GTT TTT TCC TCC AGT AGA TCC AAC CAC CCC TTA GTC 11701
 1088 H   A   M   L   F   R   D   D   V   F   S   S   S   R   S   N   H   P   L   V   1107

11702 TCT TCT AAT ATG TGT TCT CTG ACA CTG GCA GAC TAT GCA CGG AAT AGA AGC TGG TCA CCT 11761
 1108 S   S   N   M   C   S   L   T   L   A   D   Y   A   R   N   R   S   W   S   P   1127

11762 TTG ACG GGA GGC AGG AAA ATA CTG GGT GTA TCT AAT CCT GAT ACG ATA GAA CTC GTA GAG 11821
 1128 L   T   G   G   R   K   I   L   G   V   S   N   P   D   T   I   E   L   V   E   1147

11822 GGT GAG ATT CTT AGT GTA AGC GGA GGG TGT ACA AGA TGT GAC AGC GGA GAT GAA CAA TTT 11881
 1148 G   E   I   L   S   V   S   G   G   C   T   R   C   D   S   G   D   E   Q   F   1167

11882 ACT TGG TTC CAT CTT CCA AGC AAT ATA GAA TTG ACC GAT GAC ACC AGC AAG AAT CCT CCG 11941
 1168 T   W   F   H   L   P   S   N   I   E   L   T   D   D   T   S   K   N   P   P   1187

11942 ATG AGG GTA CCA TAT CTC GGG TCA AAG ACA CAG GAG AGG AGA GCT GCC TCA CTT GCA AAA 12001
 1188 M   R   V   P   Y   L   G   S   K   T   Q   E   R   R   A   A   S   L   A   K   1207

12002 ATA GCT CAT ATG TCG CCA CAT GTA AAG GCT GCC CTA AGG GCA TCA TCC GTG TTG ATC TGG 12061
 1208 I   A   H   M   S   P   H   V   K   A   A   L   R   A   S   S   V   L   I   W   1227

12062 GCT TAT GGG GAT AAT GAA GTA AAT TGG ACT GCT GCT CTT ACG ATT GCA AAA TCT CGG TGT 12121
 1228 A   Y   G   D   N   E   V   N   W   T   A   A   L   T   I   A   K   S   R   C   1247
```

Fig. 3 continued

```
12122 AAT GTA AAC TTA GAG TAT CTT CGG TTA CTG TCC CCT TTA CCC ACG GCT GGG AAT CTT CAA 12181
1248  N   V   N   L   E   Y   L   R   L   L   S   P   L   P   T   A   G   N   L   Q   1267

12182 CAT AGA CTA GAT GAT GGT ATA ACT CAG ATG ACA TTC ACC CCT GCA TCT CTC TAC AGG TGT 12241
1268  H   R   L   D   D   G   I   T   Q   M   T   F   T   P   A   S   L   Y   R   C   1287

12242 CAC CTT ACA TTC ACA TAT CCA ATG ATT CTC AAA GGC TGT TCA CTG AAG AAG GAG TCA AAG 12301
1288  H   L   T   F   T   Y   P   M   I   L   K   G   C   S   L   K   K   E   S   K   1307

12302 AGG GGA ATG TGG TTT ACC AAC AGA GTC ATG CTC TTG GGT TTA TCT CTA ATC GAA TCG ATC 12361
1308  R   G   M   W   F   T   N   R   V   M   L   L   G   L   S   L   I   E   S   I   1327

12362 TTT CCA ATG ACA ACA ACC AGG ACA TAT GAT GAG ATC ACA CTG CAC CTA CAT AGT AAA TTT 12421
1328  F   P   M   T   T   T   R   T   Y   D   E   I   T   L   H   L   H   S   K   F   1347

12422 AGT TGC TGT ATC AGA GAA GCA CCT GTT GCG GTT CCT TTC GAG CTA CTT GGG GTG GTA CCG 12481
1348  S   C   C   I   R   E   A   P   V   A   V   P   F   E   L   L   G   V   V   P   1367

12482 GAA CTG AGG ACA GTG ACC TCA AAT AAG TTT ATG TAT GAT CCT AGC CCT GTA TCG GAG GGA 12541
1368  E   L   R   T   V   T   S   N   K   F   M   Y   D   P   S   P   V   S   E   G   1387

12542 GAC TTT GCG AGA CTT GAC TTA GCT ATC TTC AAG AGT TAT GAG CTT AAT CTG GAG TCA TAT 12601
1388  D   F   A   R   L   D   L   A   I   F   K   S   Y   E   L   N   L   E   S   Y   1407

12602 CCC ACG ATA GAG CTA ATG AAC ATT CTT TCA ATA TCC AGC GGG AAG TTG ATT GGC CAG TCT 12661
1408  P   T   I   E   L   M   N   I   L   S   I   S   S   G   K   L   I   G   Q   S   1427

12662 GTG GTT TCT TAT GAT GAA GAT ACC TCC ATA AAG AAT GAC GCC ATA ATA GTG TAT GAC AAT 12721
1428  V   V   S   Y   D   E   D   T   S   I   K   N   D   A   I   I   V   Y   D   N   1447

12722 ACC CGA AAT TGG ATC AGT GAA GCT CAG AAT TCA GAT GTG GTC CGC CTA TTT GAA TAT GCA 12781
1448  T   R   N   W   I   S   E   A   Q   N   S   D   V   V   R   L   F   E   Y   A   1467

12782 GCA CTT GAA GTG CTC CTC GAC TGT TCT TAC CAA CTC TAT TAC CTG AGA GTA AGA GGC CTA 12841
1468  A   L   E   V   L   L   D   C   S   Y   Q   L   Y   Y   L   R   V   R   G   L   1487

12842 GAC AAT ATT GTC TTA TAT ATG GGT GAT TTA TAC AAG AAT ATG CCA GGA ATT CTA CTT TCC 12901
1488  D   N   I   V   L   Y   M   G   D   L   Y   K   N   M   P   G   I   L   L   S   1507

12902 AAC ATT GCA GCT ACA ATA TCT CAT CCC GTC ATT CAT TCA AGG TTA CAT GCA GTG GGC CTG 12961
1508  N   I   A   A   T   I   S   H   P   V   I   H   S   R   L   H   A   V   G   L   1527

12962 GTC AAC CAT GAC GGA TCA CAC CAA CTT GCA GAT ACG GAT TTT ATC GAA ATG TCT GCA AAA 13021
1528  V   N   H   D   G   S   H   Q   L   A   D   T   D   F   I   E   M   S   A   K   1547

13022 CTA TTA GTA TCT TGC ACC CGA CGT GTG ATC TCC GGC TTA TAT TCA GGA AAT AAG TAT GAT 13081
1548  L   L   V   S   C   T   R   R   V   I   S   G   L   Y   S   G   N   K   Y   D   1567

13082 CTG CTG TTC CCA TCT GTC TTA GAT GAT AAC CTG AAT GAG AAG ATG CTT CAG CTG ATA TCC 13141
1568  L   L   F   P   S   V   L   D   D   N   L   N   E   K   M   L   Q   L   I   S   1587

13142 CGG TTA TGC TGT CTG TAC ACG GTA CTC TTT GCT ACA ACA AGA GAA ATC CCG AAA ATA AGA 13201
1588  R   L   C   C   L   Y   T   V   L   F   A   T   T   R   E   I   P   K   I   R   1607

13202 GGC TTA ACT GCA GAA GAG AAA TGT TCA ATA CTC ACT GAG TAT TTA CTG TCG GAT GCT GTG 13261
1608  G   L   T   A   E   E   K   C   S   I   L   T   E   Y   L   L   S   D   A   V   1627
```

Fig. 3 continued

```
13262 AAA CCA TTA CTT AGC CCC GAT CAA GTG AGC TCT ATC ATG TCT CCT AAC ATA ATT ACA TTC 13321
 1628  K   P   L   L   S   P   D   Q   V   S   S   I   M   S   P   N   I   I   T   F  1647

13322 CCA GCT AAT CTG TAC TAC ATG TCT CGG AAG AGC CTC AAT TTG ATC AGG GAA AGG GAG GAC 13381
 1648  P   A   N   L   Y   Y   M   S   R   K   S   L   N   L   I   R   E   R   E   D  1667

13382 AGG GAT ACT ATC CTG GCG TTG TTG TTC CCC CAA GAG CCA TTA TTA GAG TTC CCT TCT GTG 13441
 1668  R   D   T   I   L   A   L   L   F   P   Q   E   P   L   L   E   F   P   S   V  1687

13442 CAA GAT ATT GGT GCT CGA GTG AAA GAT CCA TTC ACC CGA CAA CCT GCG GCA TTT TTG CAA 13501
 1688  Q   D   I   G   A   R   V   K   D   P   F   T   R   Q   P   A   A   F   L   Q  1707

13502 GAG TTA GAT TTG AGT GCT CCA GCA AGG TAT GAC GCA TTC ACA CTT AGT CAG ATT CAT CCT 13561
 1708  E   L   D   L   S   A   P   A   R   Y   D   A   F   T   L   S   Q   I   H   P  1727

13562 GAA CTC ACA TCT CCA AAT CCG GAG GAA GAC TAC TTA GTA CGA TAC TTG TTC AGA GGG ATA 13621
 1728  E   L   T   S   P   N   P   E   E   D   Y   L   V   R   Y   L   F   R   G   I  1747

13622 GGG ACT GCA TCT TCC TCT TGG TAT AAG GCA TCT CAT CTC CTT TCT GTA CCC GAG GTA AGA 13681
 1748  G   T   A   S   S   S   W   Y   K   A   S   H   L   L   S   V   P   E   V   R  1767

13682 TGT GCA AGA CAC GGG AAC TCC TTA TAC TTA GCT GAA GGG AGC GGA GCC ATC ATG AGT CTT 13741
 1768  C   A   R   H   G   N   S   L   Y   L   A   E   G   S   G   A   I   M   S   L  1787

13742 CTC GAA CTG CAT GTA CCA CAT GAA ACT ATC TAT TAC AAT ACG CTC TTT TCA AAT GAG ATG 13801
 1788  L   E   L   H   V   P   H   E   T   I   Y   Y   N   T   L   F   S   N   E   M  1807

13802 AAC CCC CCG CAA CGA CAT TTC GGG CCG ACC CCA ACT CAG TTT TTG AAT TCG GTT GTT TAT 13861
 1808  N   P   P   Q   R   H   F   G   P   T   P   T   Q   F   L   N   S   V   V   Y  1827

13862 AGG AAT CTA CAG GCG GAG GTA ACA TGC AAA GAT GGA TTT GTC CAA GAG TTC CGT CCA TTA 13921
 1828  R   N   L   Q   A   E   V   T   C   K   D   G   F   V   Q   E   F   R   P   L  1847

13922 TGG AGA GAA AAT ACA GAG GAA AGT GAC CTG ACC TCA GAT AAA GCA GTG GGG TAT ATT ACA 13981
 1848  W   R   E   N   T   E   E   S   D   L   T   S   D   K   A   V   G   Y   I   T  1867

13982 TCT GCA GTG CCC TAC AGA TCT GTA TCA TTG CTG CAT TGT GAC ATT GAA ATT CCT CCA GGG 14041
 1868  S   A   V   P   Y   R   S   V   S   L   L   H   C   D   I   E   I   P   P   G  1887

14042 TCC AAT CAA AGC TTA CTA GAT CAA CTA GCT ATC AAT TTA TCT CTG ATT GCC ATG CAT TCT 14101
 1888  S   N   Q   S   L   L   D   Q   L   A   I   N   L   S   L   I   A   M   H   S  1907

14102 GTA AGG GAG GGC GGG GTA GTA ATC ATC AAA GTG TTG TAT GCA ATG GGA TAC TAC TTT CAT 14161
 1908  V   R   E   G   G   V   V   I   I   K   V   L   Y   A   M   G   Y   Y   F   H  1927

14162 CTA CTC ATG AAC TTG TTT GCT CCG TGT TCC ACA AAA GGA TAT ATT CTC TCT AAT GGT TAT 14221
 1928  L   L   M   N   L   F   A   P   C   S   T   K   G   Y   I   L   S   N   G   Y  1947

14222 GCA TGT CGA GGA GAT ATG GAG TGT TAC CTG GTA TTT GTC ATG GGT TAC CTG GGC GGG CCT 14281
 1948  A   C   R   G   D   M   E   C   Y   L   V   F   V   M   G   Y   L   G   G   P  1967

14282 ACA TTT GTA CAT GAG GTG GTG AGG ATG GCA AAA ACT CTG GTG CAG CGG CAC GGT ACG CTC 14341
 1968  T   F   V   H   E   V   V   R   M   A   K   T   L   V   Q   R   H   G   T   L  1987

14342 TTG TCT AAA TCA GAT GAG ATC ACA CTG ACC AGG TTA TTC ACC TCA CAG CGG CAG CGT GTG 14401
 1988  L   S   K   S   D   E   I   T   L   T   R   L   F   T   S   Q   R   Q   R   V  2007

14402 ACA GAC ATC CTA TCC AGT CCT TTA CCA AGA TTA ATA AAG TAC TTG AGG AAG AAT ATT GAC 14461
 2008  T   D   I   L   S   S   P   L   P   R   L   I   K   Y   L   R   K   N   I   D  2027
```

Fig. 3 continued

```
14462 ACT GCG CTG ATT GAA GCC GGG GGA CAG CCC GTC CGT CCA TTC TGT GCG GAG AGT CTG GTG 14521
2028  T   A   L   I   E   A   G   G   Q   P   V   R   P   F   C   A   E   S   L   V   2047

14522 AGC ACG CTA GCG AAC ATA ACT CAG ATA ACC CAG ATT ATC GCT AGT CAC ATT GAC ACA GTT 14581
2048  S   T   L   A   N   I   T   Q   I   T   Q   I   I   A   S   H   I   D   T   V   2067

14582 ATC CGG TCT GTG ATA TAT ATG GAA GCT GAG GGT GAT CTC GCT GAC ACA GTA TTT CTA TTT 14641
2068  I   R   S   V   I   Y   M   E   A   E   G   D   L   A   D   T   V   F   L   F   2087

14642 ACC CCT TAC AAT CTC TCT ACT GAC GGG AAA AAG AGG ACA TCA CTT ATA CAG TGC ACG AGA 14701
2088  T   P   Y   N   L   S   T   D   G   K   K   R   T   S   L   I   Q   C   T   R   2107

14702 CAG ATC CTA GAG GTT ACA ATA CTA GGT CTT AGA GTC GAA AAT CTC AAT AAA ATA GGC GAT 14761
2108  Q   I   L   G   V   T   I   L   G   L   R   V   E   N   L   N   K   I   G   D   2127

14762 ATA ATC AGC CTA GTG CTT AAA GGC ATG ATC TCC ATG GAG GAC CTT ATC CCA CTA AGG ACA 14821
2128  I   I   S   L   V   L   K   G   M   I   S   M   E   D   L   I   P   L   R   T   2147

14822 TAC TTG AAG CAT AGT ACC TGC CCT AAA TAT TTG AAG GCT GTC CTA GGT ATT ACC AAA CTC 14881
2148  Y   L   K   H   S   T   C   P   K   Y   L   K   A   V   L   G   I   T   K   L   2167

14882 AAA GAA ATG TTT ACA GAC ACT TCT GTA TTG TAC TTG ACT CGT GCT CAA CAA AAA TTC TAC 14941
2168  K   E   M   F   T   D   T   S   V   L   Y   L   T   R   A   Q   Q   K   F   Y   2187

14942 ATG AAA ACT ATA GGC AAT GCA GTC AAA GGA TAT TAC AGT AAC TGT GAC TCT TAA cgaaaatc 15003
2188  M   K   T   I   G   N   A   V   K   G   Y   Y   S   N   C   D   S   *           2205

15004 acatattaataggctcctttttttggccaattgtattcttgttgatttaatcatattatgttagaaaaaagttgaaccctg 15083

15084 actccttaggactcgaattcgaactcaaataaatgtcttaaaaaaaggttgcgcacaattattcttgagtgtagtctcgt 15163

15164 cattcaccaaatctttgtttggt                                                          15186
```

Fig. 4B

Construction of genome-length cDNA clones of
NDV "LaSota" E13-1 in pOLTV535

Fig. 4B, continued
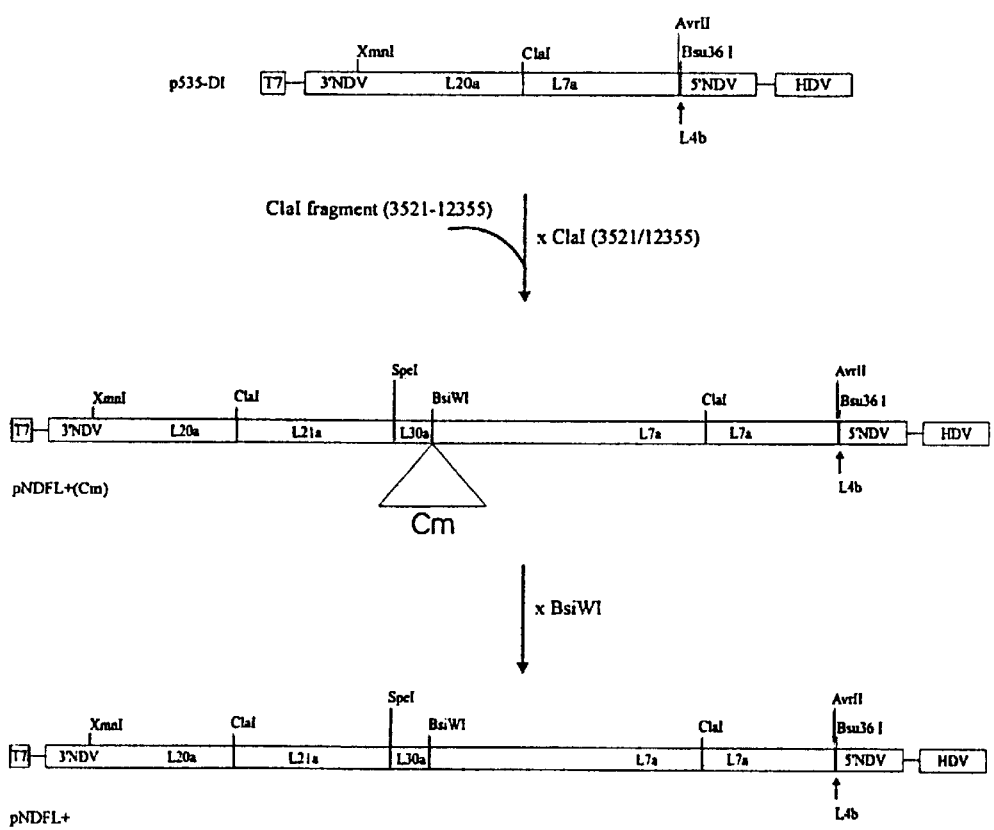

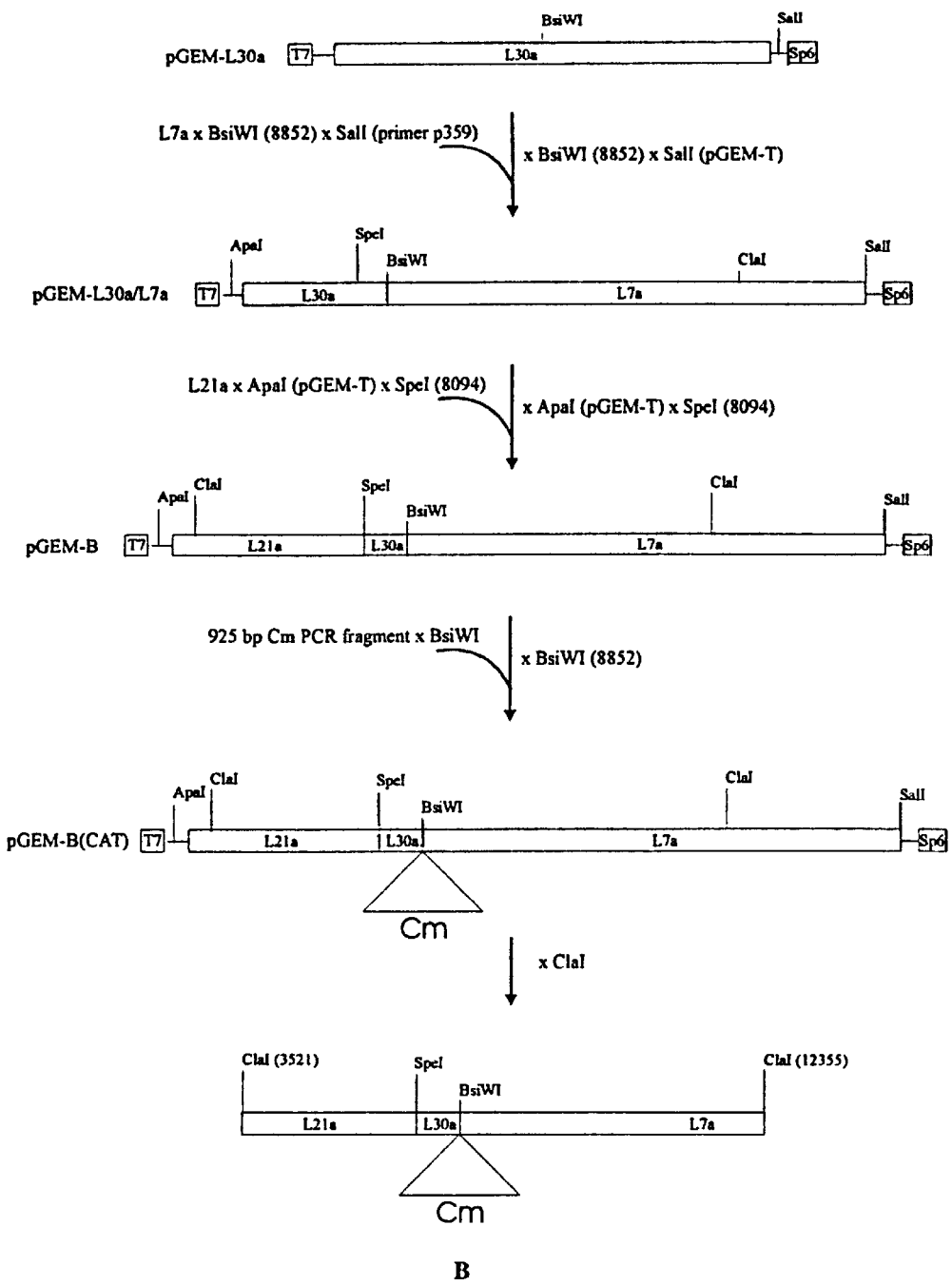
Fig. 4B, continued
B

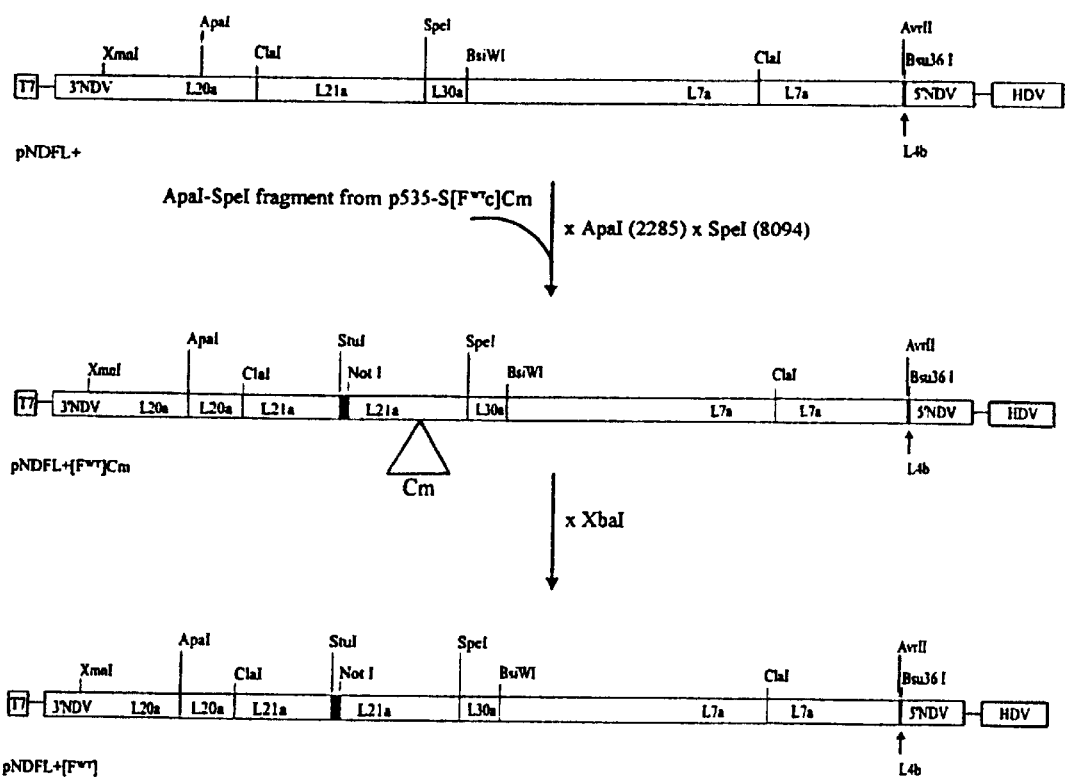
Fig. 4C, continued

```
                                             *                 *                 *                 *                 *                 *
           ┌─ CDV   : ------------------------------------------------------------ :   -
           │  MeV   : ------------------------------------------------------------ :   -
Mobillivrus│  RDV   : ------------------------------------------------------------ :   -
           └─ bPIV3 : ------------------------------------------------------------ :   -
Paramyxovirus┌ hPIV3: ------------------------------------------------------------ :   -
           │  SeV   : -------AGTAAGAA :   8
           └─ NDV   : TTAGAAAAAAGTTGAACCCTGACTCCTTAGGACTCGAATTCGAACTCAAATAAATGTCTTAAAA : 64
           ┌─ hPIV2 : ------------------------------------------------------------ :   -
Rubulavirus│  MuV   : ------------------------------------------------------------ :   -
           │  SV41  : ------------------------------------------------------------ :   -
           └─ SV5   : ------------------------------------------------------------ :   -

*        80        *       100        *       120
           ┌─ CDV   : ----ATACGAAAAAAACAACGGTTATTAATAAGTTATCATACCCAGCTTTGTCTGGT :  54
           │  MeV   : -----ATTAAGAAAACTTTGAAAATACGAAGTTTCTATTCCCAGCTTTGTCTGGT :  51
Mobillivrus│  RDV   : -----ACTAAGAAAACTTCAAAGATGTGAAGTTTCTATCCCCAGCTTTTCTGTCTGGT :  51
           └─ bPIV3 : ----AGTAAGAAAAACATATATATATATATATACCAAACAGAGTTTTCTCTTGTTGGT :  55
Paramyxovirus┌ hPIV3: ----AGTAAGAAAAACATGTAATATATATATATATACCAAACAGAGTTCTTCTTGTTTGGT : 55
           │  SeV   : AAACTTACAAGAAGACAAGAAAATTTAAAGGATACATATCTCTTAAACTCTTGTCTGGT :  68
           └─ NDV   : AAAGGTTGCGCAATTATTCTTGAGTGTAGTCTCGTCTCTCATTCACCAAATCTTGTTTGGT : 124
           ┌─ hPIV2 : -------------------TTTAAGAAAAACATATTGATTTACTTTCTCCCCTTGGT :  32
Rubulavirus│  MuV   : ---------------------TTAAGAAAAAATTGATTTTACTTTCCGTTCTCCCCTTGGT : 35
           │  SV41  : --------------------TTAAGAAAAAATATCCGTTCTCCCCTTGGT :  30
           └─ SV5   : ---------------------TTAAGAAAAAGAAGAGGATTAATCTTGGTTTTCCCCTTGGT : 42
                                                                            TGGT
```

Fig. 6

NEWCASTLE DISEASE VIRUS INFECTIOUS CLONES, VACCINES AND DIAGNOSTIC ASSAYS

CROSS-REFERENCE TO RELATED APPLICATIONS

This application claims priority to and is a continuation of the national phase of International Application No. PCT/NL99/00377, filed on Jun. 7, 1999, designating the United States of America, the contents of which are incorporated by this reference, which PCT International Patent Application itself claims priority from European Patent Office Application Serial No. 98202054.7 filed 19 Jun. 1998.

BACKGROUND OF THE INVENTION

Field of the Invention

The invention relates to Newcastle disease virus infections of poultry.

Newcastle disease virus (NDV) is one of the most diverse and deadly avian pathogens. The almost simultaneous occurrence of Newcastle disease as an apparent new disease in several different geographical locations and the great variation in the severity of the disease has caused some problems with nomenclature.

The disease has been termed pseudo fowl pest, pseudo poultry plague, avian pest, avian distemper and avian pneumoencephalitis. The importance of the disease is primarily due to the development of the poultry industry during the 20th Century into a highly efficient international industry which is dependent on intensive trade between countries.

It is generally assumed that the first outbreaks of Newcastle disease occurred in 1926 in Java, Indonesia, and in Newcastle-upon-Tyne, England (Kraneveld, 1926; Doyle 1927). The name Newcastle disease was coined by Doyle as a temporary name to avoid a descriptive name that might be confused with other diseases. It later became clear that other less severe diseases were caused by viruses indistinguishable from NDV. In the US a relatively mild respiratory disease was termed avian pneumoencephalitis and was shown to be caused by NDV (Beach, 1944). Within a few years, numerous NDV isolations that caused extremely mild or no disease in chickens were made around the world.

The following methods have been implicated in the spread of the disease: 1) movement of live birds, feral birds, game birds, racing pigeons and commercial poultry; 2) movement of people and equipment; 3) movement of poultry products; 4) airborne spread; 5) contaminated poultry feed; 6) contaminated water; 7) incompletely inactivated or heterogeneous vaccines. According to the OIE, Newcastle disease is a disease of poultry caused by a virus of avian paramyxovirus serotype 1 (APMV-1) which has an intracerebral pathogenicity index (ICPM) in day-old chicks of 0.7 or greater. Virulent virus can also be confirmed by the presence of multiple basic amino acids at the C-terminus of the F2 protein and F (phenylanine) at residue 117, the N-terminus of the F1 protein. Failure to demonstrate this amino acid sequence would require characterisation by ICPI tests. The word 'poultry' refers to domestic fowl, turkeys, guinea fowl, ducks, geese, quails, pigeons, pheasants, partridges and ratites that are reared or kept in captivity for breeding, the production of meat or eggs for consumption, or for restocking supplies of game.

According to Alexander (1988) three panzootics of Newcastle disease have occurred since the first recognition of the disease. The first represented the initial outbreaks of the disease and appears to have arisen in South-East Asia. Isolated outbreaks, such as the one in England in 1926, were chance introductions ahead of the mainstream which slowly moved through Asia to Europe.

A second panzootic appears to have begun in the Middle East in the late 1960's and reached most countries by 1973 The more rapid spread of the second panzootic was probably caused by the major revolution of the poultry industry with considerable international trade.

A third panzootic primarily affected domesticated birds such as pigeons and doves (Vindevogel and Duchatel, 1988). The disease apparently arose in the Middle East in the late 1970's. By 1981 it had reached Europe and then spread rapidly to all parts of the world, largely as a result of contact between birds at races and shows and the international trade in such birds.

Nowadays, Newcastle disease is still widespread in many countries of Asia, Africa, the Americas, and Europe. Only the countries of Oceania appear to be relatively free from the disease (Spradbrow, 1988).

NDV belongs to the order Mononegavirales, family Paramyxoviridae, subfamily Paramyxovirinae, genus Rubulavirus. Apart from NDV, generally called avian pararnyxovirus type-i, eight other serotypes, designated avian paramyxovirus type-2 to -9, can be distinguished on the basis of their antigenic relatedness in hemagglutination-inhibition tests and serum neutralisation tests (Alexander, 1993).

Despite the consistency of the serological grciiping there are some cross-relationships between viruses of the different serotypes.

The genome of NDV is a single-stranded RNA molecule of negative polarity, complementary to the messenger RNA's which code for the virus proteins. The RNA genome is approximately 15,200 nt in size and codes for the following gene products (listed from the 3' end to the 5' end of the genomic RNA): nucleocapsid protein (NP), phosphoprotein (P), matrix protein (M), fusion protein (F), hemagglutinin-neuraminidase (HN), and large polymerase protein (L) (Chambers et al., 1986).

The RNA is complexed with the NP, P and L proteins to form a ribonucleocapsid particle (RNP) that is surrounded by an envelope that is lined at the inside by the M protein. The envelope contains the F and HN proteins which are involved in attachment and penetration of the host cell.

Replication of NDV is similar to the strategy used by other paramyxovirinae. The initial step is attachment of the virus to the host cell receptors, mediated by the HN protein. Fusion of the viral envelope with the host cell membrane is dependent on the action of both the HN and F proteins and results in the release of the RNP into the cytoplasm where virus replication takes place.

The viral RNA-dependent RNA polymerase (which is part of the RNP) produces complementary transcripts that act as mRNA's and are used by the cell's translation machinery for the synthesis of virus proteins. Due to the accumulation of NP protein, the RNA polymerase complex switches from transcription to replication, resulting in the synthesis of full-length genomic and antigenomic RNA molecules.

Newly formed RNP's are encapsidated at the cellular membrane by the action of the M protein and the F and HN proteins which have accumulated in the cellular plasma membrane. Newly formed virus particles are released from the infected cell by a budding mechanism. For more detailed information about NDV replication see Peeples (1988). For a recent review of the molecular biology of paramyxovirinae see Lamb and Kolakofsky (1996).

Apart from commercial domestic poultry (i.e., chickens, turkeys, pheasants, guinea fowl, ducks, geese, pigeons), a wide range of captive, semi-domestic and free-living birds, including migratory waterfowl, is susceptible to NDV and can be primary infection sources (Kaleta and Baldauf, 1988).

The pathogenicity of NDV strains differs greatly with the host. The most resistant species appear to be aquatic birds while the most susceptible are gregarious birds forming temporary or permanent flocks. Chickens are highly susceptible but ducks and geese may be infected and show few or no clinical signs, even with strains which are lethal for chickens.

Newcastle Disease is complicated in that different isolates and strains of the virus may induce enormous variation in the severity of the disease. Beard and Hanson (1984) grouped NDV strains and isolates into different pathotypes that relate to disease signs that may be seen in fully susceptible chickens: 1) viscerotropic velogenic NDV, which produces acute lethal infections in which hemorrhagic lesions are prominent in the gut; and neurotropic velogenic NDV, which produces high mortality preceded by respiratory and neurological signs, but no gut lesions; 2) mesogenic NDV, which produces low mortality, acute respiratory disease and nervous signs in some birds; 3) lentogenic NDV, which produces mild or inapparent respiratory infections or even asymptotnatic enteric NDV, avirulent viruses that appear to replicate primarily in the intestinal tract. Some overlap between the signs associated with the different groups has been reported.

The virus enters the body via the respiratory and the intestinal tract or via the eye. In the trachea, the virus is spread by ciliary action and by cell-to-cell spread. After initial multiplication at the introduction site, virus is carried during episodes of viraemia to spleen, liver, kidney and lungs. Viruses of some strains reach vital organs like liver and kidney very rapidly so that the birds may die before disease symptoms are overt.

Most viruses reach the central nervous system via the blood before significant amounts of antibody exist. A long, asymptomatic carrier state presumed to occur in psittacines constitutes a potential threat to the poultry industry. A long term carrier state of both lentogenic and velogenic virus may also exist in chickens (Heuschele and Easterday, 1970).

During the replication of NDV it is necessary for the precursor glycoprotein Fo to be cleaved to F1 and F2 for the progeny virus to be infectious (Rott and Klenk, 1988). This posttranslational cleavage is mediated by host cell proteases. If cleavage fails to take place, non-infectious virus particles are produced and viral replication cannot proceed. The Fo protein of virulent viruses can be cleaved by a wide range of proteases, but Fo proteins in viruses of low virulence are restricted in their sensitivity and these viruses can only grow in vivo in certain host cell types and in general cannot be grown in vitro.

Lentogenic viruses only replicate in areas with trypsinlike enzymes such as the respiratory and intestinal tract, whereas virulent viruses can replicate in a range of tissues and organs resulting in fatal systemic infection.

Amino acid sequencing of the Fo precursor has shown that low-virulence viruses have a single arginine (R) that links the F2 and F1 chains, whereas virulent strains possess additional basic amino acids forming two pairs such as K/R-X-K/R-R-F at the site of cleavage. Furthermore, the F2 chain of virulent strains generally starts with a phenylalanine residue whereas that of nonvirulent strains generally starts with a leucine.

For a few strains of NDV the HN protein is also produced as a precursor that requires cleavage to be biologically active (Garten et al., 1980; Millar et al., 1988).

Besides cleavability of the F and HN proteins, other viral factors may contribute to pathogenicity. Madansky and Bratt (1978, 1981a, 1981b) have shown that alterations in transcription and translation could modulate growth and cell-to-cell spread of the virus and/or cytopathogenicity.

The initial immune response to infection with NDV is cell mediated and may be detectable as early as 2–3 days after infection with live vaccine strains. This presumably explains the early protection against challenge that has been recorded in vaccinated birds before a measurable antibody response is seen (Gough and Alexander, 1973).

At about 1 week after infection, circulating antibodies may protect the host from re-infection. In the early phase IgM is involved, followed by IgG. Titres and protection peak after about 3 weeks and gradually decline if there is no boosting. This means that for older birds, re-vaccinations are necessary.

Only live vaccines administered by the respiratory route stimulate antibody in all mucosal surfaces as well as in serum. Inactivated vaccine, even when applied via the intramuscular route, does not elicit local resistance in the respiratory tract, despite high concentrations of serum antibody.

This stresses the importance of live vaccines capable of presenting viral antigen to the upper respiratory tract to induce both local and systemic immunity. Small droplets penetrate into the lower respiratory tract thereby provoking a mainly humoral immune response, while coarse droplets stimulate local immunity in the upper respiratory tract.

Therefor, aerosols with a wide range of droplet sizes generate the best overall local and humoral immunity.

It should be noted, however, that despite intensive vaccination with current vaccines creating high levels of antibody titers, virus can still be recovered from mucous surfaces.

The identification of Newcastle disease in the USA led to the use of inactivated vaccines (Hofstad, 1953). The observation that some of the enzootic viruses produced only mild disease resulted first in the development of the mesogenic live vaccine Roakin (Beaudette et al., 1949) and, subsequently, in the development of the milder Hitchner B1 (Hitchner and Johnson, 1948) and LaSota (Goldhaft, 1980) strains, which are now the most widely used live vaccines.

NDV live vaccines can be divided into two groups, lentogenic and mesogenic. Mesogenic strains are suitable only for secondary vaccination of birds due to their greater virulence. The immune response increases as the pathogenicity of the live vaccine increases. Therefore, to obtain the desired level of protection without serious reaction, currently vaccination programs are used that involve sequential use of progressively more virulent vaccines, or live vaccines followed by inactivated vaccines.

One of the main advantages of live vaccines is that they may be administered by inexpensive mass application techniques. A common method of application is via drinking water. However, drinking water application must be carefully monitored as the virus may be inactivated by excessive heat and light and by virucidal impurities in the water.

Mass application of live vaccines by sprays and aerosols is also very popular due to the ease with which large numbers of birds can be vaccinated in a short time. It is important to achieve the correct particle size by controlling the conditions under which the particles are generated.

Currently used live vaccines have several disadvantages. The vaccine may still cause disease signs, depending upon environmental conditions and the presence of complicating infections. Therefore, it is important to use extremely mild virus for primary vaccination and, as a result, multiple vaccinations are usually needed. Furthermore, maternally derived antibodies may prevent successful primary vaccination with lentogenic live vaccines.

Inactivated vaccines are usually produced from infectious allantoic fluid which is treated with formalin or betapropiolactone to kill the virus and mixed with a suitable adjuvant. Inactivated vaccines are administered by injection, either intramuscularly or subcutaneously. Inactivated vaccines are expensive to produce and to apply.

However, inactivated oil-emulsion vaccines are not as adversely affected by maternal immunity as live vaccines and they can be used in day-old chicks. Advantages of inactivated vaccines are the low level of adverse reactions in vaccinated birds, the high level of protective antibodies, and the long duration of protection. None of the above vaccines can serologically be differentiated from wild-type NDV.

The development of recombinant viral vaccines has been of interest to the poultry industry for a number of years. The concept is to insert genes of critical immunizing epitopes of a disease agent of interest into a nonessential gene of a vector virus. Vaccination with the recombinant virus thus results in immunization against both the vector virus as well as the disease agent of interest.

Several types of viruses have been evaluated as potential live viral vaccines for poultry. Two avian viruses that have received most attention are fowlpox virus (FPV) and herpesvirus of turkeys (HVT). Fowlpox virus is a DNA virus that has a large genome and hence is considered to have ample room to carry foreign genes.

When attenuated, FPV does not cause clinical disease and is commonly used as a vaccine in chickens. HVT is also a DNA virus and is classified as serotype III of the Marek's disease virus (MDV) family. HVT is non-pathogenic for chickens yet cross-protective against MDV and is commonly used to vaccinate chickens against Marek's disease.

It has been shown that protection against Newcastle disease can be induced by using recombinant HVT or FPV vaccines (Morgan et al., 1992, 1993; Heckert et al., 1996; Boursnell et al., 1990; Taylor et al., 1990).

However, the onset of protection against Newcastle disease following vaccination with such recombinant vaccines that express either the NDV F protein or both the F and HN proteins was severely delayed compared to that following vaccination with a conventional live or inactivated NDV vaccine, possibly because the recombinant vaccines do not provide a wide enough immunological spectre of antigenically relevant NDV epitopes other than those found on the NDV protein that is expressed by the recombinant vaccine or are not properly presented to the immune system.

Furthermore, local (mucosal, respiratory or enteric) protection was not effectively induced in birds vaccinated with the recombinants. This is a serious drawback since vaccines used for primary vaccination against respiratory diseases must induce local immunity to prevent infection and spread of virulent viruses that infect chickens reared under field conditions.

Antibodies against NDV which are capable of protecting the host can be measured in virus neutralization tests. However, since the neutralization response appears to parallel the haemagglutination inhibition (HI) response, the latter test is frequently used to assess the protective response, especially after vaccination.

Antibodies against both the F and HN proteins can neutralise NDV. However, antibodies against the F protein appear to induce greater neutralisation than those directed against HN in in vivo and in vitro tests (Meulemans et al., 1986).

The presence of specific antibodies to NDV in the serum of a bird gives little information on the infecting strain of NDV and therefore has limited diagnostic value.

The omnipresence of lentogenic NDV strains in birds in most countries and the almost universal use of live vaccines that cannot be distinguished, at least not serologically from wild-type NDV, means that the mere demonstration of infection is rarely adequate cause for control measures to be imposed. Since field disease may be an unreliable measure of the true virulence of the virus, it is necessary to further characterize the virus that is found.

At present, the only method of Newcastle disease diagnosis which allows characterization of the infecting strain, is virus isolation followed by pathogenicity testing. At present, three in vivo tests are used for this purpose: 1) mean death time (MDT) in eggs; 2) intracerebral pathogenicity index (ICPI) in one-day-old chickens; 3) Intravenous pathogenicity index (IVPI) in 6-week-old birds.

These tests suffer from a number of drawbacks, such as the availability of animals, poor reproducibility, and the relatively long duration of the tests. Last but not least, these tests do not allow a simple serological identification of poultry vaccinated with a vaccine or infected with a wild-type strain.

As an alternative to in vivo tests, the polymerase chain reaction (PCR) has been successfully used to distinguish between virulent and non-virulent i and non-virulent isolates (Stauber et al., 1995; Kant et al., 1997), however, again serological differentiation is not possible.

The raising of poultry and trade of their products is now organized on a international basis, frequently under management of multinational companies. The threat of Newcastle disease has proven a great restraint on such trade.

Successful control of Newcastle disease will only be approached when all countries report outbreaks. However, international agreements are not simple due to enormous variation in the extent of disease surveillance in different countries. Some countries do not vaccinate and would not want any form of NDV introduced in domestic poultry because vaccinated poultry cannot be distinguished from those infected with wild-type NDV.

Others only allow the use of specific live vaccines and consider other vaccines as unacceptably virulent. Yet other countries have the continued presence of circulating highly virulent virus, which is not recognised as such because overt disease is masked by vaccination.

In many countries legislation exists to control Newcastle disease outbreaks that may occur. National control measures are directed at prevention of introduction and spread. Most countries have restrictions on trade in poultry products, eggs, and live poultry. Most countries have established quarantine procedures for importation, especially for psittacine birds.

Some countries have adopted eradication policies with compulsory slaughter of infected birds, their contacts, and products. Others require prophylactic vaccination of birds even in the absence of outbreaks, while some have a policy of ring vaccination around outbreaks to establish a buffer zone.

Clearly, there is a need for better vaccines and for better diagnostic methods which can be used to control Newcastle disease. Due both to large differences in the dose that is received by individual birds during mass application of live vaccines and to variation in levels of maternal immunity in young chickens, post-vaccination reactions with live vaccines are inevitable. This is one of the main concerns of farmers in countries where vaccination is compulsory.

Furthermore, many vaccines are mixtures of subpopulations. When cloned, these sub-populations may differ significantly from each other in immunogenicity and pathogenicity (Hanson, 1988).

However, the largest drawback of currently used live vaccines and inactivated vaccines is the fact that vaccinated animals cannot be distinguished from infected animals with currently used screening techniques such as heamagglutination-inhibition or virus neutralization tests.

Virulent field-virus may still spread in vaccinated flocks since disease symptoms are masked by vaccination. Since virus isolation and characterization of virulence by in vivo techniques is not feasible on a large scale, there is a great need for new and effective attenuated live vaccines which can be serologically discriminated from field-viruses.

Such vaccines, called NDV marker vaccines (and accompanying diagnostic methods and kits) which should provide the fullest possible immunological spectre of antigenically relevant NDV epitopes, and yet should be serologically distinct from wild-type NDV are not yet available.

DISCLOSURE OF THE INVENTION

The invention provides a method to modify an avian-paramyxovirus genome by genetic modification, provides genetically modified avian-paramyxovirus and an avian-paramyxovirus marker vaccine.

The advent of modem molecular biological techniques has allowed the genetic modification of many RNA viruses, including negative-strand RNA viruses. This technique is often referred to as "reverse genetics". One first provides a (full-length) cDNA copy of the viral RNA, after which one transcribes this DNA in susceptible cells to produce infectious RNA which can again replicate to produce infectious virus particles.

In general, by previous modification of the cDNA with standard molecular biological techniques, it is possible to obtain a genetically modified RNA virus. However, this has never materialized for NDV or other avian-paramyxoviruses, it has even not yet been possible to generate minigenome fragments or plasmids of avian-paramyxovirus genomic fragments to study replicative events of avian-paramyxovirus, thereby creating an understanding on how to construct infectious copy virus.

Surprisingly, although in this description it has now been fully established that the genome of avian-paramyxovirus is the smallest of all paramyxovirus genomes sequenced up to now, especially the 5' terminal end sequence of the NDV genome is much longer than previously had been established and was expected by comparison with other Paramyxoviridae. The invention now for the first time provides a full sequence of an avian-Paramyxovirus genome and provides full-length or minigenomic length cDNA of such a virus.

The invention herewith provides avian-paramyxovirus cDNA at least comprising a nucleic acid sequence corresponding to the 5'-terminal end of the genome of avian-paramyxovirus allowing generating an infectious copy of avian-paramyxovirus, said cDNA preferably comprising a full-length cDNA. However, the invention also provides cDNA at least comprising a nucleic acid sequence corresponding to the 5'-terminal end of the genome of avian-paramyxovirus thereby allowing generating a replicating avian-paramyxovirus minigenome. Such minigenomes can advantageously be used to transcribe RNA and/or express protein from modified nucleic acid sequences. The invention provides a cDNA according to the invention at least partly derived from Newcastle Disease Virus, for example wherein said Newcastle Disease Virus is a lentogenic virus, preferably derived from a vaccine strain, such as LaSota strain ATCC VR-699.

The invention furthermore provides a cDNA according to the invention additionally provided with a modification, such as a deletion, insertion, mutation, reversion, or otherwise in a nucleic acid. For example a cDNA is provided wherein said modification comprises a nucleic acid encoding a modified protease cleavage site, for example wherein said cleavage site is a protease cleavage site of the fusion (F) protein.

In yet another embodiment, the invention provides a cDNA according to the invention wherein said modification comprises a nucleic acid encoding a hybrid viral protein, such as a hybrid hemaglutinin-neuraminidase (HN) protein as described in the experimental part of the invention. The invention also provides a cDNA according to the invention wherein said modification comprises a deletion in a nucleic acid encoding a viral protein, such as a matrix CM) protein.

The invention additionally provides a cDNA according to the invention additionally provided with a nucleic acid encoding an heterologous antigen, preferably wherein said antigen is derived from a poultry pathogen, as for example described below. An RNA, and protein derived thereof, obtained from a cDNA according to the invention is also provided.

In recent years, a number of non-segmented negative-strand RNA viruses has been fully characterized and fundamental work on the replication and expression of their genomes has culminated in the ability to generate infectious virus entirely by transfecting cells with cloned cDNA of said virus (reviewed by Conzelmann, 1996).

To date, infectious virus of non-segmented negative-strand RNA viruses has been generated from cloned cDNA of for example rabies virus (Schnell et al., 1994, Conzelmann; EP0702085A1). (Schnell et al., 1994; EP0702085A1), vesicular stomatitis virus (Lawson et al., 1995; Whelan et al., 1995), Sendai virus (Garcin et al., 1995), measles virus (Radecke et al., 1995; Schneider et al., 1997; EP0780475A1), human respiratory syncytial virus (Collins et al., 1995), rinderpest virus (Baron and Barrett, 1997), and human parainfluenza. virus type 3 (Hoffman and Banerjee, 1997, Conzelmann; P0702085A1), (Schnell et al., 1994; EP0702085A1).

However, all of above infectious copy viruses are capable of growing both in vivo as well as in vitro in hosts, tissues or cells of various origin, allowing easy cDNA transfection and replication and generation of infectious virus particles on a suitable cell line.

Such possibility does not exist for NDV certainly not for lentogenic NDV strains which can provide a vaccine. Virulence of such an NDV strain is associated with its ability to replicate in a wide range of cells, reflected by the fact that virulent strains can easily replicate in vitro and in vivo, whereas vaccine strains can only replicate in vivo.

Thus, with NDV a catch 22 situation is apparent. While attempts to generate an infectious copy virus from for example infectious cDNA may possibly result in infectious virus, such virus is in general not suitable for use as a vaccine because the thus generated infectious virus is by default too virulent to be used as vaccine; the fact that it can be generated and replicated after transfection of cDNA on a cell line reflects its easy cleavability of the Fo protein into F1 and F2, as discussed above a hallmark of virulence of a NDV.

Using a vaccine strain as parent material for the cDNA would not solve this problem; a vaccine strain, especially of a lentogenic type does not contain an easily cleavable Fo protein, rendering it impossible for first generation virus to continue to replicate. The cell used for transfection will simply not be susceptible to support one or more rounds of replication of vaccine-type virus with a non-cleaved Fo protein.

The invention now elegantly provides a solution for this problem, and therewith provides infectious copy NDV, for example for use in a vaccine.

The invention provides a method to generate infectious copy Newcastle Disease Virus comprising transfecting cells, capable of expressing viral NP, P and L proteins for complexing with viral RNA with cloned full-length or genomiclength cDNA of said virus and further comprising incubating said cells in growth medium comprising proteolytic activity allowing cleavage of the Fo protein of said virus.

In our system, co-transfection of a plasmid expressing NP could be omitted. NP is probably expressed from the full length cDNA because the NP gene is the first gene after the 5' end of the antigenomic RNA. Since eukaryotic mRNA's are usually monocistronic, expression of distal genes is not expected. However it is possible to generate full-length cDNA in which the relative positions of the NDV genes are changed. If the first gene of such a cDNA is the P or L gene, it is not necessary to express the corresponding gene product from a co-transfected plasmid.

As an alternative to using full-length cDNA, it is possible to use two or more subgenomic cDNA's which generate replication competent subgenomic cDNA's and which together express the full complement of avianparamixovirus proteins. Even if the RNA's are packaged separately, the resulting virus-like particles can be used for successive rounds of replication by means of co-infection and complementation of gene functions.

In a preferred embodiment, the invention provides a method wherein said proteolytic activity is derived of an enzyme, such as a trypsin-like enzyme, or is derived of a composition comprising said proteolytic activity. In a much preferred embodiment, said growth medium comprises allantoic fluid comprising proteolytic activity. Cleavage of the Fo protein is required for the generation of infectious virus. It is possible to generate infectious virus from lentogenic strain without the addition of exogenous proteolytic activity. By inoculating the supernatant of transfected cells into the allantoic cavity of embryonated eggs, the proteolytic activity which is present in the allantoic fluid is able to cleave the Fo protein to generate the fusion competent F1–F2 complex. Virions with such an activated F protein are able to infect susceptible cells and replication in cells which express the desired proteolytic activity yields infectious progeny. As an alternative to providing the desired proteolytic activity to the supernatant of transfected cells, it is for example possibe to use a cell that is permissive for NDV and which already expresses said proteolytic activity. Such a cell line is used to produce infectious lentogenic NDV without the addition of exogenous proteolytic activity. Such a cell line can also be generated by stable transfecting a cell line with a gene that specifies said activity. Furthermore, it is possible to generate a stable transfected cell line that expresses the wild-type F protein in the virus envelope, thereby providing infectious particles (themselves not provided with genomic information encoding wild-type F protein) with means to enter a cell. Rescue of infectious lentogenic virus is also possible by infection of transfected cells with an NDV helpervirus. An essential requirement for such a helpervirus would be that it can be selected against, for instance by means of neutralizing antibodies which eliminate the helpervirus but which do not react with the lentogenic virus.

Finally, one may construct a stably transfected cell line that expresses one, two, or all of the three essential NDV proteins, NP, P, and L. Such cell lines require the coexpression of only a subset of the three essential proteins or no co-expression at all for supporting generating infectious copy virus.

In a preferred embodiment, the invention provides a method wherein said cells used for transfecting are derived of chicken primary or secondary cells or cell-lines. The description provides for example CER or CEF cells, which, as most in vitro cells in general, lack the appropriate proteases which are required to cleave the Fo protein of NDV, for example of strain LaSota. However, cells derived from for example other birds can also be used.

The invention further provides a method to generate infectious copy Newcastle Disease Virus comprising transfecting cells with cloned full-length or genomic-length cDNA of said virus as for example identified in FIG. 3 and further comprising incubating said cells in growth medium comprising proteolytic activity allowing cleavage of the Fo protein of said virus, further comprising recovering infectious virus by culturing said cells and innoculating material derived from said cultured cells into the allantoic cavity of embryonated eggs. Said material for example comprises (harvested or freeze-thawed) cells or cell debris or supernatant derived from said cell culture.

For example, the description describes a method to recover infectious virus, wherein the supernatant of transfected CEF monolayers was inoculated into the allantoic cavity of embryonated eggs. Four days later the allantoic fluid was harvested, analyzed in a haemagglutination assay, and passaged further in eggs.

In addition, the invention provides a method further comprising passaging said infectious copy Newcastle Disease Virus by harvesting allantoic fluid and re-inoculating embryonated eggs.

In a preferred embodiment of the invention, a method is provided wherein said virus is a lentogenic virus, for example derived from an avirulent field-case of NDV or from a vaccine strain of NDV, such as the LaSota strain of NDV. Furthermore, a method is provided to modify an avianparamyxovirus genome by means of genetic modification which allows the introduction of one or more mutations, deletions, and/or insertions or other modifications. For example, method is provided to attenuate or modify the virulence of avian-paramyxovirus by modifing cDNA, for example encoding a viral protein, such as the V protein, and cloning said modified cDNA into full-length cDNA and generating infectious copy virus from said fulllength cDNA, thereby generating new NDV strains or new attenuated live vaccines with improved properties.

Apart from attenuation by modification of gene products it is also possible to attenuate avian-paramyxovirus by modification of nucleotide sequences which are involved in transcription and/or replication. Such modifications result in attenuated strains which express wild type like F proteins which are cleavable both in vitro and in vivo in a wide range of cells and as a result are more immunogenic than the classical vaccine strains.

In a preferred embodiment, the invention provides a method to attenuate or modify the virulence of an avian paramyxovirus such as a Newcastle Disease Virus, comprising modifying a protease cleavage site of a viral protein by modifying cDNA encoding said cleavage site, further comprising cloning said cDNA into genomic length cDNA of e.g. Newcastle Disease Virus and generating infectious copy Newcastle Disease Virus. Said cleavage site is for example a protease cleavage site in the F or HN protein of Newcastle Disease Virus. Attenuation is in general restricted to reduction of virulence, however, it is now also possible to use a relatively a-virulent strain of NDV and provide the progeny of such a strain with increased virulence, for example by providing it with an increased tendency to replicate in a specified cell-type. It is now thus possible to assign distinct virulence attributes to NDV.

The invention provides a method to antigenically modify avian paranlyxovirus such as a Newcastle Disease Virus, comprising modifying cDNA encoding at least a part of a viral protein harboring at least one immunodominant epitope, further comprising cloning said cDNA into genomic length cDNA of Newcastle disease virus and generating infectious copy Newcastle Disease virus.

For example, the invention provides a method to (further) modify NDV, for example using a method to produce an infectious copy of NDV (vaccine) which has been provided, a method to produce a recombinant marker NDV vaccine is provided, a marker vaccine that contains the fullest possible or needed immunological spectrum of antigenically relevant NDV epitopes, and yet is serologically distinct from wild-type NDV because a distinct, serologically relevant epitope or marker has been removed by recombinant techniques. The invention provides a method to modify the antigenic make-up of avian paramyxovirus such as NDV, thus allowing the generation of e.g a live NDV marker vaccine which can be serologically distinguished from avian paramyxovirus field strains.

In one embodiment, the invention provides infectious copy NDV wherein the HN protein of NDV has been modified by recombining cDNA encoding a part of said HN protein with cDNA encoding a part of HN protein derived from an avian-paramyxovirus, for example type 2 or type 4. Said hybrid hn protein serves as a serological marker for the infectious copy NDV strain thus obtained or can serve to change the tropism of the avian paramyxovirus to other cells and/or tissues. These, so called, marker strains as provided by the invention allow the generation of vaccines which are an invaluable tool to assess the prevalence of NDV in commercial flocks around the world. Furthermore, the large-scale application of such marker vaccines will lead to the complete eradication of NDV by a process of intensive screening and stamping out of infected flocks.

Furthermore, a method is provided to generate an infectious copy NDV strain which expresses one or more antigens from other pathogens and which can be used to vaccinate against multiple diseases. Such an infectious copy NDV virus for example comprises a heterologous cDNA encoding a heterologous protein obtained from for example Avian Influenza (AI) (Haemagglutinim (H5 and H7) and Neuraminidase), Avian leukosis virus (ALV) (env protein (gp85)), Chicken anemia virus (CAV) (VP1+VP2), Marek's disease virus (MDV) (glycoprotein B (gB), gH), Infectious laringotracheitis virus (ILT) (gB, gH, gD), Infectious bursal disease virus (IBDV) (VP2 and VP3), Turkey rhinotracheitis virus (TRT) (fusion (F) protein), Avian paramyxovirus-2,-3,-6 (PMV) (F-protein, Haemagglutinin neuraminidase (HN), or others, Infectious bronchitis virus (IBV) (peplomer protein, nucleoprotein), Reoviruses (sigma protein), Adenoviruses Pneumoviruses, *Salmonella enteritidis, Campylobacter jejuni, Escherichia coli, Bordetelia avium* (formerly *Alcaligenes faecalis*), *Haemphilus paragallinarum, Pasteurella multocida, Ornithobacterium rhinotracheale, Riemerella* (formerly Pasteurella) *anatipestifer*, Mycoplasmata (*M. gallisepticum, M synoviae, M. mereagridis, M. iowae*), or Aspergilli (*A. flavus, A. fumigatus*).

The invention herewith provides avian-paramyxovirus or strains derived thereof which can be used as a vaccine vector for the expression of antigens from other poultry pathogens. Several properties make NDV an ideal vaccine vector for vaccination against respiratory or intestinal diseases. 1) NDV can be easily cultured to very high titres in embryonated eggs. 2) Mass culture of NDV in embryonated eggs is relatively cheap. 3) NDV vaccines are relatively stable and can be simply administered by mass application methods such as by drinking water or by spraying or aerosol formation. 4) The natural route of infection of NDV is by the respiratory and/or intestinal tract which are also the major natural routes of infection of many other poultry pathogens. 5) NDV can induce local immunity despite the presence of circulating maternal antibody.

It has been shown that NDV has potent antineoplastic, as well as immune-stimulating properties (for a review see Schirrmacher et al., 1998) [Schirrmacher, V., Ahlert, T., Steiner, H.-H., Herold-Mende, C., Gerhards, R. and Hagm üllen E. (1998) Immunization with virus-modified tumor cells. *Seminars in Oncology* 25: 677–696]. Although NDV does not seem to be able to replicate productively in normal human cells, a selective NDV-mediated killing of human cancer cells was noted. After local NDV therapy, viral oncolysis and complete remissions of human tumor xenografts were observed in nude mice. This has led to the use of NDV for tumor therapy. However, a problem is that such application may be restricted to local treatment.

NDV infection induces interferons, chemokines, and other potentially important gene products, and introduces pleiotropic immune-stimulatory properties into tumor cells. This concept has been used for the production of autologous tumor cell vaccines consisting of fresh operative specimens that have been infected with NDV. This type of vaccine is called autologous tumor vaccine-NDV or ATV-NDV (Schirrmacher et al., 1998). The NDV-infected cells are inactivated by gamma-irradiation which prevents cell division but which still allows replication of NDV in the cytoplasm of infected cells. After inoculation of patients with ATV-NDV, T-cells are recruited through NDV-induced chemokines. Some of these T-cells may express a T-cell receptor that can interact with peptides from tumor-associated antigens in complex with major histocompatibility complex class I molecules at the cell surface. This interaction results in the induction of a cytotoxic T-cell response which results in specific killing of autologous tumor cells.

The invention provides that the repertoire and amount of chemokines and immune stimulatory proteins induced by NDV infection are modulated. The present invention provides a method for generating recombinant NDV that has been modified to incorporate and express (a) heterologous gene(s). Such recombinant NDV may be used to modify the repertoire and amount of immune-stimulatory proteins in infected cells. In one embodiment, the invention provides a recombinant NDV that incorporates and expresses genes encoding human interferons, chemokines or other immune stimulatory proteins. Said recombinant NDV is used for the production of ATV-NDV which is more potent than conventional ATV-NDV. For example: cytokines IFN-α, -β, TNF-α, IL-1, IL-6; chemokines RANTES, IP-10; other genes such as HSP, ACTH, endorphin, iNOS, EPA/TIMP, NFkB.) The pleiotropic immune-stimulatory properties of NDV may also be used as an adjuvant for vaccination of animals and humans against infectious diseases. In one embodiment of the invention, foreign genes encoding (a) relevant antigen(s) of (an) infectious agent(s) are introduced in the NDV genome and the simultaneous expression of the antigen(s) and the immune-stimulatory proteins by infected cells may induce a potent immune response against the infectious agent. In another embodiment of the invention, the immune-stimulating properties of NDV may be further enhanced by using NDV recombinants that simultaneously express antigens and specific immunestimulatory proteins. In a preferred embodiment, the invention is used to generate an AIDS (acquired immune-deficiency syndrome) vaccine by using NDV recombinants that express relevant antigens of human immune-deficiency virus HIV), either alone or in combination with immune-stimulatory proteins.

NDV are also used as an adjuvant for vaccination of animals and humans against infectious diseases. In one embodiment of the invention, heterologous or foreign genes encoding (a) relevant antigen(s) of (an) infectious agent(s) are introduced in the NDV genome and the simultaneous expression of the antigen(s) and the immune-stimulatory proteins by infected cells may induce a potent immune response against the infectious agent. In another embodiment of the invention, the immune-stimulating properties of NDV are further enhanced by using NDV recombinants that simultaneously express antigens and specific immune-stimulatory proteins. In a preferred embodiment, the invention is used to generate an AIDS (acquired immune-deficiency syndrome) vaccine by using NDV recombinants that express relevant antigens of human immune-deficiency virus (HIV), either alone or in combination with immune-stimulatory proteins.

Also, a method is provided to generate a conditional lethal NDV deletion mutant which can be used as self-restricted non-transmissible (carrier) vaccine. An NDV deletion mutant was generated which is unable to express the matrix (M) protein which is involved in budding of NDV at the inner cell membrane. The invention provides for example a phenotypically complemented NDV strain that is unable to express the M protein which is still able to infect cells and spread by means of cell-to-cell transmission. However, the mutant virus is unable to generate infectious progeny on non-complementing cells. This shows that phenotypically complemented NDV deletion mutants can be used as safe self-restricted vaccines which are unable to spread into the environment. Such a non-transmissible vaccine combines the most important advantage of live vaccines, i.e., efficacy, with the most important advantage of killed vaccines, i.e., safety.

The invention provides Newcastle Disease Virus, or strains derived thereof, for example by passaging or further cultivation in embryonated eggs or appropriate cells, that is derived from infectious copy virus obtainable by a method provided by the invention.

For example, NDV is provided that has been modified in at least one way to generate infectious copy Newcastle Disease Virus which is attenuated, modified in virulence, antigenically modified, expressing a heterologous antigen or are non-transmissible, or combinations thereof.

Herewith the invention provides NDV vaccines, characterised for example by carrying distinct virulence attributes or distinct antigenic characteristics, be it for marker vaccine purposes and/or for expressing heterologous antigens derived from other pathogens, be it in transmissible and/or non-transmissible form.

Such a vaccine can be a killed or a live vaccine, preferably, such a vaccine is a live vaccine, however, killed vaccines as provided by the invention are beneficial under those circumstances where a live vaccine is not or only little applicable, for example because of trade restrictions or other conditions set by disease controlling authorities.

The invention herewith also provides a diagnostic method, and corresponding test kit, to detect antibodies against said serologically relevant immunodominant epitope or marker, therewith providing methods and means to execute a method for control and/or eradication of NDV and/or other poultry diseases in poultry. The invention provides new and effective vaccines which can be serologically discriminated from field-viruses and old-type vaccines. Such new vaccines, called NDV marker vaccines, provide the fullest possible immunological spectrum of antigenically relevant NDV epitopes, and yet are serologically distinct from wild-type NDV by applying accompanying diagnostic methods and kits.

The invention provides a method for distinguishing unvaccinated animals or animals vaccinated with a NDV vaccine according to the invention from animals infected with wild-type NDV or vaccinated with an unmodified mesogenic or lentogenic NDV-vaccine strain comprising taking a least one sample (such as serum, blood, eggs or eye fluid) from said animal and determining in said sample the presence of antibodies directed against an immunodominant epitope or marker expressed by said wild-type or unmodified NDV but not by a vaccine according to the invention.

The invention provides a method wherein said antibodies are directed against the HN or F protein of NDV, for example a hybrid protein as described in the experimental part as this description. The invention provides for example a diagnostic method wherein said animal is selected from the group composed of poultry, preferably of chickens.

The invention also provides a diagnostic kit for use in a method to serologically distinguish between animals. In one embodiment of the invention, a simple and rapid haemagglutination-inhibition (HI) test is used to distinguish between vaccinated animals and infected animals. Animals vaccinated with a marker vaccine in which the complete globular head of HN of NDV has been replaced with the corresponding part of HN of another serotype will not induce antibodies to HN of NDV and therefore will not inhibit haemagglutination of erythrocytes by NDV visions.

By using marker vaccine virions in the HI test, antibodies against the hybrid HN protein is detected and may used as a measure for the efficacy of vaccination. As an alternative, an ELISA that detects antibodies against the F protein of NDV is used to measure the efficacy of vaccination.

Apart from the HI test, an ELISA can be used to determine the presence of antibodies against HN of NDV. The antigen to be used in such a test is for example HN of NDV that is expressed by recombinant DNA techniques or a conserved peptide from HN of NDV.

A blocking ELISA may also be used. In this case one or more monoclonal antibodies against conserved epitopes of HN of NDV are used to determine whether competing antibodies are present in samples from vaccinated animals. The ELISA tests can advantageously be used if the marker vaccine contains a chimeric HN protein only or when a few epitopes of HN of NDV are replaced.

The invention is further explained in the experimental part of this description without limiting the invention thereto.

DESCRIPTION OF THE FIGURES

FIG. 1) and contain the 3'-region (nt 1–119) and 5'-region (nt 14970–15186) of NDV strain LaSota flanking the gene encoding secreted alkaline phosphatase (SEAP). Transcription of pOLTV535 by T7 RNA polymerase yields antigenomic RNA (or ([+]-RNA) whereas transcription of pOLTV553 yields genomic RNA (or [-]-RNA). The start (S) and end (E) boxes, which are viral transcription initiation and termination signals, are indicated. The start codon of the SEAP gene is underlined. The sequences of the insertions (N0–N5) in the ClaI-site which generate minigenome plasmids which each differ 1 nt in length (pOLTV535N0–N5 and pOLTV553N0–N5, respectively) are also shown.

FIG. 3. Nucleotide sequence of the genome of NDV strain LaSota and deduced amino acid sequence of the NDV genes. The sequence shown corresponds to the antigenomic strand and is shown in the 5' to 3' direction in the form of ssDNA. The sequence shown in this figure is that of the consensus sequence which was determined by completely sequencing two independent sets of overlapping subgenomic cDNA's which span the entire NDV genome. Remaining ambiguities (probably as a result of PCR errors) were resolved by sequencing relevant regions of a third independent set of clones.

The sequence of the full length cDNA clone pNDFL+ which was assembled from overlapping subgenomic cDNA clones (see FIG. 4), differs from that of the consensus NDV sequence at the following positions (consensus sequence between parentheses): nt 1755, G (A); nt 3766, A (G); nt 5109, G (A); nt 6999, T (C); nt 7056, G (A); nt 9337, G (A); nt 9486, A (T); nt 10195, T (C); nt 13075, A (G). These differences results in 3 amino acid changes (consencus sequence between parentheses): F protein, $R^{189}$ (Q); HN protein $S^{200}$ (P) L-protein $N^{369}$ (I).

Figure 4A:
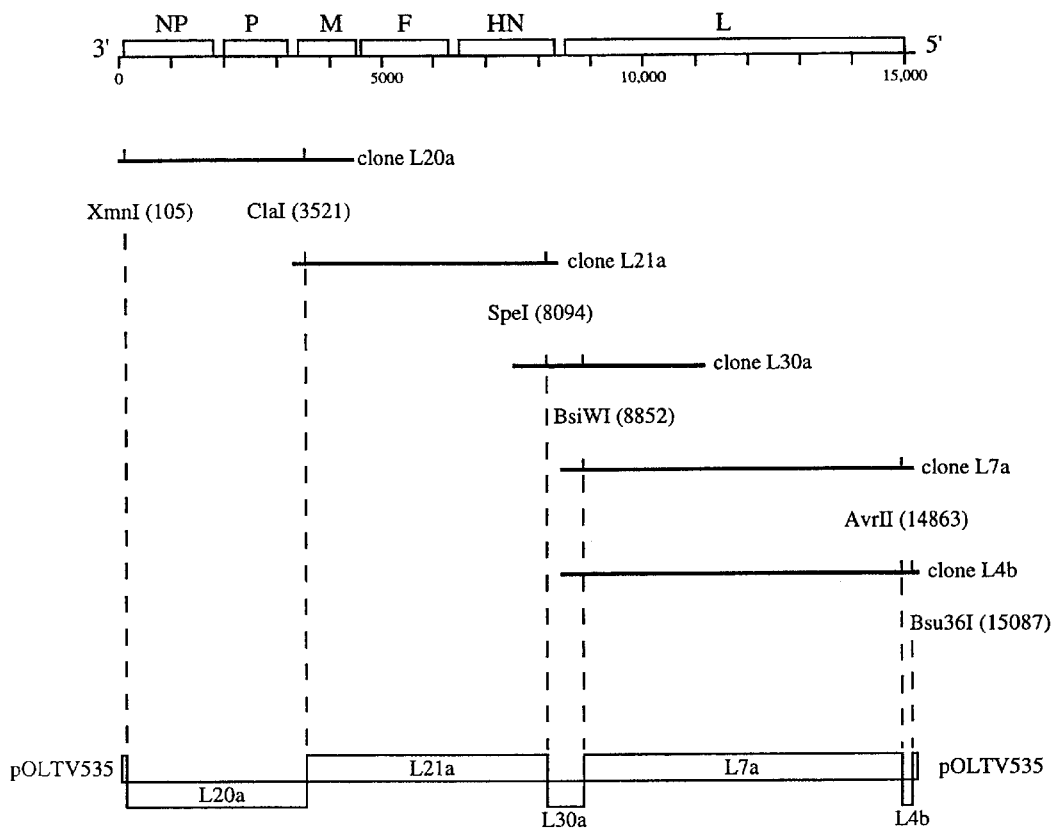
Figure 4C:
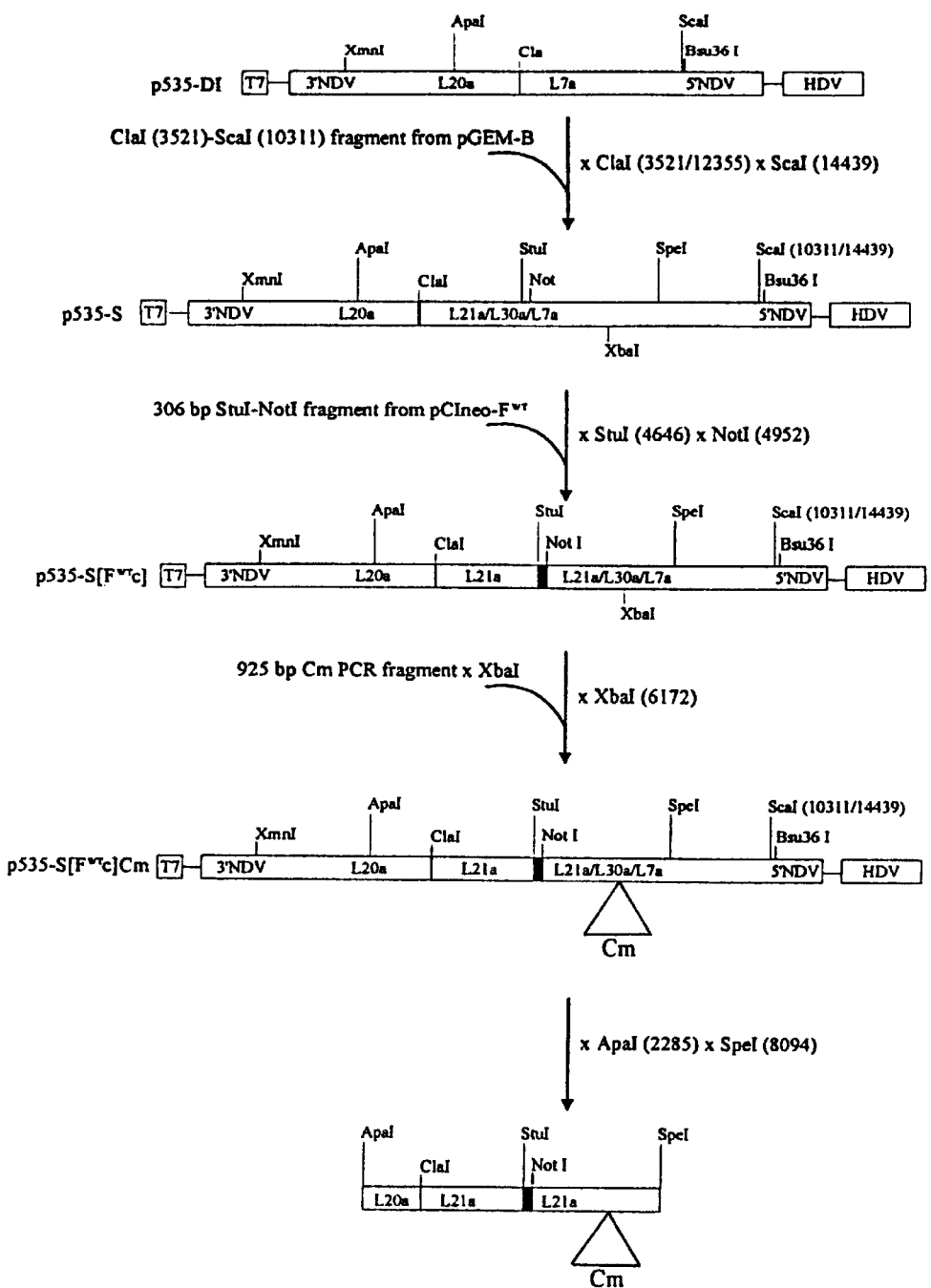

FIG. 4. Portion (A) Overall strategy used for the assembly of the full-length NDV cDNA from subgenomic overlapping cDNA clones. The cDNA was assembled in plasmid pOLTV535 which already contained the 3' and 5' ends of NDV strain LaSota (cf. FIG. 2). The resulting plasmid, designated pNDFL+, was used for the generation of infectious NDV.

Portion (B) Detailed cloning procedure for the assembly of the fulllength NDV cDNA from subgenomic overlapping cDNA clones. Cm denotes the chloramphenicol-resistance gene which was temporarily introduced as a phenotypical tag (see text for details).

Portion (C) Detailed cloning procedure for the generation of genetically modified full-length NDV cDNA. The modification consists of 3 nucleotide changes which were introduced in the F gene and which result in the modification of the amino acid sequence of the proteolytic cleavage site of the F protein (see text for details).

Figure 5A:
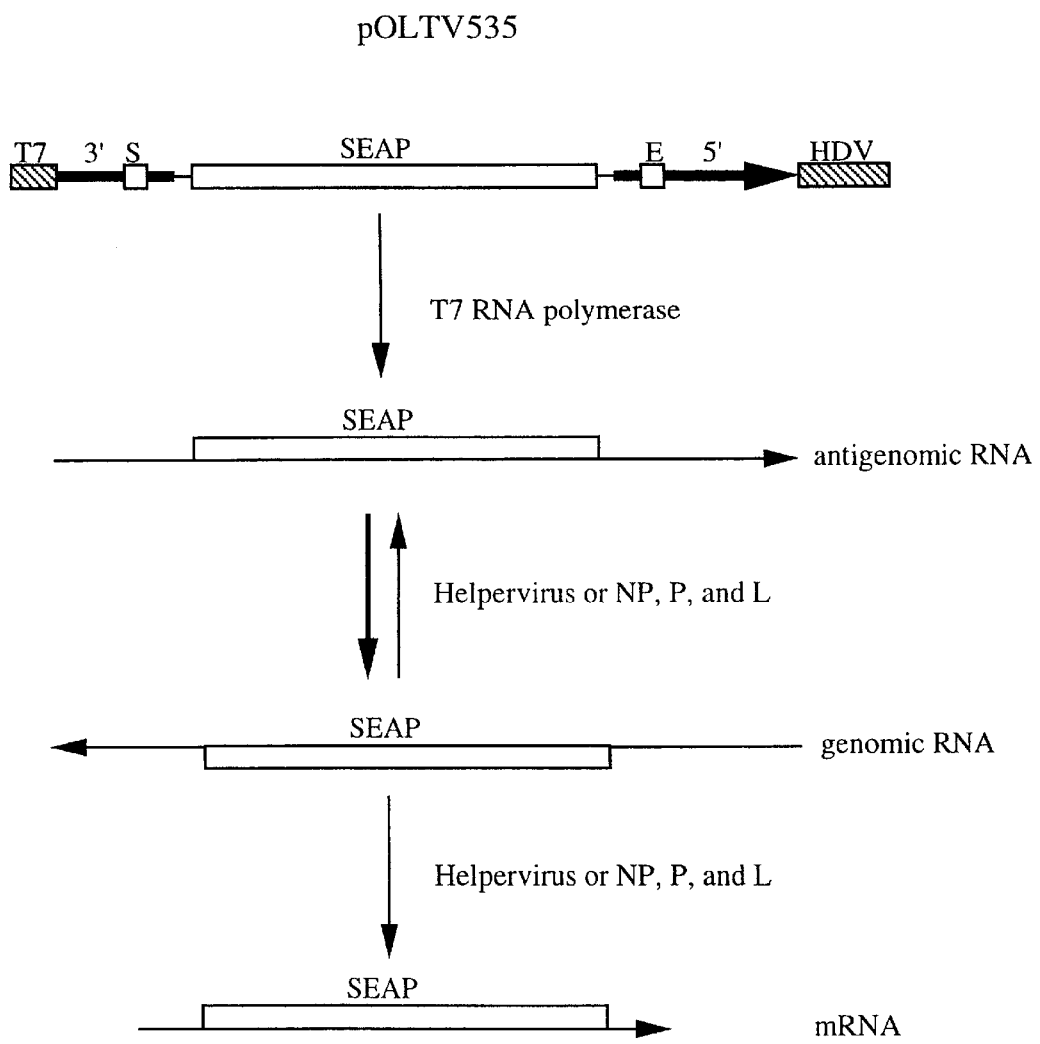
Figure 5B:
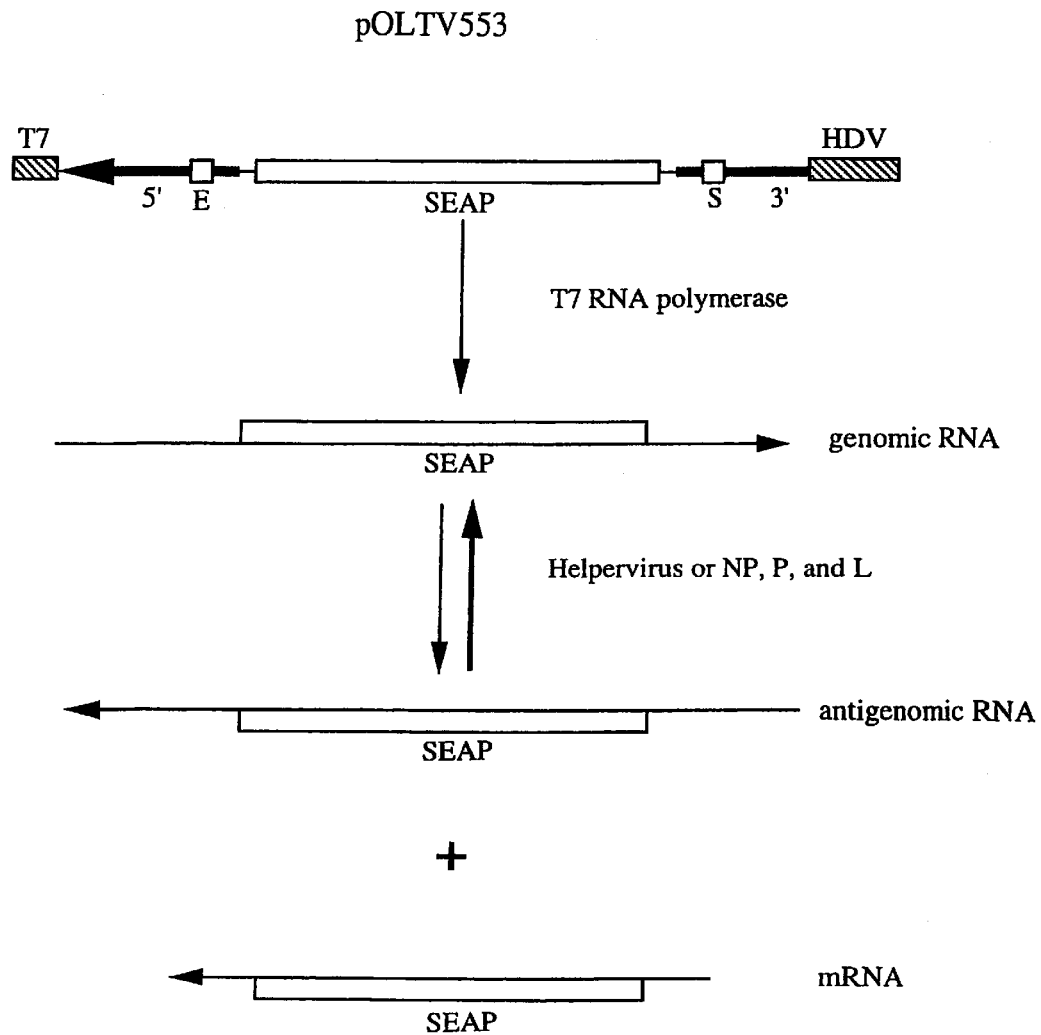

FIG. 5. Portion (A) pOLTV535-series. Transcription by means of T7 RNA polymerase yields antigenomic RNA (or [+]-RNA) which can be directly translated into SEAP protein by the cell. After infection of cells by helpervirus (or after co-transfection of plasmids encoding NP, P, and L), the antigenomic RNA is used by the viral polymerase complex for the synthesis of genomic RNA (or [-]-RNA). The genomic RNA is then used by the viral polymerase complex for the synthesis of both mRNA (by using the specific transcription start [S] and end [E] boxes) and antigenomic RNA.

Portion (B) pOLTV553-series. Transcription by means of T7 RNA polymerase yields genomic RNA (or [-]-RNA) which cannot be translated into SEAP protein. After infection of cells by helpervirus (or after co-transfection of plasmids encoding NP, P. and L), the genomic RNA is used by the viral polymerase complex for the synthesis of both mRNA (by using the specific transcription start [S] and end [E] boxes) and antigenomic RNA.

FIG. 6. Alignment of nucleic acid sequences 5' terminal ends of NDV LaSota and other paramyxoviruses are given as sequence comparison of NDV across the four members of the Rubulavirus genus, three members of the Paramyxovirus genus, and three members of the Morbillivirus genus. The sequences are presented from the L gene end box to the 5' end (3'-5' cDNA).

NDV, new castle disease virus (SEQ ID NO:143); hPIV2, human parainfluenza virus 2 (SEQ ID NO:144); MuV, mumps virus (SEQ ID NO:145); SV5 (SEQ ID NO: 147) and SV41 (SEQ ID NO:146), simian virus 5 and 41 respectively; SeV, sendai virus (SEQ ID NO:140); bPIV3 (SEQ ID NO: 140), and hPIV3 (SEQ ID NO:141) bovine and human parainfluenza virus respectively CDV, canine distemper virus (SEQ ID NO: 137); MeV measles virus (SEQ ID NO: 138), RPV, rinderpest virus (SEQ ID NO: 139). Nucleotide (nt) sequences of the entire genomes were obtained as follows (accession no.): NDV (AF077761h hPIV2 (X57559); MuV(AB000388); SV5 (AF052755); SV41 (X64 275); bPIV3 (D84 095); hPIV3(Z1157[5]) CDV(L13194); MeV(X16565); RPV(Z30697).

BEST MODE OF THE INVENTION

Experimental Part

Materials and Methods

Standard cloning procedures were carried out according to Sambrook et al. (1989) unless stated otherwise. All constructions involving DNA fragments which were generated—by means of the polymerase chain reaction (PCR) were verified by sequence analysis. In the primer sequences given below, the underlined nucleotides correspond to NDV sequences and the position within the NDV genome is indicated. The nucleotide sequence of restriction sites which were used for cloning are indicated in boldface.

Cells and Viruses

CER cells (Smith et al., 1976) were grown in GMEM/EMEM (1:1) containing 5% foetal calf serum and 2% of an antibiotic mix that contained 1000 U/ml Penicillin, 1000 µg/ml Streptamycin, 20 µg/ml Fungizone, 500 µg/ml Polymixin B, and 10 mg/ml Kanamycin. QT35 cells (Moscovici et al., 1977; Cho, 1982) were grown in medium supplied by GibcoBRL/Life Technologies (cat.no. 041-91536; proprietary composition of Fort Dodge) supplemented with 5% FCS and 2% antibiotic mix. QM5 cells (Antin and Ordahl, 1991) were grown in M199 medium supplemented with 10% tryptose phosphate broth, 10% FCS and 2% antibiotic mix.

NDV strain LaSota was obtained from ATCC (ATCC VR-699) and was passaged two times in embryonated eggs. Before we started with the construction and cloning of cDNA, the virus was plaque purified by three rounds of plaque purification on primary chicken embryo fibroblasts (CEF). To this end the virus was titrated on CEF cells cultured in GMEM/EMEM (1:1) containing 5% foetal calf serum, 2% antibiotic mix, 5% allantoic fluid, 30 mM $MgCl_2$, 200 µg/ml DEAE-dextran (Sigma) and 0.8% agar Nobel (Difco). Virus from the third round of plaque purification (designated clone E13-1) was grown in embryoflated eggs and four days after inoculation the allantoic fluid was harvested and stored in aliquots at −70° C. The fowlpox recombinant virus fpEFLT7pol (Britton et al., 1996; hereafter called FPV-T7), which expresses T7 RNA polymerase, was a kind gift of Dr. Michael Skinner and was grown on QT35 cells.

Isolation of Viral RNA

All manipulations were carried out in RNase-free glassware or plastics and all solutions were made up with RNase-free water which was treated with 1% diethylpyrocarbonate (DEPC) and sterilized by autoclaving. Virus was pelleted from allantoic fluid by centrifugation at 21,000 rpm for 70 min in a Beckman SW4O rotor at 40° C. The pellet was resuspended in homogenization buffer (50 mM TrisHCl pH 7.5, 50 mM NaCl, 5 mM EDTA, 0.5% SDS) and treated with Proteinase K (200 µg/mil) for 90 min at 37° C. during constant agitation. The lysate was extracted two times with an equal volume of phenol/chloroform (1:1) pH 5.4 and once with an equal volume of chloroform. The viral RNA was precipitated from the aquous phase by the addition of 0.1 volume of 3M NaOAc pH 5.3 and 2.5 volumes of 100% ethanol. The precipitate was collected by centrifugation, washed once with 70% ethanol, resuspended in water, and stored in aliquots at −70° C.

Reverse Transcription

Viral RNA (1.5 µg) was mixed with 500 ng of primer in a volume of 12 µl and incubated for 10 min at 70° C. Four µl of 5×RT buffer (250 mM Tris-HCl, pH 8.3, 375 mM KCl, 15 mM $MgCl_2$; GibcoBRL/Life Technologies), 2 µl 0.1M DTT and 2 µl 10 mM dNTP's (2.5 mM each) was added and the mixture was incubated for 2 min at 42° C. Reverse transcription was performed in a final volume of 20 µl by the addition of 200 Units of reverse transcriptase (Superscript II; GibcoBRL/Life Technologies) followed by incubation for 60 min at 42° C.

Polymerase Chain Reaction (PCR)

All PCR reactions which were used to determine the 3' and 5' end of the NDV genome (see below) were carried out by using Tag DNA Polymerase (Perkin Elmer). For the cloning of individual NDV genes or large subgenomic cDNA's, either the proofreading DNA polymerase Pwo, or mixtures of Tag and Pwo (Expand High Fidelity Kit or Expand Long Template Kit) were used according to the instructions of the supplier (Boehringer Mannheim). All samples were incubated for 2 min at 94° C. before the start of the indicated number of PCR cycles. After the indicated number of PCR cycles, the samples were incubated at the elongation temperature for at least 3× the duration of the elongation time of the PCR cycle. PCR fragments were purified directly by using the High Pure PCR Product purification Kit (Boehringer Mannheim) or after agarose gelelectrophoresis by using the Qiaexll extraction kit (Qiagen) essentially as described by the suppliers.

Sequence Analysis

All sequences were determined by using the PRISM Ready Reaction Dye Deoxy Terminator Cycle Sequencing Kit (Perkin Elmer). Reaction mixtures (5 μl) were subjected to 25 cycles of linear amplification (10 sec at 94° C., 5 sec at 50° C., and 4 min at 60° C.) in a GeneArnp2400 thermocycler. Subsequently, the reaction mixtures were precipitated with ethanol, washed once with 70% ethanol, resuspended in 15 pl TSR buffer (Perkin Elmer) and heated for 2 min at 94° C. before being loaded on an Applied Biosystems AB31O automatic sequencer.

The nucleotide sequences of the primers which were used to sequence the complete genome of NDV strain LaSota were either derived from published sequences or from sequences established during this sequencing project. The primers are shown in Table 1.

Cloning and Sequencing of the 3' and 5' Termini of the Genome of NDV Strain LaSota The nucleotide sequence of the 3' and 5' termini of the NDV genome were determined by using RACE procedures (rapid amplification of cDNA ends). NDV RNA was used in a reverse transcription reaction in a final volume of 20 μl by using primer p360 (5'-<u>GGCGATGTAATCAGCCTAGTGCTT</u>-3' (SEQ ID NO: 47) nt 14756–14779) which was derived from the published sequence of the L-gene of NDV (Yusoff et al., 1987). The single-stranded cDNA (2.5 pl of the RT mixture) was added to 8 pmol anchorprimer ALG3 (5' CACGAATTCACTATCGATTCTGGATCCTTC-3' (SEQ ID NO: 83)) and ligated overnight at room temperature in 20 μl of a reaction mixture containing 50 mM Tris-HCl, pH 8.0, 10 mM $MgCl_2$, 10 μl/ml BSA, 25% PEG, 1 mM HCC, 20 uM ATP and 10 units of T4 RNA ligase (New England Biolabs) as described by Tessier et al. (1986). One μl of the ligation reaction was used as template in a PCR reaction by using primers p375 (5'-CAATGAAT<u>TCAAAGGATATTACAGTAACT</u>-3'; (SEQ ID NO: 84) nt 14964–14983) and ALG4 (5'-GAAGGATCCAGAATCGATAG-3' (SEQ ID NO: 85)). The latter primer is complementary to anchorprimer ALG3 (SEQ ID NO: 83). The PCR conditions (40 cycles) were as follows: 1 min at 94° C., 1 min at 55° C., and 2 min at 72° C. The PCR products were purified and cloned in T-vector pBluescriptII-TSK (Ichihara and Kurosawa, 1993). Alternatively, the purified PCR products were treated with Klenow DNA polymerase I to create blunt ends and cloned in the HindIII-site of plasmid pGEM4Z (Promega). Thirteen independent clones (8×pBleuscriptII-TSK and 5×pGEM4Z) were sequenced to determine the nucleotide sequence of the 5' end of the genome of NDV strain LaSota. The nucleotide sequence of the 3' end was determined by two independent methods. In method I, primer ALG3 (SEQ ID NO: 83) was ligated to the 3' end of the viral RNA by using T4 RNA ligase as described by Schütze et al. (1995). The reaction mixture (final volume 10 μl) contained 2.5 μg NDV RNA, 100 pmol ALG3 (SEQ ID NO: 83), 1 μl 1O×T4 RNA ligase buffer (500 mM Tris-HCl, pH 7.8, 100 mM $MgCl_2$, 100 mM DTT, 10 mM ATP), 1 μl DMSO, 1 μl 10 uM hexaminecobaltchloride, 1 μl RNasin (Promega) and 10 units of T4 RNA ligase (New England Biolabs). The mixture was incubated overnight at room temperature and 5 µl of the ligation reaction was used as template in a reverse transcription reaction by using ALG4 (SEQ ID NO: 85) as primer. One µl of the RT-reaction was used in a PCR reaction by using primers ALG4 (SEQ ID NO: 85) and p376 (5' GAGCCTTA AGGAGCTGCTCGTACTGATC 3'; (SEQ ID NO: 86) nt 137–164) which was from the published sequence of the 3'end of NDV (Ishida et al., 1986). The PCR conditions were as described above for the 5' RACE. In method II, the 3' and 5' ends of the viral NDV RNA were ligated to each other by using T4 RNA ligase using the same conditions as described above for method I. Five µl of the ligation mixture was used as template in a reverse transcription reaction by using primer p360 (SEQ ID NO: 47). One µl of the RT-reaction was used in a PCR reaction by using primers p375 (SEQ ID NO: 84) and p376 (SEQ ID NO: 86) and PCR conditions described above for the 5' RACE. The PCR products were treated with Klenow DNA polymerase I to create blunt ends and cloned in the HindII-site of plasmid pGEM4Z (Promega). Ten independent clones (4 from method I and 6 from method II) were sequenced to determine the nucleotide sequence of the 3' end of the genome of NDV strain LaSota.

Construction of Transcription Vector

Figure 1:
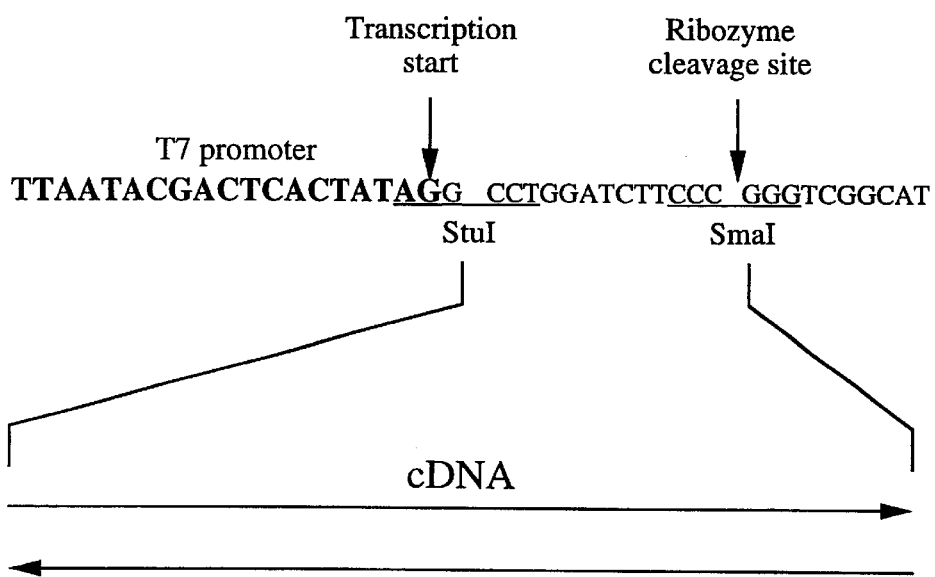
FIG. 1. Transcription vector pOLTV5 is a derivative of the transcription vector described by Pattnaik et al. (1992). See text for details of the construction. The plasmid contains the T7 DNA-dependent RNA polymerase promoter (shown in boldface) followed by unique StuI and SmaI restriction sites and the autocatalytic ribozyme from hepatitis delta virus (JHDV). DNA fragments can be cloned between the StuI and SmaI sites and can be transcribed either in vitro or in vivo by using T7 RNA polymerase. The 5' end of the resulting transcripts contains two extra G-residues which are not encoded by the insert. Due to the action of the ribozyme, the 3' end of the transcripts exactly corresponds to the last nucleotide of the insert.

A low-copy-number transcription vector was constructed by using plasmid pOK12 (Vieira and Messing, 1991) as the basic replicon. Plasmid pOK12 was digested with PvuII and the DNA fragment containing the replication origin and the Kanamycin-resistance gene was isolated. This DNA fragment was ligated to an Eco47III-AflII fragment (the AflII site was made blunt by using Klenow DNA polymerase I) from transcription vector 2.0 (a generous gift of Dr. Andrew Ball; Pattnaik et al., 1992). From the resulting plasmid an XbaI-NheI fragment was deleted to eliminate as much unique restriction sites as possible. The resulting plasmid was designated pOLTV5 (FIG. 1). Transcription vector pOLTV5 contains the T7 DNA dependent RNA polymerase promoter followed by unique StuI and SmaI restriction sites, the autocatalytic ribozyme from hepatitis delta virus (HDV) and the transcription termination signal from bacteriophage T7. DNA fragments cloned between the StuI and SmaI restriction sites can be transcribed either in vitro or in vivo by using T7 RNA polymerase. After transcription, the 5' end of the resulting transcripts contains two G residues encoded by the plasmid. Due to the autocatalytic action of the HDV ribozyme, the 3' end of the transcripts corresponds to the exact terminal nucleotide of the cloned DNA fragment (Pattnaik et al., 1992).

Construction of Minigenome Plasmids

Figure 2A:
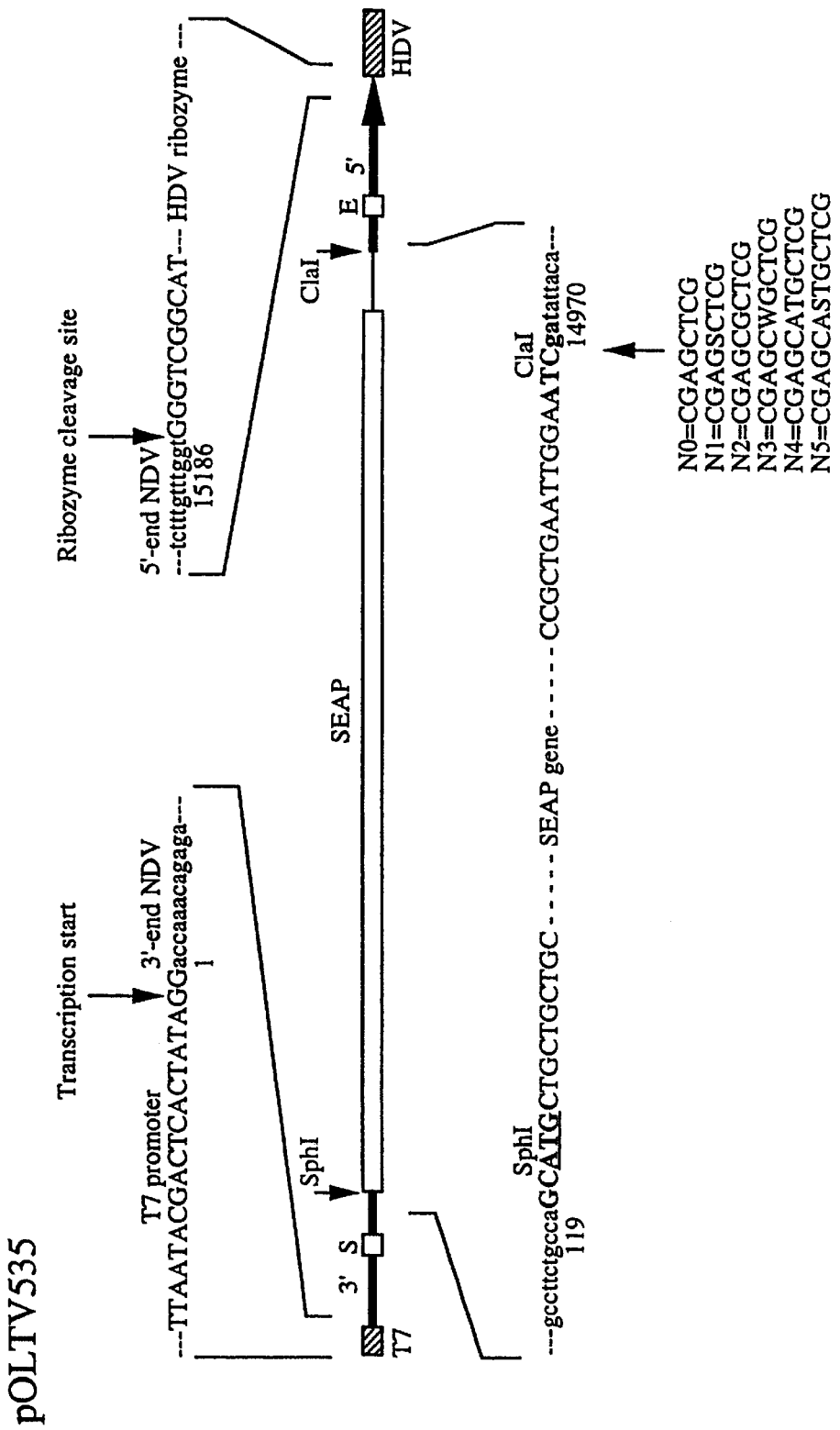
FIG. 2. Structure of the minigenome plasmids pOLTV535 (Part A of FIG. 2) and pOLTV553 (Part B of FIG. 2). The minigenome plasmids are based on transcription plasmid pOLTV5 (cf.
Figure 2B:
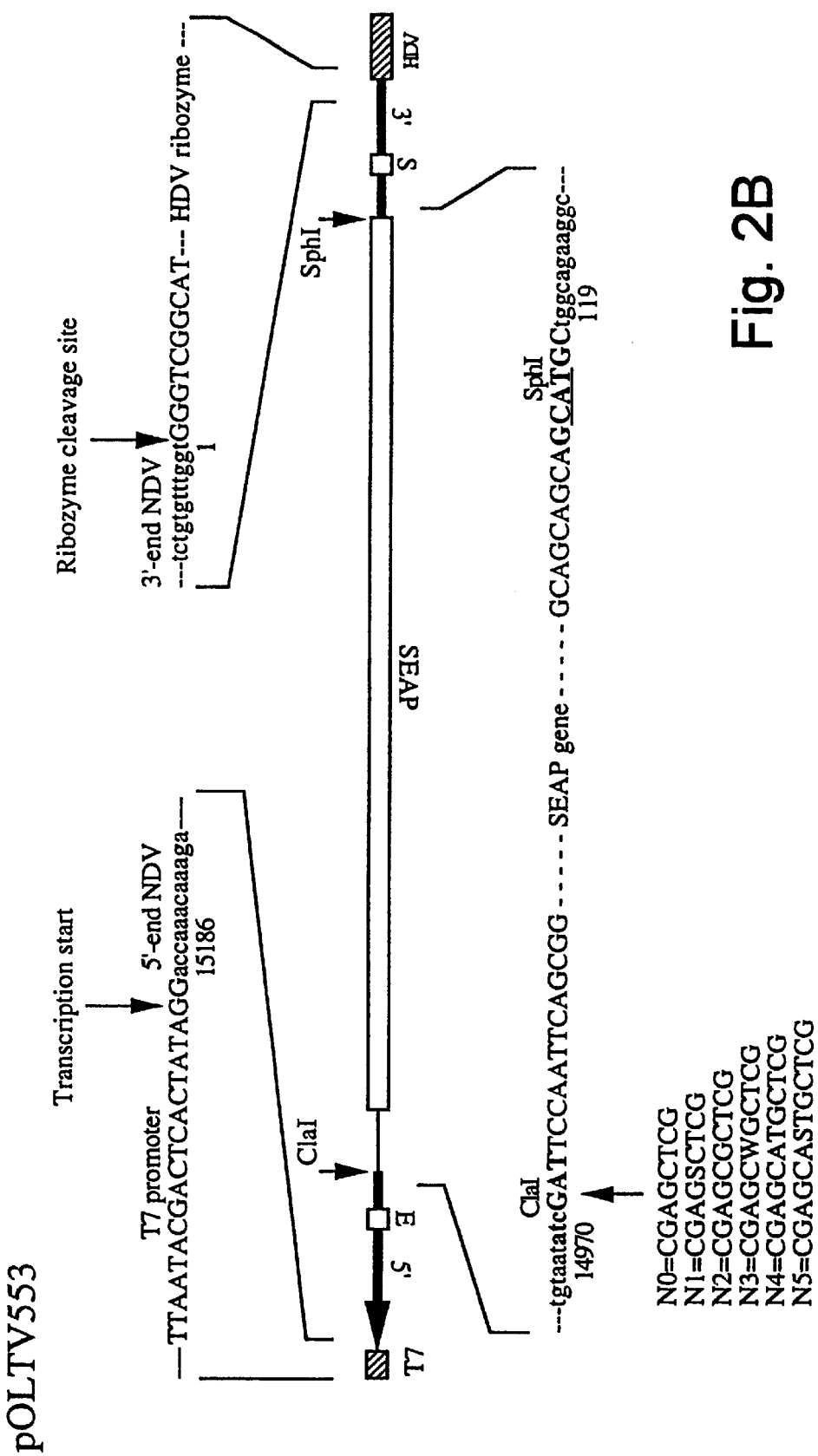

In order to examine the requirements for replication and transcription of NDV, minigenome plasmids were constructed which contained the 3' and 5' terminal regions of NDV flanking a reporter gene that replaced all NDV genes (FIG. 2). DNA fragments corresponding to the 3' and 5' terminal regions of NDV were generated by means of PCR by using Pwo DNA polymerase (30 cycles; 15 sec at 94° C., 30 sec at 50° C., and 30 sec at 72° C.) and using plasmids containing the 3' and 5' RACE fragments as templates (see above).

The 3' region (nt 1–119) was generated by using primers 3UIT (5'-ACCAAACAGACAATCCGTGAGTTACGA-3', (SEQ ID NO: 1) nt 1–27) and SEAP3 (5'-ATCGATACTGGTCAGCATGCT GGCAGAAGGCTTTCTCG-3' (SEQ ID NO: 87), nt 102–119). The 5' region (nt 14973–15186) was generated by using primers SEAP5 (5'-GCATGCTCACCAGTATCGAT ATTACAGTAACTGTGACT-3', (SEQ ID NO:88) nt 14973–14990) and 5NDV (5'-ACCAACAAACATTTGGTGAATGACGA-3', (SEQ ID NO:79) nt 15158–15186). The two DNA fragments were joined in an overlap PCR (the overlap is shown in italics in the primer sequences shown above) by using primers 3UIT (SEQ ID NO: 1) and 5NDV (SEQ ID NO: 79). The resulting DNA fragment, which is a fusion of the 3' and 5' end of NDV separated by 20 nucleotides, was phosphorylated by treatment with T4 polynucleotide kinase and cloned in both orientations in transcription plasmid pOLTV5 (FIG. 1) which was cleaved with StuI and SmaI and dephosphorylated with calf intestinal phosphatase (Boehriflger Mannheim). Finally, the SEAP-gene (encoding secreted alkaline phosphatase) was recovered from plasmid pSEAP-Basic (Clontech) by digestion with SphI and ClaI, and cloned between the SphI and ClaI sites between the 3' and 5' ends of NDV. The resulting plasmids were designated pOLTV535 and pOLTV553, respectively. In vivo or in vitro transcription using T7 RNA polymerase of plasmid pOLTV535 gives rise to antigenomic RNA ([+1-RNA), whereas transcription of plasmid pOLTV553 gives rise to genoinic RNA ([−]-RNA).

Plasmids pOLTV535N0 to -N5 and pOLTV553N0 to -N5 were generated by inserting self-complementary oligonucleotides in the ClaI-site located between the SEAP-gene and the 5' end of NDV in pOLTV535 and pOLTV553, respectively (see FIG. 2). The oligonucleotides used were: N0, 5'-CGCGAGCTCG-3' (SEQ ID NO: 89); N1, 5'-CGCGAGSCTCG3' (SEQ ID NO: 90), N2, 5'-CGCGAGCGCTCG-3' (SEQ ID NO: 91); N3, 5'-CGCGAGCWGCTCG 3' (SEQ ID NO: 92); N4, 5'-CGCGAGCATGCTCG-3' (SEQ ID NO: 93); N5, 5'-CGCGAGC.ASTGCTCG-3' (SEQ ID NO:94) (W=A or T; S C or G).

Modification of the T7 Promoter in Plasmids pOLTV535 and pOLTV553

To generate in vitro or in vivo transcripts containing the authentic 5' and 3' terminal ends of NDV, the T7 promoter in plasmids pOLTV535 and pOLTV553 was modified such that transcription would start at the first nucleotide of the 3' or 5' terminal end of NDV.

Primers were designed which contained, 1) a BglII-restriction site, 2) the sequence of the T7 promoter (shown in italics) which was modified such that the two G residues at the end of the T7 promoter were replaced by an A residue, and 3) the 3' (nt 1–21) or 5' end (nt 15164–15186) of NDV. Primers BGL3F2 (5'-GATATGGCCATTCAGGCTTAATACGACTCACTATA ACCAAACAGAGAATCCGTGAG-3' (SEQ ID NO: 95)) and SEAP3 (SEQ ID NO: 87) (see above) were used to generate a DNA fragment containing the modified T7 promoter and the entire 3' end of NDV up to the start of the SEAP gene in pOLTV535. Similarly, a DNA fragment was generated that containing the modified T7 promoter and the entire 5' end of NDV up to the end of the SEAP gene in pOLTV553 by using primers BGL5F2 (5'-GATATGGCCATTCAGGCTTAATACGACTCACTATA ACCAAACAAAGATTTGGTGAATG 3' (SEQ ID NO: 95)) and SEAP5 (SEQ ID NO: 88). The resulting fragments were digested with BglI and SphI (3' end) or BglI and ClaI (5' end), respectively, and used to replace the BglI-SphI fragment in pOLTV535, or the BglI-ClaI fragment in pOLTV553. The resulting plasmids were designated p0LTV735 and p0LTV753, respectively. Plasmids pOLTV735N3 and pOLTV753N3 were generated by inserting a self-complementary oligonucleotide (5'-CGCGAGCWGCTCG-3 (SEQ ID NO: 92); W=A or T) in the ClaI-site located between the SEAP-gene and the 5' end of NDV in pOLTV735 and pOLTV753, respectively.

Construction of SEAP-Reporter Plasmids

Plasmid pCIneoSEAP was constructed by cloning an XhoI-ClaI fragment (ClaI-site was made blunt by using a Klenow DNA polymerase I) containing the SEAP-gene from plasmid pSEAP Basic (Clontech) between the XhoI and SmaI sites of the eukaryotic expression vector pCIneo (Promega). The latter plasmid contains the human cytomegalovirus (hCMV) promoter in addition to the bacteriophage T7 promoter. In order to examine and quantitate SEAP expression by transcripts generated from the T7 promoter only, another plasmid was constructed which lacked the hCMV promoter. To this end the hCMV promoter was deleted from pCIneo by partial digestion with HindIII followed by complete digestion with BglII. The DNA fragment (nt 756–5469 according to numbering of Clontech) from which the hCMV promoter was deleted was isolated, treated with T4 DNA polymerase to generate blunt ends and recircularized by using T4 DNA ligase. The resulting plasmid was designated pCIneoD. Finally, the SEAP gene was recovered from pSEAP-Bacis as an MluI-AccI fragment and cloned in pCIeoD between the MluI and ClaI sites. The resulting plasmid was designated pCIneoD SEAP.

Transfections

Cells were seeded in 24-well culture dishes, grown overnight to 60–80% confluency, and infected at a m.o.i. of 1 with FPV-T7 for 1 h at 37° C. The cells were transfected with 0.5 µg minigenome plasmid DNA by using 3 µl of LipofectAMINE™ and OptiMem essentially as described by the supplier (GibcoBRL/Life Technologies). After incubation for 4 h (CER cells) or 16H (QM5 cells) at 37° C. the cells were either infected with NDV (Dutch virulent isolate nr. 152608; 200 µl per well) for 1 h at a m.o.i. of 5, or left uninfected. The inoculum was aspirated and replaced by 1 ml of complete medium and the cells were further incubated at 37° C.

For co-transfections, cells were grown in 6-well culture dishes and infected with FPV-T7 as described above. The cells were co-transfected with 0.25 µg minigenome plasmid DNA, 0.4 µg pCIneonP, 0.2 µg pCIneoP and 0.2 µg pCIneoL (c) or pCIneo by using either 8 µl of LipofectAMINE or 9 µl of FuGene 6 (Boehringer Mannheim). In order to generate infectious virus, the minigenome plasmid was replaced by a transcription plasmid that contained the full-length NDV cDNA.

Quantitation of SEAP Activity

The amount of SEAP which was secreted into the medium of transfected cells was measured in disposable 96-well plates by using the Phospha-Light™ Chemiluminescent Reporter Assay for Secreted Alkaline Phosphatase kit essentially as described by the supplier (Tropix). Chemiluminescense was quantitated by using a liquid scintillation counter (Wallac 1450 microbeta PLUS).

Cloning and Sequencing of cDNA's Spanning the Entire Genome of NDV Strain LaSota To clone and sequence the entire genome of NDV strain LaSota, large subgenomic cDNA clones were generated by means of RT-PCR and cloned in pGEM-T. First strand cDNA synthesis was performed by using primer 3UIT (SEQ ID NO: 1) as described above, and 1 µl of the RTreaction was used in a PCR reaction by using the Expand Long Template PCR kit (Boehringer Mannheim). The PCR consisted of 5 cycles of 10 sec at 94° C., 30 sec at 58° C., and 6 min at 68° C., followed by 10 cycles of 10 sec at 94° C., 30 sec at 58° C., and 6 min at 68° C., in which the elongation time at 68° C. was increased by 20 sec per cycle. The PCR fragments were cloned in pGEM-T by using the pGEM-T cloning kit essentially as decribed by the supplier (Promega). Ligation mixtures were tranformed into E. coli strain SURE II (Stratagene). Two independent RT-PCR reactions (A and B) were performed and each yielded a similar set of cDNA clones. The nucleotide sequence of the subgenomic cDNA clones was determined by using NDV-specific primers (Table 1) and by primers flanking the inserts. After comparsion of the nucleotide sequence of the A and B series of clones, remaining ambiguities were resolved by sequencing relevant regions of a third independent series of cDNAs (C series). The nucleotide sequence of NDV strain LaSota is shown in FIG. 3 (SEQ ID NO: 134).

Construction of a Full Length Genomic cDNA Clone of NDV

The full-length NDV cDNA was assembled in transcription plasmid pOLTV5 by using pOLTV535 as the starting plasmid. The DNA fragments were joined at overlaps by using common restriction enzymes as detailed in portion B of FIG. 4. In a series of cloning steps, a plasmid (designated p535-DI) was constructed containing nucleotides 1–3521 and 12355–15186 separated by a ClaI site that was generated by joining the ClaI-sites at position 3521 and 12355. In another series of cloning steps, a plasmid (designated pGEM-B) was constructed which contained part of the NDV genome including nucleotides 3521–12355 (ClaI-fragment). To facilitate cloning, the latter ClaI fragment was tagged with the Chloramphenicol resistance (Cm) gene from plasmid pACYC184 (Chang and Cohen, 1978). To this end the Cm-gene was recovered from pACYC184 by means of PCR by using primers CAT-F (5' GCGTACGTCTAGACTGGTGTCCCTGTTGATACCGG-3'(SEQ ID NO: 96)) and CAT-R (5'-GCTCTAGACGTACGACCCTGCCCTGAACCGACG-3' (SEQ ID NO: 97)). The PCR was carried out with Pwo DNA polymerase and consisted of 30 cycles of 30 sec at 94° C., 45 sec at 60° C., and 60 sec at 72° C. The resulting PCR fragment was digested with BsiWI and cloned in the unique BsiWI site of pGEM-B, yielding PGEM-B(CAT). The ClaI fragment from pGEM-B(CAT) was cloned in the unique ClaI site of p535-DI, yielding pNDFL(CAT). Finally, the Cm-gene was removed from this plasmid by digestion with BsiWI followed by religation and transformation of E. coli strain DH5a. The resulting plasmid was designated pNDFL+ and contains the entire NDV cDNA sequence cloned between the T7 promoter and the HDV ribozyme in transcription plasmid pOLTV5.

Cloning and Expression of Individual NDV Genes

DNA fragments containing each of the NDV LaSota genes were generated by means of RT-PCR and cloned in pCIneo. After cloning, all fragments were sequenced by using primers flanking the inserts and by gene-specific primers. NP gene: Primer 386 (5' GAGCAATCGAAGTCGTACGGGTAGAACGTG- 3', (SEQ ID NO: 98) nt 40–69) was used for reverse transcription. Primers 365 (5'-GTGTGAATTC CGAGTGCGAGCCCGAAG-3'; (SEQ ID NO: 99) nt 77–94) and 892 (5'-TTGCATGCCTGCA GGTCAGTACCCCCAGTC3' (SEQ ID NO: 100) nt 1577–1593) were used for PCR by using Pwo DNA polymerase. The following PCR profile (30 cycles) was used; 30 sec at 95° C., 40 sec at 65° C., and 45 sec at 72° C. The resulting DNA fragment was digested with EcoRI and cloned in pCIneo between the EcoRI and SmaI sites. Expression of NP was verified in an immunoperoxidase monolayer assay (IPMA) as described by Peeters et al (1992) by using monoclonal antibody 38 (Russell et al., 1983). P gene:

Primer pRT1 (5'-CAAAGAATTC AGAAAAAAGTACGGGTAGAA-3'; (SEQ ID NO: 8) nt 1794–1814) was used for reverse transcription. Primers pRT1 (SEQ ID NO: 8) and p2 (5'GCAGTCTAGA TTAGCCATTCACTGCAAGGCGC- 3'; (SEQ ID NO: 101) nt 3053–3071) were used for PCR by using Pwo DNA polymerase. The following PCR profile (30 cyles) was used; 30 sec at 95° C., 40 sec at 65° C., and 60 sec at 72° C. The resulting DNA fragment was digested with EcoRI and XbaI and cloned in pCIneo between the EcoRI and XbaI sites. Expression of P was verified in an IPMA by using monoclonal antibody 688 (Russell et al., 1983).

M-gene: Primer 3UIT (5' ACCAAACAGAGAATCCGTGAGTTACGA-3' (SEQ ID NO: 1) nt 1–27) was used for reverse transcription. Primers NDV5M (5'-GGGTGCTAGC GGAGTGCCCCAATTGTGCCAA- 3' (SEQ ID NO: 102) nt 3268–3288) and NDV3M (5'TCTCCCCGGG GCAGCTTATTTCTTAAAAGGAT-3' (SEQ ID NO: 56) nt 4368–43 89) were used for PCR by using the Expand High Fidelity kit. The PCR consisted of 10 cycles of 15 sec at 95° C., 30 sec at 55° C., and 2 min at 68° C., followed by 15 cycles in which the elongation time at 68° C. was increased for 20 sec per cycle. The resulting DNA fragment was treated with T4 DNA polymerase to create blunt ends, digested with NheI, and cloned in pCIneo between the NheI and SmaI sites. Expression of the M protein was verified in an IPMA by using monoclonal antibody 424 (Russell et al., 1983).

F-gene: Primer 3UIT (SEQ ID NO: 1) (see above) was used for reverse transcription. Primers NDV5F (5'-ACGGGCTAGCGATTCTGGATCCCGGTTGG-3' (SEQ ID NO: 15); nt 4508–4526) and NDV3 F (5'-ACTACCC GGGAAACCTTCGTTCCTCAT-3' (SEQ ID NO:60) nt 6212–31) were used for PCR by using the Expand High Fidelity kit using the conditions described above for the M-gene. The resulting DNA fragment was treated with T4 DNA polymerase to create blunt ends, digested with NheI, and cloned in pCIneo between the NheI and SmaI sites. Expression of the F protein was verified in an IPMA by using monoclonal antibody 8E12A8C3 (ID-DLO, department of Avian Virology).

HN-gene: Primer 3UIT (SEQ ID NO: 1) was used for reverse transcription. Primers NDV5HN (5'-GTAGGCT GCAAGAGAGGCCGCCCCTCAAT 3'; (SEQ ID NO: 22) nt 6335–6354) and NDV3HN (5'-CGAGCCCGGG CCGGCATTCGGTTTGATTCTTG-3' (SEQ ID NO: 104); nt 8205–8227) were used for PCR by using the Expand High Fidelity kit using the conditions described above for the M-gene. The resulting DNA fragment was treated with T4 DNA polymerase to create blunt ends and after digestion with XmaI it was cloned in pCIneo between the blunted (Klenow DNA polymerase) NheI site and the XmaI site. Expression of the HN protein was verified in an IPMA by using monoclonal antibody 86 (Russell et al., 1983).

L-gene: The L-gene was recovered from cDNA clone pGEM-L7a (Portion A of FIG. 4) by digestion with SacII and SalI. Before digestion with SalI, the SacII site was made blunt by treatment with T4 DNA polymerase. The resulting fragment was cloned in pCIneo between the blunted (Klenow DNA polymerase) NheI site and the SalI site. The 5' untranslated region between the T7 promoter and the ATG start codon of the L-gene contained 2 out-of-frame ATG codons which might interfere with correct expression of the L protein. Therefore, a new plasmid was constructed in which the first ATG was missing and in which the second ATG was changed to AAG by means of PCR mutagenesis, as follows. Primers 5LE(E) 5'-CAATGGAATT CAAGGCAAAACAGCTCAAGGTAAATAATACGGG-3' (SEQ ID NO: 104); nt 8332–8374) and 3LE (B) 5' GTGAATCTAGAATGCCGCATCCGTACGAATGC-3' (SEQ ID NO: 105); nt 8 847–8870) were used in a PCR reaction using plasmid pGEM-L7a (FIG. 4) as a template. The PCR was carried out by using Pwo DNA polymerase and consisted of 30 cycles of 30 sec at 94° C., 45 sec at 60° C., and 60 sec at 72° C. The resulting DNA fragment was digested with EcoRI and XbaI and cloned in pCIneo between the EcoRI and XbaI sites, generating plasmid pCIneoL(N). Subsequently, the BsiWI-SalI fragment from pGEML7a, which contains the remaining part of the L-gene (nt 8852–15046), was cloned in pCIneoL(N) between the BsiWI and SalI sites, generating plasmid pCIneoL(c). Since antibodies against the L-protein are not available, expression of L could not be checked by immunochemistry.

Introduction of a Genetic Tag in the F-Gene.

To show unambiguously that infectious virus can be generated from cloned full-length cDNA, a genetic tag was introduced in the F gene by means of PCR mutagenesis. To this end, the F-gene was cloned by using two overlapping PCR fragments. The first PCR fragment was generated by using primers NDV5F (SEQ ID NO: 15) (see above) and primer F5R (5'-AAAGCGCCGCTGTCTCCT CCCTCCAGATGTAGTCAC-3' (SEQ ID NO: 106); nt 4859–4894). The residues shown in bold are changes which were introduced in the primer in order to change the amino acid sequence of the proteolytic cleavage site between F1 and F2 from that of the NDV LaSota strain (GGRQGR|L) (SEQ ID NO: 135) to that of the consensus cleavage site for virulent NDV strains (GRRQRR|F) (SEQ ID NO: 102) The second PCR fragment was generated by using primers F3F (5'-GGAGGAGACAGCGGCGCT TTAGGCGCCATTATTGG-3' (SEQ ID NO: 107); nt 487524911) and IV09 (5'-CTCTGTCGAC ACAGACTACCAGAACTTTCAC-3' (SEQ ID NO: 108); nt 6246–6266).

The PCR was performed with Pwo DNA polymerase and consisted of 25 cycles of 15 sec at 94° C., 30 sec at 55° C., and 2 min at 72° C. The two overlapping PCR fragments (the overlap is shown in italics in the primer sequences) were joined in a second PCR by using primers NDV5F (SEQ ID NO: 15) and IV09 (SEQ ID NO: 108) and by using the same PCR conditions. The resulting fragment, which contains the entire ORF of the F gene and which encodes a virulent consensus cleavage site, was digested with NheI and SalI and cloned in pCIneo between the NheI and SalI sites, yielding pCIneoF$^{wt}$. The StuI-NotI fragment (nt 4646–4952) from pCIneoF$^{wt}$ was used to replace the corresponding fragment in plasmid p535-S which had been constructed by inserting the ClaI-ScaI (nt 3521–10311) from pGEM-B in p535-DI between the ClaI and ScaI sites (see portion C of FIG. 4). The resulting plasmid was designated p535-S[F$^{wt}$c]. A PCR fragment containing the Cm-resistance gene from pACYC184 (see above) was cloned as an XbaI fragment into the unique XbaI site (position 6172 in the NDV sequence) of plasmid p535-S [F$^{wt}$c], yielding plasmid p535-S [F$^{wt}$c] Cm. Subsequently, the Cm-tagged ApaI-SpeI fragment (nt 2285–8094) of this plasmid was used to replace the corresponding fragment of the full-length cDNA clone pNDFL+. Finally, the Cm-gene was removed from this plasmid by digestion with XbaI followed by recircularization using T4 DNA ligase. The resulting plasmid, which contains the genetically tagged full-length NDV cDNA, was designated pNDFL+[F$^{wt}$].

Generation of Stably Transformed Cell Lines that Express Individual NDV Genes

Plasmids pCIneoNP, pCIneoP, pCIneoM, pCIeoF, pCIneoF$^{wt}$, and pCIneoHN were used for the generation of stably transformed cell lines that express these proteins individually. The day before transfection, CER cells were seeded in 6 cm culture dishes and incubated overnight to give a confluency of 60–80%. The cells were transfected with 2 µg of plasmid DNA by using 12 µl of LipofectAmine and OptiMem essentially as described by the supplier (GibcoBRL/Life Technologies). After 48 h the cells were trypsinized and dilutions were seeded in 10 cm culture dishes in medium containing 500 µg/ml of G418 (Boehringer Mannheirn). Every 3 days the medium was replaced by fresh medium containing increasing (in steps of 100 µg/ml) amounts of G418 until a concentration of 800 µg/ml was reached. Cells were kept in medium containing 800 µg/ml G418 and three weeks after transfection individual colonies were picked and transferred to 96-well culture dishes. The cloned cell lines were examined for the expression of the respective NDV gene by using an IPMA as described above for transient expression studies.

Cell lines that constitutively expressed NP, P, M, or F could be identified and isolated. We were unable, however, to generate cell lines that expressed the HIN protein. Perhaps constitutive expression of HN is toxic to the cells.

Generation of Stably Transformed Cell Lines that Express T7 RNA Polymerase

The gene encoding T7 RNA polymerase was recovered from plasmid pRT7NT (Rene van Gennip, ID-DLO, Department of Mammalian Virology) by digestion with EcoRI and SalI. The resulting fragment contains the T7 RNA polymerase gene located behind the baculovirus p10 promoter. The DNA fragment was cloned in plasmid pCIneo0 between the EcoRI and SalI sites, generating plasmid pCIneo107. Plasmid pCIneo0 lacks the T7 promoter and was derived from pCInco by cleavage with NheI followed by partial cleavage with ScaI, filling in the sticky ends with Klenow DNA polymerase and recircularization by using T4 DNA ligase. The baculovirus sequences were removed from pCIneo107 by digestion with EcoRI and PacI, followed by T4 DNA polymerase treatment to generate blunt ends and recircularizaton. The resulting plasmid was designated pCIneo007. Expression of T7 DNA polymerase was verified by co-tranfection of cells with pCIneo007 and pPRh01. The latter plasmid contains the E2 protein of classical swine fever virus cloned behind a T7 promoter and containing an internal ribosome entry site (Rene van Gennip, personal communication). Expression of E2 was determined in an IPMA by using monoclonal antibody V4 (Wensvoort et al., 1986). Stably transformed CER cell lines expressing T7 RNA polymerase were generated and isolated as described above except that 10 cm culture dishes were used and the cells were transfected with 5 µg of pCIneo007 DNA and 25 µl of LipofectAMINE. To examine individual cell lines for the expression T7 RNA polymerase, they were transfected with plasmid pPRh01 and expression of E2 (which is dependent on T7 RNA polymerase) was determined in an IPMA by using monoclonal antibody V4. Several cell lines which expressed T7 RNA polymerase were identified. One cell line, designated CER-C9, was used for subsequent experiments.

Cloning and Expression of HN-Genes and Hybrid-HN Genes

Primer 3UIT (SEQ ID NO: 1) was used to synthesize single-stranded cDNA of NDV and avian paramyxovirus serotype-2 and -4 (APMV2 and APMV4) as described above. All subsequent PCR reactions were performed by using 25 cycles of 15 sec at 94° C., 30 sec at 55° C. and 2 mm at 72° C.

The entire coding region of the HN-gene of APMV2 was recovered by means of PCR by using primers IV03 (5'-GGGGGAATTCCCCATTCAATGAAGGGTCTAC-3' (SEQ ID NO: 110)) and IV05 (5'-GATCCCCGGG TCTTAAACCAGGCTTCGCAATG-3' (SEQ ID NO: 111)) which were derived from the sequence of the HN gene of APMV2 (GenBank accession number D 14030). The entire coding region of the HN-gene of APMV4 was recovered by means of PCR by using primers IV06 (5'-GGGGGAATTC TGGTAGGGTGGGGAAGGTAGC-3' (SEQ ID NO: 112)) and IV08 (5'-ATTGCCCGGG GGGTAACTAATCAGGATCTCAG-3' (SEQ ID NO: 113)) which were derived from the sequence of the HN-gene of APMV4 (GenBank accession number D14031). The resulting PCR fragments were digested (either directly or after subcloning in pGEM-T), with EcoRI and XmaI and cloned in pCIneo between the EcoRI and XmaI sites. The resulting plasmids were designated pCIneoHN2 and pCIneoHN4 respectively.

Hybrids between the HN-gene of NDV strain LaSota and the HN-genes of APMV2 and -4 were constructed by means of overlap PCR as follows. The N-terminal part (aa 1–141) of the HN-gene of NDV strain LaSota was amplified with Pwo DNA polymerase by using primers IV01B (5'-GTAGGAATTCAAGAGAGGCCGCCCCTCAAT-3' (SEQ ID NO: 114); nt 6325–6354) and IV10 (5'-AATGAGTTCTTTGCCTATCCCCCC-3' (SEQ ID NO: 115) nt 6811–6834). The C-terminal part of the HN-gene of APMV2 (aa 142–580) was amplified with Pwo DNA polymerase by using primers IV11B (5'-GGGGGGATAGGCAAAGAACTCATT CAAGGATGCATCTGCAGGC-3' (SEQ ID NO: 116) and IV05 (SEQ ID NO: 111). The resulting PCR fragments were joined in an overlap PCR (overlap shown in italics) by using primers IV01B (SEQ ID NO: 114) and IV05 (SEQ ID NO: 111) and by using the Expand High Fidelity enzyme mix. The resulting PCR fragment was digested (either directly or after subcloning in pGEM-T) with EcoRI and XmaI and cloned in pCIneo between the EcoRI and XmaI sites. The resulting plasmid which contains a hybrid HN-gene consisting of aa 1–141 of NDV and aa 142–580 of APMV2 was designated pCIneoEN1/2$^{141}$.

The C-terminal part of the HN-gene of APMV4 (aa 143–569) was amplified by using primers IV14B (5'-GGGGGGATAGGCAAAGAACTCATT GTAGATGATGCATCTGCAGGCCTAATTTCC-3' (SEQ ID NO: 117) and IV08 (SEQ ID NO: 113). This fragment was joined with the N-terminal part of the HN-gene of NDV (see above) in an overlap PCR by using primers IV01B (SEQ ID NO: 114) and IV08 (SEQ ID NO: 113). The resulting PCR fragment was digested (either directly or after subcloning in pGEM-T) with EcoRI and XmaI and cloned in pCIneo between the EcoRI and XmaI sites. The resulting plasmid which contains a hybrid HN gene consisting of aa 1–141 of NDV and aa 143–569 of APMV4 was designated pCIneoEN1/4$^{141}$.

In analogy to the constructions described above, hybrid HN genes were constructed which consisted of aa 1–143 of NDV and aa 144–580 of APMV2, or aa 1–143 of NDV and aa 145–569 of APMV4. For these constructions PCR fragments were obtained by using the following pairs of primers; NDV aa 1–143, primer IV01B (SEQ ID NO: 114) and IV13 (5'-ATCTACAATGAGTTCTITGCCTATC-3' (SEQ ID NO: 118); nt 6816–6840); APMV2 aa 144–580, primer UV14B (5'-GGGGGGATAGGCAAAGAACTCATTGTAGAT GATGCATCTGCAGGCCTAAATTTCC-3' (SEQ ID NO: 117) and IV05 (SEQ ID NO:111); APMV4 (SEQ ID NO:

128) aa 145–569, primer IV15B (5'-GGGGGATAGGCAAAGAACTCATTGTAGAT CAAACAGCTGACTACACAGCAG-3' (SEQ ID NO: 119) and IV08 (SEQ ID NO:113). The PCR fragments were digested (either directly or after subcloning in pGEM-T) with EcoRI and XmaI and cloned in pCIneo between the EcoRI and XmaI sites. The resulting plasmids were designated pCIneo1/2$^{143}$ and pCIneO1/4$^{143}$, respectively. To examine expression of the HN proteins, CER cells or QM5 cells were infected with FPV-T7 for 1 h at a m.o.i. of 1, transfected with plasmids pCIneoHN, pCIneoHN2, pCIneoHN4, pCIneoHN1/2$^{141}$, .pCIneoHN1/2$^{143}$, pCIneoHN1/4$^{143}$ and pCIneoHN1/4$^{143}$ and 24 h after transfection the monolayers were overlayed with a 1% suspension of chicken erythrocytes in PBS for 45 mm at roomtemperature. Subsequently, the monolayers were carefully washed three times with PBS and adhesion of erythrocytes to transfected cells was examined microscopically. To examine induction of cell fusion after co-expression of the HN and F protein, CER cells or QM5 cells were co-transfected with pCIneoF$^{wt}$ together with either pCIneo-HN1 pCIneoHN2, pCIneoHN4, pCIneoHN1/2$^{141}$ pCIneoHN1/4$^{141}$, pCIneoHN1/2$^{243}$ or pCIneoHN1/4$^{143}$. After incubation for 2 to 3 days, the monolayers were washed with PBS, stained for 15 min with a Giemsa solution (1:30 dilution in water), and examined microscopically.

Cloning of Hybrid-HN Genes in Full Length Genomic NDV cDNA

A synthetic linker, designated HN12, was inserted between the NotI and SpeI sites of pGEM-T (Promega) by using oligonucleotides HN12a (5'-GGCCGCATATTCTAGAGTTAACGACTTA-3' (SEQ ID NO: 120)) and HN12b (5'-CTAGTAAGTCGTTAACTCTAGAATATGC-3' (SEQ ID NO: 121)). A synthetic linker, designated HN14, was inserted between the NotI and SpeI sites of pGEM-T by using oligonucleotides HN14a (5'-GGCCGCATATTCTAGAGTTAACGA-3' (SEQ ID NO: 122)) and HN14b (5'-CTAGTCGTTAACTCTAGAATATGC-3' (SEQ ID NO: 123)). The resulting plasmids were designated pGEM-HN12 and pGEM-HN14, respectively. These plasmids were digested with NotI and XbaI and used to clone the NotI-SpeI fragment (nt 3390–7488) from plasmid p535-S[F$^{wt}$c]Cm. The resulting plasmids were designated pGEM-HN1/2NS and pGEM-HN1/4NS, respectively. The HN genes of these plasmids were replaced by the hybrid HN genes from plasmids pCIneoHN1/2$^{143}$ and pCIneoHN1/4$^{143}$, respectively (see-section: Cloning and expression of HN-genes and hybrid-HN genes). To this end, pCIneoHN1/2$^{143}$ and pCIneoHN1/4$^{143}$ were digested with NheI and SmaI and the resulting fragments (containing the hybrid HN1/2$^{143}$ and hybrid HN1/4$^{143}$genes) were cloned between the NheI and HpaI site of plasmids pGEM-HN1/2NS and pGEM-HN1/4NS, resulting in pGEM+HN12 and pGEM+HN14, respectively. The latter plasmids were used to introduce the hybrid HN genes into the full length genomic cDNA clone of NDV. To this end, plasmids pGEM+HN12 and pGEM+HN14 were digested with NotI and SpeI and the fragment containing either the HN12 or HN14 gene was used to replace the corresponding fragment of pNDFL+, yielding pNDFL+HN1/2$^{143}$ Cm and pNDFL+HN1/4$^{143}$ Cm, respectivley. The Cm-gene was removed from these plasmids by digestion with XbaI followed by recircularization using T4 DNA ligase. In order to comply with the "rule-of-six", a linker was inserted into the unique SpeI site of these plasmids by using self-complementary oligonucleotides. Linker H2 (5-CTAGCGAGCGCTCG-3' (SEQ ID NO: 124)) was inserted in plasmid pNDFL+HN1/2$^{143}$ and linker H3 (5'-CTAGCGAGCWGCTCG-3' (SEQ ID NO: 125)) was inserted in pNDFL+HN1/4$^{143}$, yielding plasmids pNDFL+HN1/2$^{143}$ (112) and pNDFL+HN1/4$^{143}$ (H3) respectively.

Elimination of a Specific Epitope in the HN Protein of NDV LaSota

A specific epitope, i.e., amino acids 346 to 354 (PDEQDYQIR) (SEQ ID NO: 126), in the HN protein of NDV LaSota that is recognized by MAb 4DE (Long-et al., 1986; Meulemans et al., 1986), was eliminated by replacing this sequence by the corresponding sequence of the HN proteins of either APMV-2 (NRTDIQQTI) (SEQ ID NO: 127) or APMV-4 (PDPLQDQIL) (SEQ ID NO: 128). To this end, plasmid pCIneoHN (see section: Cloning and expression of individual NDV genes) was used as template to create overlapping PCR fragments. For the APMV-2 (SEQ ID NO: 127) sequence the first PCR fragment was generated by using primers IV01 (5'-GTAGACGCGTAAGAGAGGCCGCCCCTCAAT-3' (SEQ ID NO: 129)) and primer 3HN2 (5'-GATAGTTTGCTGTATATCAGTCCGATTGCATGTGTC ATTGTATCGCTTGTATATCAC-3' (SEQ ID NO: 130)). The second PCR was generated by using the primers 5HN2 (5'-AATCGGACTGATATACAGCAAACTAT-CATGGCCAAGTCTTCGTATAAGCCTGGAGCC 3' (SEQ ID NO: 131)) and NDV3 HN (5'-CGAGCCCGGGCCGGCATTCGGTTTGATTCTTG 3' (SEQ ID NO: 103)). The resulting fragments were combined and used as template for a third PCR by using the primers IV01B (5'-GTAGGAATTCAAGAGAGGCCGCCCCTCAAT 3' (SEQ ID NO: 114)) and primer NDV3-HN (SEQ ID NO: 103). For the APMV-4 (SEQ ID NO: 128) sequence the first PCR fragment was generated by using primers IV01 (SEQ ID NO: 129) and primer 3HN4 (5'-TAAGATCTGATCTTGCAGCGGGTCAGGGCATGTGT CATTGTATCGCTTGTATATCAC-3' (SEQ ID NO: 115)). The second PCR was generated by using the primers 5HN4 (5'-CCTGACCGCTGCAAGATCAGATCTTAATGG CCAAGTCTTCGTATAAGCCTGGAGCC-3' (SEQ ID NO: 116)) and NDV3-HN (SEQ ID NO: 104). The resulting fragments were combined and used as template for a third PCR by using the primers IV01B (SEQ ID NO: 114) and NDV3-HN (SEQ ID NO: 104). Primers 3HN2/5HN2 and 3HN4/5HN4 are partly complementary and contain the genetic codes for the HN2 sequence (NRTDIQQTI) (SEQ ID NO: 127) and HN4 sequence (PDPLQDQIL) (SEQ ID NO: 128), respectively. The PCR reactions were performed by using the Expand Long Template PCR kit (Boehringer Mannheim). The PCR consisted of 30 cycles of 10 sec 94° C., 30 sec 58° C. and 2 min at 68° C., followed by 1 cycle of 4 min 68° C. The PCR fragments were digested with EcoNI and Bsu36I, and cloned between the EcoNI and Bsu36I sites of pCIneoHN. The resulting plasmids were designated pCIneoHN1HN2e) and pCIneoHN1(HN4e) respectively. Transient expression studied indicated that the modified HN proteins were correctly expressed and transported to the cell surface as judged from haemadsorbtion studies using chicken erythrocytes. Furthermore, MAb 6D4 which is directed against a linear epitope of HN of NDV and which consists of (or at least includes, amino acids 346–354) did not react with the modified HN proteins.

Plasmids pCIneoHN(HN2e) and pCIneoHN1(HN4e) were digested with NarI and SpeI and the fragments containing the modified HN genes were cloned between the NarI and SpeI sites of pGEM-HN1/2NS and pGEM-HN1/4NS, respectively. The resulting plasmids, designated pGEN-HN1 (HN2e) and pGEM-HN1(HN4e), were digested with NotI and SpeI, and used to replace the NotI-SpeI fragment in pNDFL+. The resulting plasmids were designated pNDFL-HN(HN2e)Cm and pNDFL-HN(HN4e) Cm, respectively. The Cm-gene was removed from these plasmids by digestion with XbaI followed by religation. The resulting plasmids were designated pNDFL-HN(HN2e) and pNDFL-HN(HN4e), respectively.

Results

Nucleotide Sequence of the 3' and 5' Terminal Ends of the Genome of NDV Strain LaSota The sequence of a putative 3' end of the NDV genome has been published (Ishida et al., 1986) albeit from another NDV strain (D26) than the one used here (LaSota). Yusoff et al. (1987) have published a sequence of the L-gene and a relatively large non-coding region behind the L-gene of NDV strain Beaudette C. However, as shown herein, this sequence did not include the full terminal 5' end of the viral genome which makes it impossible to generate infectious copy NDV. The 3' and 5' terminal ends of the genome of negative-strand RNA viruses fulfil an essential function in replication and transcription (Lamb and Kolakofsky, 1996). Thus, in order to generate a full-length NDV cDNA which can be used to generate infectious virus by means of reverse genetics (Conzelmann, 1996), it is absolutely essential to include the correct 3' and 5' ends of the viral genome. Therefore, we determined the exact nucleotide sequence of both the 3' and 5' ends of the genomic RNA of NDV strain LaSota by using 3' and 5' RACE procedures (rapid amplification of cDNA ends). The 5' end was recovered by means of PCR after ligation of a single-stranded anchorprimer (ALG3) (SEQ ID NO: 83) to single-stranded cDNA which was generated by reverse transcription of the 5' end of the genomic RNA. By using a primer (ALG4) (SEQ ID NO: 85) that is complementary to the anchorprimer and an NDV-specific primer, PCR products were generated which contained the 5' end.

To clone the 3' end of NDV, the single-stranded achorprimer ALG3 (SEQ ID NO: 83) was ligated to the 3' end of viral RNA by using T4 RNA ligase and amplified by means of PCR by using primer ALG4 (SEQ ID NO: 128) and an NDV-specific primer (method I). Alternatively, the 3' and 5' ends of the NDV RNA were ligated to each other by using T4 RNA ligase and the resulting concatenated RNA was used for RT-PCR by using NDV-specific primers that flanked the ligation point (method II). The 3' and 5' RACE products were cloned in T-vector pBluescriptII-TSK (Ichihara and Kurosawa, 1993) or in pGEM4Z and several independent clones were isolated and sequenced. The results are compiled in Table 2. To enable the direct comparison of the 3' and 5' terminal ends, the sequences are shown in the form of DNA and the 3' end of the genomic strand is represented as the 5' end of the antigenomic strand. At the genomic RNA level the sequence of the 3'-end reads 3'-UGGUUUGUCUCUUAG (SEQ ID NO: 132) whereas the sequence of the 5'-end reads UUUAGAAACAAACCA-5' (SEQ ID NO: 133). The sequence of the 3' end is almost similar to the published 3' terminal sequence of NDV strain D26 (Ishida et al., 1986). However, the sequence of the 5' end showed that NDV strain LaSota contains 64 additional nucleotides in comparison with the published sequence of the L-gene of NDV strain Beaudette C (Yusoff et al., 1987). (FIG. 6.)

Replication of NDV Minigenomes by Helpervirus

To determine whether the 3' and 5' ends of NDV are functional in replication and transcription, minigenomes were constructed which consisted of the 3' end of NDV (nt 1–119), a reporter gene encoding secreted alkaline phosphatase (SEAP), and the 5' end of NDV (nt 14973–15186) (FIG. 2). These minigenomes were cloned in both orientations in transcription vector pOLTV5, generating plasmids pOLTV535 and pOLTV553 respectively (for details of the construction see Materials and Methods). Plasmid pOLTV5 (FIG. 1) contains the T7 RNA polymerase promoter followed by unique StuI and SmaI restriction sites, the autocatalytic ribozyme from hepatitis delta virus (HDV) and the transcription termination signal from bacteriophage T7 (Pattnaik et al., 1992). In vivo or in vitro transcription using T7 RNA polymerase of plasmid pOLTV535 gives rise to antigenomic RNA (or [(+]-RNA), whereas transcription of plasmid pOLTV553 gives rise to genomic RNA (or [(-]-RNA) (FIG. 5).

To examine whether the minigenome RNA's generated by plasmids pOLTV535 and pOLTV553 could be replicated and expressed by using NDV as helper virus, we used CER cells which expressed T7 RNA polymerase either constitutively (CER-C9 cells, see Materials and Methods), or after infection with fowlpox recombinant fpEFLT7pol (Britton et al., 1995; hereafter called FPV-T7) that expresses T7 RNA polyinerase. CER-C9 cells and FPV-T7 infected CER cells were transfected with the minigenome plasmids pOLTV535 or pOLTV553 and after incubation for 3 h at 37° C. the cells were either infected with NDV for 1 h, or left uninfected. Approximately 24 h after transfection, a sample was taken from the medium and assayed for SEAP activity. The results showed the SEAP expression as very high in FPV-T7 infected cells which were transfected with pOLTV535. This is not surprising since transcription by T7 RNA polymerase generates antigenomic [+]-RNA which is capped by fowlpox enzymes and which is efficiently translated by the host cell. In cells transfected with pOLTV553, transcription by T7 RNA polymerase generates genomic [-]-RNA which must be converted, into [+]-RNA by helpervirus in order to be translated into SEAP protein (cf. FIG. 5). In both cases, no increase in SEAP expression could be observed in NDV infected cells in comparison to non-infected cells. On the contrary, SEAP-expression in NDV infected cells was consistently approximately two times lower than in uninfected cells (results not shown). For pOLTV535-transfected cells this may be explained by the already very high level of SEAP expression by transcripts generated by T7 RNA polyinerase. However, in pOLTV553-traflfected cells, where efficient expression .of SEAP is dependent on the conversion of genomic [-]-RNA into antigenomic [+]-RNA or rnRNA by the viral polymerase complex, we would have expected an increase in SEAP expression after NDV infection.

We could think of two reasons why the minigenomes could not be expressed and replicated by NDV. First, the size of the minigenome RNA's does not conform to the so-called "rule-of-six" (Calain and Roux, 1993; Kolakofsky et al., 1998). According to this rule, paramyxovirus genomes are only replicated efficiently when they are a multiple 6 nt in length. Second, the two extra G residues which are present at the 5' end of the minigenome RNA's might interfere with correct replication and/or transcription by the viral polymerase complex. To find out whether replication of the genomes was dependent on the rule-of-six, we inserted a series of short self-complementary oligonucleotides which increased 1 nt in size in the unique ClaI-site in plasmids pOLTV535 and pOLTV553 (FIG. 2). The resulting plasmids (pOLTV535N0 to -N5 and pOLTV553N0 to -N5) differ in size from 1 to 6 nt and therefore one of them should generate a minigenome RNA which conforms to the rule-of-six. The plasmids were used to transfect CER cells or FPV-T7 infected CER-C9 cells as described above. The results showed that only plasmids pOLTV535N3 and pOLTV553N3 gave rise to an enhanced SEAP-activity after NDV infection. The length of the minigenome RNA's generated from these plasmids by T7 RNA polymerase were calculated to be 6n+2. Since two extra G residues are present at the 5' end of the minigenome RNA's, these results suggest that only the size of the RNA sequence which is located between the authentic 3' and 5' ends of the minigenome RNA's is relevant for the rule-of-six. This was verified by constructing minigenome plasmids in which the transcription start of T7 RNA polymerase was changed so that the first nucleotide which was incorporated into RNA was the first nucleotide of the 3' or 5' end of NDV (see Materials and Methods). Transfection of these plasmids indicated that only minigenome RNA's generated by plasmids pOLTV735N3 and pOLTV753N3 are replicated by helpervirus (results not shown). These findings again indicate that replication of NDV is strictly dependent on the rule-of-six. Furthermore, these findings indicate that the presence of two extra G residues at the 5'-end of the minigenome RNA's does not interfere with correct replication. Similar results have been obtained with minigenome plasmids (or DI plasmids) from other paramyxoviridae (Pattnaik et al., 1992; Harty and Palese, 1995).

Packaging of NDV Minigenomes by Helpervirus

To determine whether minigenome RNA's could be packaged by NDV helpervirus, the medium of the transfected cells was transferred to fresh monolayers and after 1 h of adsorbtion, the monolayers were washed three times with PBS and further incubated in complete medium. After 24 h of incubation, the SEAP activity in the medium was measured. The results showed that SEAP activity was present only in cells which had been treated with the medium from cells transfected with minigenome plasmid pOLTV553N3 (Table 4). This finding indicates that minigenome RNA's can be packaged into NDV envelopes and that these particles are able to infect cells. Furthermore, these results show that packaging is dependent on replication which indicates that only RNA molecules which are complexed with the viral NP, P and L proteins are packaged into virus-like particles.

Replication of NDV Minigenomes by Plasmids Expressing the NP, P, and L Proteins

To determine whether the minigenome RNA's could also be replicated by plasmids encoding the essential NP, P, and L proteins, we performed co-transfection experiments in cells infected with FPV-T7. Cells were transfected with a combination of plasmids consisting of the minigenome plasmid and plasmids pCIneoNP, -P, and -L(c), respectively. As a negative control, pCIneoL(c), which encodes the essential L protein, was replaced by the vector plasmid pCIneo. The results (Table 5) indicated that indeed plasmids encoding NP, P, and L are able to replicate minigenome RNA's. The results furthermore show that, similar to minigenome replication by helpervirus, also replication by the NP, P, and L proteins is dependent on the rule-of-six.

Nucleotide Sequence of the Complete Genome of NDV Strain LaSota

Sub-genomic cDNA fragments spanning the entire NDV genome were constructed by means of RT-PCR (FIG. 4). To keep the number of PCR errors to a minimum, a proofreading enzyme-mix (Expand Long Template; Boehringer Mannheim) was used in combination with a limited number of PCR cycles (15 cycles). Primer 3UIT (SEQ ID NO: 1) which is complementary to the 3' end of NDV RNA was used for reverse transcription, and gene-specific primers were used for PCR. To identify possible PCR errors, three independent RT reactions were performed and used to generate three independent sets of subgenomic cDNA's. The CDNA's, which varied in size from approximately 4 to 7 kb, were cloned in pGEM-T. The nucleotide sequence of two sets of cDNA'5 was determined by using primers which were either deduced from published NDV sequences, or by primers derived from the NDV sequence that was deduced during this sequencing project (Table 1). Remaining ambiguities were resolved by sequencing the relevant regions of the third set of cDNA clones. The genome of NDV strain LaSota consists of 15186 nt (FIG. 3), which makes it the smallest of all paramyxovirus genomes from which the entire sequence has been established to date (Kolakofsky et al., 1998).

Construction of a Full-Length NDV cDNA Clone in Transcription Plasmid pOLTV5

To construct a full-length cDNA clone of NDV strain LaSota, overlapping cDNA clones spanning the entire NDV genome were joined at shared restriction sites according to the strategy shown in FIG. 4. The entire NDV cDNA was assembled in the minigenome plasmid pOLTV535 (see above) which is derived from transcription plasmid pOLTV5.

As can be seen in portion B of FIG. 4, the last step in the assembly of the complete NDV cDNA was the cloning of an approximately 8.8 kb ClaI (nt 3521–12355) fragment from pGEM-B into p535-DI which contained the NDVsequences flanking the ClaI site at either side (i.e., nt 1–3521 and 12355–15186, respectively). This step proved to be quite difficult since we repeatedly failed in generating the correct clones. Therefore, the ClaI fragment of pGEM-B was tagged with the chloramphenicolresistance (Cm) gene from plasmid pACYC184. The ClaI fragment harboring the Cm-gene was isolated and cloned in the ClaI site of p535-DI and transformants were selected for resistance against both Cm. Since transformants grew poorly, the antibiotic selection was reduced to 15 $\mu$g/ml Cm and 10 $\mu$g/ml Km and the incubation temperature was reduced from 37° C. to 32° C. Finally, the Cm-gene was removed from this plasmid by digestion with BsiWI followed by recircularization by using T4 DNA ligase. After transformation of E. coli, cells harboring the desired plasmid were identified phenotypically by screening for Km-resistance and Cm-sensitivity. The resulting plasmid which consisted of the full-length NDV cDNA cloned between the SmaI and StuI sites of transcription plasmid pOLTV5 was designated pNHFL+.

Generation of Infectous NDV from Full-Length cDNA

To generate infectious NDV entirely from cloned cDNA, plasmid pNDFL+ was used in co-transfection experiments with pCIneoNP, -P, and -L(c), as described above for the minigenome plasmids. Transfection of CER and CEF cells was monitored by using minigenome plasmid pOLTV553N3 and by measuring SEAP expression. As a negative control, pCIneoL(c) was replaced by pCIneo. After co-transfection, the cells were incubated for 3 to 6 days in medium containing 5% allantoic fluid. The addition of allantoic fluid is neccessary because CER or CEF cells lack the appropriate proteases which are required to cleave the F protein of NDV strain LaSota. Cleavage of the F protein is absolutely required for cell-to-cell spread and for the generation of infectious virus. After 3 days of incubation, we performed an immunological staining of the fixed monolayers by using a monoclonal antibody against the F protein. The results showed that cells that were stained with the antibody were only present in monolayers which had been co-transfected with pNDFL(+), pCIneoNP, -P, and L(c). These results indicated that genome replication and expression was occuring in these cells. No staining cells were observed when pCIneoL(c) was replaced by pCIneo in the co-transfection experiments.

To recover infectious virus, the supernatant of transfected CEF monolayers was injected into the allantoic cavity of embryonated eggs. Four days later the allantoic fluid was harvested, analyzed in a haemagglutination assay, and passaged further in eggs. The results showed that only the supernatant of cells transfected with a combination of pNDFIL+ and pCIneoNP, -P, and -L(c) yielded a positive reaction in the haemagglutination assay. Allantoic fluid which showed a positive haemagglutination reaction was subsequently analyzed in a haemagglutination inhibition assay by using monoclonal antibodies 7B7, 8C11, 5A1, 7D4, and 4D6 (Long et al., 1986) which can be used to differentiate between different NDV strains. The results of this assay indicated that the NDV strain which was revovered from the inoculated eggs showed the same reactivity as the original LaSota strain. The virus which was recovered from the inoculated eggs was designated NDFL to distinguish it from the original LaSota strain.

Generation of Genetically Modified NDV from Full-Length cDNA

To show unambiguously that the co-transfection system could be used to recover infectious virus from cloned full-length NDV cDNA, a genetic tag was introduced in plasmid pNDFL(+). To this end, the amino acid sequence of the protease cleavage site in the Fo protein was changed from that of the LaSota strain (GGRQGR I L) (SEQ ID NO: 134) to the consensus sequence of virulent NDV strains (GRRQRR I F) (SEQ ID NO: 135) by means of PCR mutagenesis (for details see Materials and Methods). The resulting plasmid, pNDFL+[$F^{wt}$], was used to generate virus by using the co-transfection system described above. Infectious virus, designated NDFL[$F^{wt}$], was recovered from the allantoic fluid of embryonated eggs which had been inoculated with the medium of co-transfected CEF cells. In an HI test, all MAb's including 7D4, which is specific for the LaSota strain, showed the same reactivity with the newly generated virus as with the original LaSota strain. The nucleotide sequence of the region encoding the protease cleavage site of the F protein was determined by means of RT-PCR. The results showed that the nucleotide sequence contained the exact nucleotide changes which were introduced in the mutagenic primer which was used to modify the original LaSota sequence. This finding shows that the virus was derived from plasmid pNDFL+[$F^{wt}$] and demonstrates that (genetically modified) NDV can be generated entirely from cloned full-length NDV cDNA.

The Protease Cleavage Site of the Fo Protein of NDV is a Key Determinant for Virulence.

It is generally assumed that the amino acid sequence of the protease cleavage site of the Fo protein is a key determinant for virulence of different NDV strains. The generation of a genetically modified LaSota strain in which the amino acid sequence of the protease cleavage site was changed from a lentogenic (non-virulent) to that of a velogenic (virulent) NDV strain offered the unique oppertunity to test this assumption. Therefore, we determined the intracerebral pathogenicity index (ICPI) of the newly generated virus NDFL[$F^{wt}$] and compared it with that of strain NDFL and of the original LaSota strain (clone E13-1). The results showed that the ICPI of strain NDFL[$F^{wt}$] was 1.3 which is far above the value for strains NDFL (ICPI=0.0) and clone E13-1 (ICPI=0.3). These results show that, as expected, the virulence of NDV is largely determined by the amino acid sequence of the protease cleavage site of the Fo protein.

Introduction of Serological Marker

The envelope glycoproteins F and HN of NDV are the most immunogenic proteins of the virus. After infection, both the F and HN protein elicit a strong neutralizing antibody response. The induction of such a neutralizing antibody response is the basis of successful vaccination by nonvirulent NDV strains (such as the widely used LaSota strain). However, the antibody response against NDV vaccine strains cannot be distinguished from the antibody response against virulent NDV field strains. Thus, infections with virulent field virus cannot be traced by serological methods. This situation is undesirable since field virus infections are masked by vaccination and clinical signs which are caused by field strains may be overlooked or are even attributed to the vaccine. Since successful differentiation between vaccination and infection is essential for eradication of NDV, we set out to develop genetically modified NDV strains which can be used for vaccination and which can be serologically distinguished from NDV field strains (so called marker vaccines).

In order to develop an NDV marker vaccine, the virus has to be genetically modified such that one or several immunodominant epitopes of one of the (major) antigens are either deleted or modified. Deletion of part(s) of an essential protein may lead to the loss of the biological function of that protein. Therefore, we chose to modify one of the immunodominant envelope proteins of NDV in such a way that the biological function of the protein was retained whereas the antibody repertoire against the modified protein differed from that against the original protein. For reasons specified below, we chose for one embodiment of the invention to modify the HN protein of NDV. Infection of NDV is initiated by fusion of the virion envelope with the plasma membrane of the host cell. For this process, both the F protein and the HN protein are required. It has been shown that the F and HN proteins physically interact and that this interaction is required for membrane fusion (Deng et al., 1995). Furthermore, it has been shown that the interaction is type specific, i.e., the F and HN proteins must be derived from the same virus in order to shown fusion activity. The interacting domain of the HN protein of NDV has been localized to the so-called stalk- or stem-region of the protein, comprising the first 92 amino acid residues of the ectodomain of the HN protein (Deng et al., 1995). Hybrid HN proteins consisting of aa 1–141 of NDV and aa 141–572 of human parainfluenza virus type-3 (hPIV3) were shown to retain fusion activity when co-expressed with the NDV F protein. These finding suggests that genetically modified NDV strains which harbor a hybrid HN protein which consists of the stem region of NDV followed by the globular head of the HN protein of a different avian paramyxovirus serotype may be viable. Furthermore, such strains would elicit an anti-HN antibody response which is different from that of NDV. Since the neutralizing antibody response against the F protein is sufficient to allow efficient protection against challenge vfrus infection, such genetically modified NDV strains meet the two essential requirements of a marker vaccine, i.e., protection against disease and serological differentiation.

Hybrid HN genes were constructed which consisted of a fusion of either aa 1–141 of NDV and aa 142–580 of avian paramyxovirus type-2 (APMV2) (designated EN1/2$^{141}$) or aa 1–143 of NDV and aa 144–580 of APMV2 (designated HN1/2143). Similarly, hybrid HN genes were constructed which consisted either of aa 1–141 of NDV and aa 143–569 of AMPV4 (designated HN1/4$^{141}$) or aa 1–143 of NDV and aa 145–569 of APNV4 (designated HN1/4$^{143}$). The hybrid genes were cloned in the eukaryotic expression vector pCIneo and used in co-transfection experiments with a plasmid harboring the NDV F protein. To this end, the F protein was modified such that the amino acid sequence of the proteolytic cleavage site between F2 and F1 was changed from the LaSota sequence to that of the consensus sequence of virulent NDV strains ($F^{wt}$, see Materials and Methods section). Co-transfection experiments in CER cells and QM5 cells indicated that both HN1/241 and HN1/2$^{143}$ as well as HN1/4$^{141}$ and HN1/4$^{143}$ induced cell fusion when co-expressed with the $F^{wt}$ protein. These results indicated that the complexes between the hybrid HN proteins and the F protein were biologically active. The hybrid HN proteins HN1/2$^{143}$ and HN1/4$^{143}$ were used to replace the original HN gene in the full-length cDNA clone pNDFL+, yielding pNDFL-HN1/2$^{143}$ and pNDFL-HN1/4$^{143}$. The latter two plasmids were subsequently used for the generation of infectious virus by using the co-transfection system described above. Viable recombinant viruses (designated NDFL-HN1/2$^{143}$ and NDFL-HN1/4$^{143}$) could be isolated from the allantoic fluid of embryonated eggs which had been inoculated with the supernatant of transfected monolayers.

The presence of the hybrid HN gene in each of two recombinants was verified by means of RT-PCR. Haemagglutination inhibition tests showed that monoclonal antibodies and polyvalent antisera against NDV were unable to inhibit agglutination of chicken erythrocytes by the recombinant viruses NDFL-HN1/2$^{143}$ and NDFL-HN1/4$^{143}$. These results indicate that strains NDFL-HN1/2$^{143}$ and NDFL-HN1/4$^{143}$ may be used as vaccines that can be serologically distinguished from classical NDV vaccines.

Expression of a Heterologous Protein from Recombinant NDV

To examine whether foreign genes can be inserted into the NDV genome, we constructed a recombinant virus that carried the SEAP reporter gene. The SEAP gene was derived from plasmid pOLTV535 and was modified to include the typical transcriptional stop and start boxes of NDV. A DNA fragment containing the SEAP gene followed by the transcriptional stop and start boxes was inserted into the XmnI site (nt 109) in plasmid pNDFL+[($F^{wt}$]. Infectious virus, designated NDFL-AP, was generated by means of the co-transfection system, and the presence of the SEAP gene was verified by means of RT-PCR. Cells infected with strain NDFL-AP expressed very high levels) of the SEAP protein. By using the specific activity of the SEAP protein, we calculated that x % of the proteins expressed in cells infected with NDFL-AP consisted of SEAP protein. These results show that heterologous genes can be expressed to very high levels from recombinant NDV.

Generation of an NDV Deletion Mutant on a Trans-Complementing Cell Line

In order to abrogate expression of the M protein of NDV, a large part of the M gene was deleted by digestion of pNVFL+[$F^{wt}$] with BsaAI (nt 3087) followed by partial digestion with HindIII (nt 4252). After filling in the HindIII end with Klenow DNA polymerase, the fragment was recicularized by using T4 DNA ligase and used to transform E. coli. The resulting plasmid, designated pNDFL+[$F^{wt}$]dM, was used to generate virus by means of the co-transfection system in trans-complementing CER-M cells that expressed the NDV M protein. The supernatant of transfected monolayers was passaged three times on CER-M cells and analyzed for the presence of virus. Virus was obtained as evidenced by the fact that the culture supernatant of the third passage yielded positive results in hemagglutination (HA) and hemagglutination inhibition (HI) tests. The virus was designated NDFL-dM. When NDFL-dM was used to infect monolayers of CEF cells, the virus was still able to spread by cell-to-cell transmission as seen in an IPMA by using a monoclonal antibody against the F protein. As expected, expression of the M protein could not be demonstrated in an IPMA by using a monoclonal antibodies against the M protein. When the supernatant was used to infect either CEF cells or CER-M cells, we were unable to show the presence of replicating virus in these monolayers by means of IPMA. This finding indicates that infectious virus could not be generated in non-complementing CEF cells. This finding was confirmed by the observation that inoculation of embryonated eggs with supernatant from infected CEF cells did not result in the generation of progeny virus when tested in HA or HI tests.

The need for better NDV vaccines, and especially the need for NDV marker vaccines, prompted us to develop a reverse genetics system which would allow the genetic modification of NDV. In this document we describe the generation of infectious NDV entirely from cloned full-length cDNA. We show that the virulence of NDV can be dramatically changed by modifying only 3 nucleotides which determine the specificity of the protease cleavage site of the F protein. In this case the protease cleavage site was changed from that of the LaSota strain to that of the consensus cleavage site of virulent NDV strains. By generating this genetically modified NDV strain we deliver the formal proof that the cleavability of the F protein is the key determinant (but not the only determinant) for virulence of NDV. By using the same reverse genetics approach, the cleavage site can be modified, at will, to any other amino acid sequence. This may lead to the generation of a series of NDV strains which display a spectrum of virulence levels.

In Vivo

As already mentioned above, it has been shown that, besides the cleavability of the F and HN proteins, other viral factors may contribute to pathogenicity. Alterations in transcription and translation can modulate growth and cell-to-cell spread of the virus and/or cytopathogenicity. The availability of an infectious cDNA of NDV allows for the systematic modification of sequences which are involved in transcription and replication. This may lead to the design of new NDV vaccines which sport optimal immunogenicity to virtually non-existing virulence.

Safety is one of the most important properties of live vaccines. However, for many live vaccines, including NDV, immunogenicity is often inversely related to virulence. Therefore, further attenuation of live vaccines without losing immunogenicity is one of the most desired alterations for which genetic modification could be used. In this respect it is worthwhile mentioning that it has been shown that elimination of expression of the V protein of Sendai virus resulted in a markedly reduced in vivo pathogenicity for mice (Kato et al., 1997). Similar to Sendai virus, NDV also generates a V protein by a mechanism known as RNA editing (Steward et al., 1993). It is predictable that elimination of expression of the V protein of NDV may also result in an attenuated phenotype in vivo.

Apart from changing the virulence of NDV, we show that it is possible to modify the antigenic make-up of NDV in such a way that strains can be generated which can be serologically discriminated from NDV field strains. These, so called, marker vaccines are an invaluable tool to assess the prevalence of NDV in commercial flocks around the world. Furthermore, the large-scale application of such marker vaccines may ultimately lead to the complete eradication of NDV by a process of intensive screening and stamping out of infected flocks. In this document we show that foreign genes can be inserted into the genome of NDV. These foreign genes can be expressed to very high levels in infected cells. This shows that NDV can be used as a vaccine vector for the expression of antigens from other (poultry) pathogens. Several properties make NDV an ideal vaccine vector for vaccination against respiratory or intestinal diseases. 1) NDV can be easily cultured to very high titres in embryonated eggs. 2) Mass culture of NDV in embryonated eggs is relatively cheap. 3) NDV vaccines are relatively stable and can be simply administered by mass application methods such as addition to drinking water or by spraying or aerosol formation. 4) The natural route of infection of NDV is by the respiratory and/or intestinal tract which are also the major natural routes of infection of many other poultry pathogens. 5) NDV can induce local immunity despite the presence of circulating maternal antibody.

Finally, we show that viable NDV deletion mutants can be generated by using trans-complementing cell lines. An NDV deletion mutant was generated which is unable to express the matrix (M) protein which is involved in budding of NDV at the inner cell membrane. We show that a phenotypically complemented NDV strain that is unable to express the M protein is still able to infect cells and spread by means of cell-to-cell transmission. However, the mutant virus is unable to generate infectious progeny on non-complementing cells. This finding shows that phenotypically complemented NDV deletion mutants may be used as safe self-restricted vaccines which are unable to spread into the environment. Such a non-transmissible vaccine combines the most important advantage of live vaccines, i.e., efficacy, with the most important advantage of killed vaccines, i.e., safety.

TABLE 1

Nucleotide sequence of primers.

| | | |
|---|---|---|
| 3' UIT | ACCAAACAGAGAATCCGTGAGTTA (SEQ ID NO:1) | 1–24 |
| P368+ | GTGATGAGGAACCATGTTGC (SEQ ID NO:2) | 368–387 |
| P800+ | GTCCGCATCTTCTTGGTTAG (SEQ ID NO:3) | 800–819 |
| P1201+ | GAGACTTGGAGTAGAGTACG (SEQ ID NO:4) | 1201–1220 |
| P1279+ | AGCAGCAATGAAGGGCCTGG (SEQ ID NO:5) | 1279–1298 |
| P1356+ | AAATCGGAGTCCTCACTGGG (SEQ ID NO:6) | 1356–1375 |
| P1683+ | CTCTATATGACCACACCCTC (SEQ ID NO:7) | 1664–1683 |
| PRT1 | CAAAGAATTCAGAAAAAAGTACGGGTAGAAG (SEQ ID NO:8) | 1785–1814 |
| P2357+ | GGAAACAGTCAGGAAAGACC (SEQ ID NO:9) | 2358–2377 |
| P2599+ | TAAGTAAAGTTGACTATCAG (SEQ ID NO:10) | 2599–2618 |
| P2852+ | GGCACTTAATAAACTTTCGC (SEQ ID NO:11) | 2852–2871 |
| P3496+ | GAATGAAGAAGCCACTGTCG (SEQ ID NO:12) | 3496–3515 |
| P3587+ | CGGAGATCTTGTTGAGTTGG (SEQ ID NO:13) | 3589–3608 |
| P4267+ | CATTATCCAAGCAGGTACCC (SEQ ID NO:14) | 4270–4299 |
| NDV5- F | ACGGGCTAGCGATTCTGGATCCCGGTTGG (SEQ ID NO:15) | 4498–4526 |
| P4731+ (LS) | AAGCTCCTCCCGAATCTGCC (SEQ ID NO:16) | 4733–4752 |
| P4958+ | AGCTCTGATACAAGCCAAAC (SEQ ID NO:17) | 4960–4979 |
| P5266+ (LS) | CTGGTGGGAATATGGATTAC (SEQ ID NO:18) | 5267–5286 |
| P5591+ (LS) | AGTAACGTTCCCTATGTCCC (SEQ ID NO:19) | 5593–5612 |
| P5616+ | GTATTTATTCCTGCTTGAGC (SEQ ID NO:20) | 5616–5635 |
| P6000 | AATACCCTTGATCAGATGAGAGCC (SEQ ID NO:21) | 6166–6190 |
| NDV5- HN | GTAGGCTAGCAAGAGAGGCCGCCCCTCAAT (SEQ ID NO:22) | 6325–6354 |
| P6693+ (L) | CATTGTTAAAAACTGAGACC (SEQ ID NO:23) | 6695–6714 |
| P7110+ (L) | ATCGGAAGTCTTGCAGTGTG (SEQ ID NO:24) | 7112–7131 |
| P7501+ CL) | TGGTGGGAAACGCATCCAGC (SEQ ID NO:25) | 7503–7522 |
| P7900+ (LS) | AAGACTTAATCCTACGTCTG (SEQ ID NO:26) | 7902–7921 |
| P8590+ | AACTCGGAAGGGCAGTACAC (SEQ ID NO:27) | 8592–8611 |
| L9 000 | TTTGTCACTCCTGAACTTGTCA TT (SEQ ID NO:28) | 9008–9031 |
| P9359+ | CAATGATATAGCAGAATCCG (SEQ ID NO:29) | 9361–9380 |
| P9371+ | GCAGAATCCGTGACTCATGC (SEQ ID NO:30) | 9371–9411 |
| P9390+ | ATAGCTACTGTATTCTCTGG (SEQ ID NO:31) | 9392–9411 |
| P9686+ | TCACACGATATCATGTTGAG (SEQ ID NO:32) | 9686–9705 |
| P9799+ | CACACCCTAACGATAATTGG (SEQ ID NO:33) | 9801–9820 |
| P10198+ | ATAAGAAACGTATCACTGAC (SEQ ID NO:34) | 10200–10219 |
| P10601+ | TTGTCGCGTTGCCTGTATGG (SEQ ID NO:35) | 10603–10622 |
| P11006+ | GCAGACATACTTTGACTCTG (SEQ ID NO:36) | 11008–11027 |
| P11393+ | TCCCTTATTGTCTGGAGTGC (SEQ ID NO:37) | 11395–11414 |
| P11798+ | TGATACGATAGAACTCGTAG (SEQ ID NO:38) | 11800–11819 |
| L12000 | CATATGTCGCCACATGTGAAGGCT (SEQ ID NO:39) | 12008–12031 |
| P12373+ | CAACCAGGACATATGATGAG (SEQ ID NO:40) | 12375–12394 |
| P12796+ | TCGACTGTTCTTACCAACTC (SEQ ID NO:41) | 12798–12817 |
| P12978+ | CACACCAACTTGCAGATACG (SEQ ID NO:42) | 12978–12997 |
| P13236+ | GAGTATCTACTGTCGGATGC (SEQ ID NO:43) | 13238–13257 |
| P13601+ | ATACTTGTTCAGAGGAATAG (SEQ ID NO:44) | 13603–13622 |
| P13943+ | GACCTGACCTCAGATAAAGC (SEQ ID NO:45) | 13946–13965 |
| P14002+ | TATCATTGCTGCATTGTGAC (SEQ ID NO:46) | 14004–14023 |
| P360 | GGCGATGTAATCAGCCTAGTGCTT (SEQ ID NO:47) | 14756–14779 |
| P14812+ | ACTAAGGACATACTTGAAGC (SEQ ID NO:48) | 14812–14831 |
| P230- | CCGGGACTTCTACTTTTAAG (SEQ ID NO:49) | 230–211 |
| P99 8- | TTTGGATATCGCCTGAGAGG (SEQ ID NO:50) | 998–979 |
| P1898- | AAAGGTGGCCATGTTTGTCC (SEQ ID NO:51) | 1898–1879 |
| P2617- | TGATAGTCAACTTTACTTAC (SEQ ID NO:52) | 2617–2598 |

TABLE 1-continued

Nucleotide sequence of primers.

| | | |
|---|---|---|
| P3328– | GCAGAATCAAAGTACAGCCC (SEQ ID NO:53) | 3330–3311 |
| P3610– | CTTGCCAACTCAACAAGATC (SEQ ID NO:54) | 3612–3593 |
| P3990– | GATTAGCATAGTATCCACTG (SEQ ID NO:55) | 3992–3973 |
| NDV3– M | TCTCCCCGGGGCAGCTTATTTCTTAAAAGGAT (SEQ ID NO:56) | 4400–4368 |
| P4593– | GACAGATGCAACTCAGTACC (SEQ ID NO:57) | 4625–4606 |
| P4618– (LS) | ATGCAACTCAGTACCAGCGC (SEQ ID NO:58) | 4620–4601 |
| P5390– | GTAGAGTTACCTGTATACCC (SEQ ID NO:59) | 5411–5392 |
| NDV3– F | ACTACCCGGGAAACCTTCGTTCCTCAT (SEQ ID NO:60) | 6238–6212 |
| P6710– | TCTCAGTTTTTAACAATGCC (SEQ ID NO:61) | 6712–6693 |
| P7093– (LS) | GTTGATGGAACGCAGAGTAG (SEQ ID NO:62) | 7095–7076 |
| P7522– (LS) | CTGCTGGATGCGTTTCCCAC (SEQ ID NO:63) | 7524–7505 |
| P367 | AGGGACCTCAATACTAGCCAGTTC (SEQ ID NO:64) | 8692–8666 |
| P9905– | CTCTATCAAGAGGCGATTAG (SEQ ID NO:65) | 9907–9888 |
| P10320– | TAAGACAGTACTTTTGCAGG (SEQ ID NO:66) | 10322–10303 |
| P10684– | GATGCAACTGTGTCAACACC (SEQ ID NO:67) | 10687–10706 |
| P11122– | AATTGGGCAGGAGTCAGAAC (SEQ ID NO:68) | 11124–11105 |
| P11510– | TGCCTCCATGATAGCATGCG (SEQ ID NO:69) | 11512–11493 |
| P11903– | ATTGCTTGGAAGATGGACC (SEQ ID NO:70) | 11905–11886 |
| P12717– | TGTCATACATATTATGGCG (SEQ ID NO:71) | 12719–12700 |
| P13141 | CAAGAGTACCGTGTACAGCATACC (SEQ ID NO:72) | 13172–13143 |
| P13281– | GACATGATAGAGCTCACCTG (SEQ ID NO:73) | 13302–13283 |
| P14101– | ACGGAATGCATGGCAATCAG (SEQ ID NO:74) | 14163–14144 |
| P14522– | GCTCACCAAACTCTCTGCAC (SEQ ID NO:75) | 14524–14505 |
| P14687– | AGGATCTGTCTCGTGCACTG (SEQ ID NO:76) | 14709–14690 |
| P377 | TTTCTTAAGTTTGGTAATACCTAGGAC (SEQ ID NO:77) | 14888–14861 |
| P359 | CACCAAGTCGACAATTGGCCAGAAAAGGAG (SEQ ID NO:78) | 15186–1519 |
| 5NDV | ACCAAACAAAGATTTGGTGAATGACGA (SEQ ID NO:79) | 15186–15159 |

TABLE 2

Sequence of 3' and 5' terminal ends of the genome of NDV strain La Sota

A. Sequence of 3' terminal end (shown as 5' end of antigenomic DNA strand)

| method I. | clone | sequence |
|---|---|---|
| | 04 | ACCAAACAGAGAATC (SEQ ID NO:80) |
| | 05 | ACCAAACAGAGAATC (SEQ ID NO:80) |
| | 13 | ACCAAACAGAGAATC (SEQ ID NO:80) |
| | 21 | ACCAAACAGAGAATC (SEQ ID NO:80) |

| method II. | clone | sequence |
|---|---|---|
| | 26 | ACCAAACAGAGAATC (SEQ ID NO:80) |
| | 28 | ACCAAACAGAGAATC (SEQ ID NO:80) |
| | 30 | ACCAAACAGAGAATC (SEQ ID NO:80) |
| | 31 | GCCAAACAGAGAATC (SEQ ID NO:81) |
| | 32 | ACCAAACAGAGAATC (SEQ ID NO:80) |
| | 33 | ACCAAACAGAGAATC (SEQ ID NO:80) |
| Consensus | | ACCAAACAGAGAATC (SEQ ID NO:80) |

B. Sequence of 5' terminal end (shown as DNA)

| pBluescriptII-TSK clones | clone | sequence |
|---|---|---|
| | r3101-13 | ACCAAACAAAGATTT (SEQ ID NO:82) |
| | r3101-14 | ACCAAACAAAGATTT (SEQ ID NO:82) |
| | r3101-15 | ACCAAACAAAGATTT (SEQ ID NO:82) |
| | r2601-17 | ACCAAACAAAGATTT (SEQ ID NO:82) |
| | r2601-18 | ACCAAACAAAGATTT (SEQ ID NO:82) |
| | r2601-19 | ACCAAACAAAGATTT (SEQ ID NO:82) |
| | r2601-20 | AACAAGGTGAAGATA (SEQ ID NO:82) |
| | r2601-21 | ACCAAACAAAGATTT (SEQ ID NO:82) |

| pGEM4Z clones | clone | sequence |
|---|---|---|
| | r3101-16 | ACCAAACAAAGATTT (SEQ ID NO:82) |
| | r3101-17 | ACCAAACAAAGATTT (SEQ ID NO:82) |
| | r3101-18 | ACCAAACAAAGATTT (SEQ ID NO:82) |
| | r3101-19 | ACCAAACAAAGATTT (SEQ ID NO:82) |
| | r3101-22 | ACCAAACAAAGATTT (SEQ ID NO:82) |
| Consensus | | ACCAAACAAAGATTT (SEQ ID NO:82) |

TABLE 3

Minigenome replication by NDV helpervirus

A. SEAP activity (cps) after transfection of CER-C9 cells with the pOLTV535 and pOLTV553-series of plasmids.

| plasmid | +NDV | –NDV | ratio |
|---|---|---|---|
| pOLTV535N0 | $3.5 \times 10^4$ | $7.1 \times 10^4$ | 0.49 |
| pOLTV535N1 | 5.9 | 12.1 | 0.49 |
| pOLTV535N2 | 2.4 | 6.2 | 0.39 |
| pOLTV535N3 | 7.6 | 5.2 | 1.46 |
| pOLTV535N4 | 1.8 | 4.1 | 0.44 |
| pOLTV535N5 | 1.5 | 3.0 | 0.50 |
| pOLTV553N0 | $5.5 \times 10^3$ | $9.6 \times 10^3$ | 0.57 |
| pOLTV553N1 | 9.6 | 27.6 | 0.35 |
| pOLTV553N2 | 2.4 | 3.5 | 0.68 |
| pOLTV553N3 | 15.1 | 9.5 | 1.59 |
| pOLTV553N4 | 3.4 | 7.9 | 0.43 |
| pOLTV553N5 | 2.9 | 4.8 | 0.60 |

TABLE 3-continued

Minigenome replication by NDV helpervirus

B. SEAP activity (cps) after transfection of FPV-T7 infected CER cells with the pOLTV553-series of plasmids.

| Plasmid | +NDV | −NDV | ratio |
|---|---|---|---|
| pOLTV553N0 | $7.2 \times 10^4$ | $8.3 \times 10^4$ | 0.86 |
| pOLTV553N1 | 8.4 | 12.0 | 0.70 |
| pOLTV553N2 | 8.9 | 12.6 | 0.71 |
| pOLTV553N3 | 27.4 | 8.6 | 3.19 |
| pOLTV553N4 | 9.7 | 10.4 | 0.93 |
| pOLTV553N5 | 8.5 | 8.1 | 1.05 |

TABLE 4

Transfer of SEAP activity (cps) after treatment of CER cells with the supernatant of FPV-T7 infected CER cells which had been transfected with the pOLTV553-series of plasmids and which had been superinfected with NDV (see Table 3).

| Plasmid | |
|---|---|
| pOLTV553N0 | $2.4 \times 10^3$ |
| pOLTV553N1 | 6.2 |
| pOLTV553N2 | 2.0 |
| pOLTV553N3 | 20.6 |
| pOLTV553N4 | 2.0 |
| pOLTV553N5 | 2.1 |

TABLE 5

SEAP activity (cps) after co-transfection of CER cells with the pOLTV553-series of plasmids and plasmids pCIneoNP, pCIneoP and pCIneoL(c) (or pCIneo as a negative control).

| Plasmid ratio | NP, P & L | NP, P & pCIneo | |
|---|---|---|---|
| pOLTV553N0 | $3.1 \times 10^4$ | $2.7 \times 10^3$ | 11.7 |
| pOLTV553N1 | 4.1 | 5.2 | 7.9 |
| pOLTV553N2 | 3.1 | 3.1 | 10.0 |
| pOLTV553N3 | 35.9 | 3.6 | 100.8 |
| pOLTV553N4 | 1.9 | 4.6 | 4.1 |
| pOLTV553N5 | 1.0 | 4.1 | 2.5 |

What is claimed is:

1. An avian-paramyxovirus cDNA at least comprising a nucleic acid sequence corresponding to the 5'-terminal end, as set forth in SEQ ID NO:82, and, corresponding to the 3'-terminal end, as set forth in SEQ ID NO:80 or SEQ ID NO:81, of the genome of avian-paramyxovirus, said nucleic acid sequence allowing generation of an infectious copy of avian-paramyxovirus, wherein said avian-paramyxovirus is selected from the group consisting of avian paramyxovirus type-1, avian paramyxovirus type-2, avian paramyxovirus type-3, avian paramyxovirus type-4, avian paramyxovirus type-5, avian paramyxovirus type-6, avian paramyxovirus type-7, avian paramyxovirus type-8 and avian paramyxovirus type-9.

2. The avian-paramyxovirus cDNA of claim 1, wherein said cDNA comprises a full-length cDNA.

3. The avian-paramyxovirus cDNA of claim 2, wherein said avian-paramyxovirus cDNA is derived from Newcastle Disease Virus.

4. The avian-paramyxovirus cDNA of claim 1, wherein said cDNA is derived from Newcastle Disease Virus.

5. The avian-paramyxovirus cDNA of claim 4 wherein said Newcastle Disease Virus is a lentogenic virus.

6. The avian-paramyxovirus cDNA of claim 4, wherein said Newcastle Disease Virus is a lentogenic virus derived from a vaccine strain.

7. The avian-paramyxovirus cDNA of claim 6, wherein said vaccine strain is a LaSota strain ATCC VR-699.

8. The avian-paramyxovirus cDNA of claim 1, further comprising a modification in a nucleic acid.

9. The avian-paramyxovirus cDNA of claim 8 wherein said modification comprises a nucleic acid encoding a modified protease cleavage site.

10. The avian-paramyxovirus cDNA of claim 9 wherein said cleavage site is a protease cleavage site of the fusion (F) protein.

11. The avian-paramyxovirus cDNA of claim 8 wherein said modification comprises a nucleic acid encoding a hemaglutinin-neuraminidase (HN) protein.

12. The avian-paramyxovirus cDNA of claim 8 wherein said modification comprises a deletion in a nucleic acid encoding a viral protein.

13. The avian-paramyxovirus cDNA of claim 12 wherein said viral protein is a matrix (M) protein.

14. The avian-paramyxovirus cDNA of claim 1, further comprising a nucleic acid encoding a heterologous antigen.

15. The avian-paramyxovirus cDNA of claim 14 wherein said antigen is derived from a poultry pathogen.

16. The avian-paramyxovirus cDNA of claim 14 further comprising a nucleic acid encoding an immune-stimulatory protein.

17. A cDNA at least comprising a nucleic acid sequence corresponding to the 5'-terminal end, as set forth in SEQ ID NO:82, and, corresponding to the 3'-terminal end, as set forth in SEQ ID NO:80 or SEQ ID NO:81, of the genome of avian-paramyxovirus, said nucleic acid sequence allowing generation of a replicating avian-paramyxovirus minigenome, wherein said avian-paramyxovirus is selected from the group consisting of avian paramyxovirus type-1, avian paramyxovirus type-2, avian paramyxovirus type-3, avian paramyxovirus type-4, avian paramyxovirus type-5, avian paramyxovirus type-6, avian paramyxovirus type-7, avian paramyxovirus type-8 and avian paramyxovirus type-9.

18. The avian-paramyxovirus cDNA of claim 17, wherein said cDNA is derived from Newcastle Disease Virus.

19. The avian-paramyxovirus cDNA of claim 18, wherein said Newcastle Disease Virus is a lentogenic virus.

20. The avian-pammyxovirus cDNA of claim 19, wherein said Newcastle Disease Virus is a lentogenic virus derived from a vaccine strain.

21. The avian-paramyxovirus cDNA of claim 20, wherein said vaccine strain is a LaSota strain ATCC VR-699.

22. The cDNA of claim 17, further comprising a modified nucleic acid.

23. The cDNA of claim 22, wherein said modified nucleic acid comprises a nucleic acid encoding a modified protease cleavage site.

24. The cDNA of claim 23, wherein said cleavage site is a protease cleavage site of the fusion (F) protein.

25. The cDNA of claim 22, wherein said modified nucleic acid comprises a nucleic acid encoding a hemaglutinin neuraminidase (HN) protein.

26. The cDNA of claim 22, where said modified nucleic acid comprises a deletion in a nucleic acid encoding a viral protein.

27. The cDNA of claim 26, wherein said viral protein is a matrix (M) protein.

28. The cDNA of claim 17, further comprising a nucleic acid encoding a heterologous antigen.

29. The cDNA of claim 28, wherein said antigen is derived from a poultry pathogen.

30. The cDNA of claim 28, further comprising a nucleic acid encoding an immune-stimulatory protein.

31. The cDNA of claim 29, further comprising a nucleic acid encoding an immune-stimulatory protein.

32. An infectious copy avian-paramyxovirus obtained by a method, said method comprising:
    transfecting at least one cell with cDNA, said cDNA comprising an avian-paramyxovirus cDNA at least comprising a nucleic acid sequence corresponding to the 5'-terminal end, as set forth in SEQ ID NO:82, and, corresponding to the 3'-terminal end, as set forth in SEQ ID NO:80 or SEQ ID NO:81, of the genome of avian-paramyxovirus; and
    expressing in said cell an infectious copy of avian-paramyxovirus.

33. A vaccine comprising the infectious copy avian-paramyxovirus of claim 32.

34. The vaccine according to claim 33, wherein said vaccine is a live vaccine.

35. The vaccine according to claim 33 wherein said infectious copy avian-paramyxovirus is derived from a Newcastle Disease Virus (NDV).

36. A replication competent avian-paramyxovirus minigenome comprising a first nucleic acid encoding a viral protein selected from the group consisting of NP, P and L and a second nucleic acid sequence corresponding to the 5'-terminal end, as set forth in SEQ ID NO:82, joined to a 3'-terminal end, as set forth in SEQ ID NO:80 or SEQ ID NO:81, of the genome of avian-paramyxovirus, wherein said second nucleic acid is a multiple of six nucleotides and capable of being transcribed, allowing replication of said second nucleic acid sequence.

37. The replication competent avian-paramyxovirus minigenome of claim 36, wherein said second nucleic acid is capable of being transcribed by a heterologous RNA polymerase.

38. The replication competent avian-paramyxovirus minigenome of claim 37, wherein said heterologous RNA polymerase is obtained from a bacteriophage T7.

39. The replication competent avian-paramyxovirus minigenome of claim 36, wherein said second nucleic acid includes a heterologous sequence capable of expressing an antigen.

40. The replication competent avian-paramyxovirus minigenome of claim 39, wherein said antigen is derived from a poultry pathogen.

41. The replication competent avian-paramyxovirus minigenome of claim 36, wherein said second nucleic acid is flanked by a transcription termination sequence.

42. A cDNA at least comprising:
a first nucleic acid sequence as set forth in SEQ ID NO:82;
a second nucleic acid sequence as set forth in SEQ ID NO:80 or SEQ ID NO:81; and,
a third nucleic acid sequence, located between said first and second nucleic acid sequences, said third nucleic acid sequence having a length that is a multiple of six nucleotides and being transcribable.

* * * * *

UNITED STATES PATENT AND TRADEMARK OFFICE
CERTIFICATE OF CORRECTION

PATENT NO. : 6,719,979 B2  Page 1 of 1
APPLICATION NO. : 09/741744
DATED : April 13, 2004
INVENTOR(S) : Bernardus Petrus Hubertus Peeters et al.

It is certified that error appears in the above-identified patent and that said Letters Patent is hereby corrected as shown below:

On the title page:
In item (75) "Inventors," 3rd line, after "Almere (NL);" and before "Arnoud Leonard," insert --Guus Koch, Lelystad (NL);--

In Item (63), "Related U.S. Application Data," 2nd line, change "Jun. 7, 1999." to --Jun. 17, 1999.--

In the claims:
CLAIM 1, COLUMN 99, LINE 2, change "1. An Avian-paramyxovirus eDNA at least comprising a" to --1. An Avian-paramyxovirus cDNA at least comprising a--

Signed and Sealed this

Twenty-first Day of August, 2007

JON W. D

SEQUENCE LISTING

```
<160> NUMBER OF SEQ ID NOS: 148

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
accaaacaga gaatccgtga gtta                                                24

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
gtgatgagga accatgttgc                                                    20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
```
gtccgcatct tcttggttag                                           20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gagacttgga gtagagtacg                                           20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
agcagcaatg aagggcctgg                                           20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
aaatcggagt cctcactggg                                           20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ctctatatga ccacaccctc                                           20

<210> SEQ ID NO 8
<211> LENGTH: 31
<212> TYPE: DNA
<213> ORGANISM: Artificial Sequence
<220> FEATURE:
<223> OTHER INFORMATION: Primer

<400> SEQUENCE: 8
caaagaattc agaaaaaagt acgggtagaa g                              31

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ggaaacagtc aggaaagacc                                           20

<210> SEQ ID NO 10
<211> LENGTH: 20
<212> TYPE: DNA
<213> ORGANISM: Artificial Sequence

```
<220> FEATURE:
<223> OTHER INFORMATION: Primer

<400> SEQUENCE: 10
taagtaaagt tgactatcag                                                     20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ggcacttaat aaactttcgc                                                     20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gaatgaagaa gccactgtcg                                                     20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
cggagatctt gttgagttgg                                                     20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
cattatccaa gcaggtaccc                                                     20

<210> SEQ ID NO 15
<211> LENGTH: 29
<212> TYPE: DNA
<213> ORGANISM: Artificial Sequence
<220> FEATURE:
<223> OTHER INFORMATION: Primer

<400> SEQUENCE: 15
acgggctagc gattctggat cccggttgg                                           29

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
aagctcctcc cgaatctgcc                                                     20
```

```
<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
agctctgata caagccaaac                                               20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ctggtgggaa tatggattac                                               20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
agtaacgttc cctatgtccc                                               20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
gtatttattc ctgcttgagc                                               20

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21 aataccttg atcagatgag agcc                                           24

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
gtaggctagc aagagaggcc gcccctcaat                                    30

<210> SEQ ID NO 23
<211> LENGTH: 20
<212> TYPE: DNA
<213> ORGANISM: Artificial Sequence
<220> FEATURE:
<223> OTHER INFORMATION: Primer
```

<400> SEQUENCE: 23
cattgttaaa aactgagacc                                              20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
atcggaagtc ttgcagtgtg                                              20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
tggtgggaaa cgcatccagc                                              20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
aagacttaat cctacgtctg                                              20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
aactcggaag ggcagtacac                                              20

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28
tttgtcactc ctgaacttgt catt                                         24

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
caatgatata gcagaatccg                                              20

<210> SEQ ID NO 30

```
<211> LENGTH: 20
<212> TYPE: DNA
<213> ORGANISM: Artificial Sequence
<220> FEATURE:
<223> OTHER INFORMATION: Primer

<400> SEQUENCE: 30
gcagaatccg tgactcatgc                                          20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
atagctactg tattctctgg                                          20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
tcacacgata tcatgttgag                                          20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
cacaccctaa cgataattgg                                          20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
ataagaaacg tatcactgac                                          20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
ttgtcgcgtt gcctgtatgg                                          20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
```
gcagacatac tttgactctg                        20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
tcccttattg tctggagtgc                        20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
tgatacgata gaactcgtag                        20

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
catatgtcgc cacatgtgaa ggct                   24

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
caaccaggac atatgatgag                        20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
tcgactgttc ttaccaactc                        20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
cacaccaact tgcagatacg                        20

<210> SEQ ID NO 43
<211> LENGTH: 20
<212> TYPE: DNA

<213> ORGANISM: Artificial Sequence
<220> FEATURE:
<223> OTHER INFORMATION: Primer

<400> SEQUENCE: 43
gagtatctac tgtcggatgc                    20

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
atacttgttc agaggaatag                    20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
gacctgacct cagataaagc                    20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
tatcattgct gcattgtgac                    20

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47
ggcgatgtaa tcagcctagt gctt               24

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
actaaggaca tacttgaagc                    20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
ccgggacttc tactttttaag                   20

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
tttggatatc gcctgagagg    20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
aaaggtggcc atgtttgtcc    20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
tgatagtcaa ctttacttac    20

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
gcagaatcaa agtacagccc    20

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
cttgccaact caacaagatc    20

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
gattagcata gtatccactg    20

<210> SEQ ID NO 56
<211> LENGTH: 32
<212> TYPE: DNA
<213> ORGANISM: Artificial Sequence
<220> FEATURE:

<223> OTHER INFORMATION: Primer

<400> SEQUENCE: 56
tctccccggg gcagcttatt tcttaaaagg at    32

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
gacagatgca actcagtacc    20

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
atgcaactca gtaccagcgc    20

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
gtagagttac ctgtataccc    20

<210> SEQ ID NO 60
<211> LENGTH: 27
<212> TYPE: DNA
<213> ORGANISM: Artificial Sequence
<220> FEATURE:
<223> OTHER INFORMATION: Primer

<400> SEQUENCE: 60
actacccggg aaaccttcgt tcctcat    27

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
tctcagtttt taacaatgcc    20

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
gttgatggaa cgcagagtag    20

```
<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
ctgctggatg cgtttcccac                                           20

<210> SEQ ID NO 64
<211> LENGTH: 24
<212> TYPE: DNA
<213> ORGANISM: Artificial Sequence
<220> FEATURE:
<223> OTHER INFORMATION: Primer

<400> SEQUENCE: 64
agggacctca atactagcca gttc                                      24

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
ctctatcaag aggcgattag                                           20

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
taagacagta cttttgcagg                                           20

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
gatgcaactg tgtcaacacc                                           20

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
aattgggcag gagtcagaac                                           20

<210> SEQ ID NO 69
<211> LENGTH: 20
<212> TYPE: DNA
<213> ORGANISM: Artificial Sequence
<220> FEATURE:
<223> OTHER INFORMATION: Primer
```

-continued

```
<400> SEQUENCE: 69
tgcctccatg atagcatgcg                                              20

<210> SEQ ID NO 70
<211> LENGTH: 19
<212> TYPE: DNA
<213> ORGANISM: Artificial Sequence
<220> FEATURE:
<223> OTHER INFORMATION: Primer

<400> SEQUENCE: 70
attgcttgga agatggacc                                               19

<210> SEQ ID NO 71
<211> LENGTH: 19
<212> TYPE: DNA
<213> ORGANISM: Artificial Sequence
<220> FEATURE:
<223> OTHER INFORMATION: Primer

<400> SEQUENCE: 71
tgtcatacat attatggcg                                               19

<210> SEQ ID NO 72
<211> LENGTH: 24
<212> TYPE: DNA
<213> ORGANISM: Artificial Sequence
<220> FEATURE:
<223> OTHER INFORMATION: Primer

<400> SEQUENCE: 72
caagagtacc gtgtacagca tacc                                         24

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
gacatgatag agctcacctg                                              20

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
acggaatgca tggcaatcag                                              20

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
gctcaccaaa ctctctgcac                                              20

<210> SEQ ID NO 76
<211> LENGTH: 20
```

```
<212> TYPE: DNA
<213> ORGANISM: Artificial Sequence
<220> FEATURE:
<223> OTHER INFORMATION: Primer

<400> SEQUENCE: 76
aggatctgtc tcgtgcactg                                               20

<210> SEQ ID NO 77
<211> LENGTH: 27
<212> TYPE: DNA
<213> ORGANISM: Artificial Sequence
<220> FEATURE:
<223> OTHER INFORMATION: Primer

<400> SEQUENCE: 77
tttcttaagt ttggtaatac ctaggac                                       27

<210> SEQ ID NO 78
<211> LENGTH: 30
<212> TYPE: DNA
<213> ORGANISM: Artificial Sequence
<220> FEATURE:
<223> OTHER INFORMATION: Primer

<400> SEQUENCE: 78
caccaagtcg acaattggcc agaaaaggag                                    30

<210> SEQ ID NO 79
<211> LENGTH: 27
<212> TYPE: DNA
<213> ORGANISM: Artificial Sequence
<220> FEATURE:
<223> OTHER INFORMATION: Primer

<400> SEQUENCE: 79
accaaacaaa gatttggtga atgacga                                       27

<210> SEQ ID NO 80
<211> LENGTH: 15
<212> TYPE: DNA
<213> ORGANISM: Newcastle disease virus LaSota

<400> SEQUENCE: 80
accaaacaga gaatc                                                    15

<210> SEQ ID NO 81
<211> LENGTH: 15
<212> TYPE: DNA
<213> ORGANISM: Newcastle disease virus LaSota

<400> SEQUENCE: 81
gccaaacaga gaatc                                                    15

<210> SEQ ID NO 82
<211> LENGTH: 15
<212> TYPE: DNA
<213> ORGANISM: Newcastle disease virus LaSota

<400> SEQUENCE: 82
accaaacaaa gattt                                                    15

<210> SEQ ID NO 83
<211> LENGTH: 30
<212> TYPE: DNA
```

```
<213> ORGANISM: Artificial Sequence
<220> FEATURE:
<223> OTHER INFORMATION: anchorprimer

<400> SEQUENCE: 83
cacgaattca ctatcgattc tggatccttc                                          30

<210> SEQ ID NO 84
<211> LENGTH: 29
<212> TYPE: DNA
<213> ORGANISM: Artificial Sequence
<220> FEATURE:
<223> OTHER INFORMATION: Primer

<400> SEQUENCE: 84
caatgaattc aaaggatatt acagtaact                                           29

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
gaaggatcca gaatcgatag                                                     20

<210> SEQ ID NO 86
<211> LENGTH: 28
<212> TYPE: DNA
<213> ORGANISM: Artificial Sequence
<220> FEATURE:
<223> OTHER INFORMATION: Primer

<400> SEQUENCE: 86
gagccttaag gagctgctcg tactgatc                                            28

<210> SEQ ID NO 87
<211> LENGTH: 38
<212> TYPE: DNA
<213> ORGANISM: Artificial Sequence
<220> FEATURE:
<223> OTHER INFORMATION: Primer

<400> SEQUENCE: 87
atcgatactg gtcagcatgc tggcagaagg ctttctcg                                 38

<210> SEQ ID NO 88
<211> LENGTH: 38
<212> TYPE: DNA
<213> ORGANISM: Artificial Sequence
<220> FEATURE:
<223> OTHER INFORMATION: Primer

<400> SEQUENCE: 88
gcatgctgac cagtatcgat attacagtaa ctgtgact                                 38

<210> SEQ ID NO 89
<211> LENGTH: 10
<212> TYPE: DNA
<213> ORGANISM: Artificial Sequence
<220> FEATURE:
<223> OTHER INFORMATION: oligonucleotide

<400> SEQUENCE: 89
cgcgagctcg                                                                10
```

<210> SEQ ID NO 90
<211> LENGTH: 11
<212> TYPE: DNA
<213> ORGANISM: Artificial Sequence
<220> FEATURE:
<223> OTHER INFORMATION: oligonucleotide

<400> SEQUENCE: 90
cgcgagsctc g                                             11

<210> SEQ ID NO 91
<211> LENGTH: 12
<212> TYPE: DNA
<213> ORGANISM: Artificial Sequence
<220> FEATURE:
<223> OTHER INFORMATION: oligonucleotide

<400> SEQUENCE: 91
cgcgagcgct cg                                            12

<210> SEQ ID NO 92
<211> LENGTH: 13
<212> TYPE: DNA
<213> ORGANISM: Artificial Sequence
<220> FEATURE:
<223> OTHER INFORMATION: oligonucleotide

<400> SEQUENCE: 92
cgcgagcwgc tcg                                           13

<210> SEQ ID NO 93
<211> LENGTH: 14
<212> TYPE: DNA
<213> ORGANISM: Artificial Sequence
<220> FEATURE:
<223> OTHER INFORMATION: oligonucleotide

<400> SEQUENCE: 93
cgcgagcatg ctcg                                          14

<210> SEQ ID NO 94
<211> LENGTH: 15
<212> TYPE: DNA
<213> ORGANISM: Artificial Sequence
<220> FEATURE:
<223> OTHER INFORMATION: oligonucleotide

<400> SEQUENCE: 94
cgcgagcast gctcg                                         15

<210> SEQ ID NO 95
<211> LENGTH: 55
<212> TYPE: DNA
<213> ORGANISM: Artificial Sequence
<220> FEATURE:
<223> OTHER INFORMATION: Primer

<400> SEQUENCE: 95
gatatggcca ttcaggctta atacgactca ctataaccaa acagagaatc gtgag    55

<210> SEQ ID NO 96
<211> LENGTH: 35
<212> TYPE: DNA
<213> ORGANISM: Artificial Sequence
<220> FEATURE:

```
<223> OTHER INFORMATION: Primer

<400> SEQUENCE: 96
gcgtacgtct agactggtgt ccctgttgat accgg                                35

<210> SEQ ID NO 97
<211> LENGTH: 33
<212> TYPE: DNA
<213> ORGANISM: Artificial Sequence
<220> FEATURE:
<223> OTHER INFORMATION: Primer

<400> SEQUENCE: 97
gctctagacg tacgaccctg ccctgaaccg acg                                  33

<210> SEQ ID NO 98
<211> LENGTH: 30
<212> TYPE: DNA
<213> ORGANISM: Artificial Sequence
<220> FEATURE:
<223> OTHER INFORMATION: Primer

<400> SEQUENCE: 98
gagcaatcga agtcgtacgg gtagaaggtg                                      30

<210> SEQ ID NO 99
<211> LENGTH: 27
<212> TYPE: DNA
<213> ORGANISM: Artificial Sequence
<220> FEATURE:
<223> OTHER INFORMATION: Primer

<400> SEQUENCE: 99
gtgtgaattc cgagtgcgag cccgaag                                         27

<210> SEQ ID NO 100
<211> LENGTH: 30
<212> TYPE: DNA
<213> ORGANISM: Artificial Sequence
<220> FEATURE:
<223> OTHER INFORMATION: Primer

<400> SEQUENCE: 100
ttgcatgcct gcaggtcagt accccagtc                                       30

<210> SEQ ID NO 101
<211> LENGTH: 32
<212> TYPE: DNA
<213> ORGANISM: Artificial Sequence
<220> FEATURE:
<223> OTHER INFORMATION: Primer

<400> SEQUENCE: 101
gcagtctaga ttagccattc actgcaaggc gc                                   32

<210> SEQ ID NO 102
<211> LENGTH: 31
<212> TYPE: DNA
<213> ORGANISM: Artificial Sequence
<220> FEATURE:
<223> OTHER INFORMATION: Primer

<400> SEQUENCE: 102
gggtgctagc ggagtgcccc aattgtgcca a                                    31
```

<210> SEQ ID NO 103
<211> LENGTH: 32
<212> TYPE: DNA
<213> ORGANISM: Artificial Sequence
<220> FEATURE:
<223> OTHER INFORMATION: Primer

<400> SEQUENCE: 103
tctccccggg gcagcttatt tcttaaaagg at                           32

<210> SEQ ID NO 104
<211> LENGTH: 32
<212> TYPE: DNA
<213> ORGANISM: Artificial Sequence
<220> FEATURE:
<223> OTHER INFORMATION: Primer

<400> SEQUENCE: 104
cgagcccggg ccggcattcg gtttgattct tg                           32

<210> SEQ ID NO 105
<211> LENGTH: 43
<212> TYPE: DNA
<213> ORGANISM: Artificial Sequence
<220> FEATURE:
<223> OTHER INFORMATION: Primer

<400> SEQUENCE: 105
caatggaatt caaggcaaaa cagctcaagg taaataatac ggg               43

<210> SEQ ID NO 106
<211> LENGTH: 32
<212> TYPE: DNA
<213> ORGANISM: Artificial Sequence
<220> FEATURE:
<223> OTHER INFORMATION: Primer

<400> SEQUENCE: 106
gtgaatctag aatgccggat ccgtacgaat gc                           32

<210> SEQ ID NO 107
<211> LENGTH: 36
<212> TYPE: DNA
<213> ORGANISM: Artificial Sequence
<220> FEATURE:
<223> OTHER INFORMATION: Primer

<400> SEQUENCE: 107
aaagcgccgc tgtctcctcc ctccagatgt agtcac                       36

<210> SEQ ID NO 108
<211> LENGTH: 37
<212> TYPE: DNA
<213> ORGANISM: Artificial Sequence
<220> FEATURE:
<223> OTHER INFORMATION: Primer

<400> SEQUENCE: 108
ggaggagaca gcggcgcttt ataggcgcca ttattgg                      37

<210> SEQ ID NO 109
<211> LENGTH: 31
<212> TYPE: DNA
<213> ORGANISM: Artificial Sequence
<220> FEATURE:
<223> OTHER INFORMATION: Primer

```
<400> SEQUENCE: 109
ctctgtcgac acagactacc agaactttca c                              31

<210> SEQ ID NO 110
<211> LENGTH: 31
<212> TYPE: DNA
<213> ORGANISM: Artificial Sequence
<220> FEATURE:
<223> OTHER INFORMATION: Primer

<400> SEQUENCE: 110
gggggaattc cccattcaat gaagggtcta c                              31

<210> SEQ ID NO 111
<211> LENGTH: 32
<212> TYPE: DNA
<213> ORGANISM: Artificial Sequence
<220> FEATURE:
<223> OTHER INFORMATION: Primer

<400> SEQUENCE: 111
gatccccggg tcttaaacca ggcttcgcaa tg                             32

<210> SEQ ID NO 112
<211> LENGTH: 31
<212> TYPE: DNA
<213> ORGANISM: Artificial Sequence
<220> FEATURE:
<223> OTHER INFORMATION: Primer

<400> SEQUENCE: 112
gggggaattc tggtagggtg gggaaggtag c                              31

<210> SEQ ID NO 113
<211> LENGTH: 32
<212> TYPE: DNA
<213> ORGANISM: Artificial Sequence
<220> FEATURE:
<223> OTHER INFORMATION: Primer

<400> SEQUENCE: 113
attgcccggg gggtaactaa tcaggatctc ag                             32

<210> SEQ ID NO 114
<211> LENGTH: 30
<212> TYPE: DNA
<213> ORGANISM: Artificial Sequence
<220> FEATURE:
<223> OTHER INFORMATION: Primer

<400> SEQUENCE: 114
gtaggaattc aagagaggcc gcccctcaat                                30

<210> SEQ ID NO 115
<211> LENGTH: 24
<212> TYPE: DNA
<213> ORGANISM: Artificial Sequence
<220> FEATURE:
<223> OTHER INFORMATION: Primer

<400> SEQUENCE: 115
aatgagttct ttgcctatcc cccc                                      24

<210> SEQ ID NO 116
<211> LENGTH: 45
```

```
<212> TYPE: DNA
<213> ORGANISM: Artificial Sequence
<220> FEATURE:
<223> OTHER INFORMATION: Primer

<400> SEQUENCE: 116 gggggatag gcaaagaact cattcaagga catgcatctg caggc        45

<210> SEQ ID NO 117
<211> LENGTH: 55
<212> TYPE: DNA
<213> ORGANISM: Artificial Sequence
<220> FEATURE:
<223> OTHER INFORMATION: Primer

<400> SEQUENCE: 117 gggggatag gcaaagaact cattgtagat gatgcatctg caggcctaaa tttcc        55

<210> SEQ ID NO 118
<211> LENGTH: 25
<212> TYPE: DNA
<213> ORGANISM: Artificial Sequence
<220> FEATURE:
<223> OTHER INFORMATION: Primer

<400> SEQUENCE: 118
atctacaatg agttctttgc ctatc        25

<210> SEQ ID NO 119
<211> LENGTH: 55
<212> TYPE: DNA
<213> ORGANISM: Artificial Sequence
<220> FEATURE:
<223> OTHER INFORMATION: Primer

<400> SEQUENCE: 119 gggggatag gcaaagaact cattgtagat gatgcatctg caggcctaaa tttcc        55

<210> SEQ ID NO 120
<211> LENGTH: 28
<212> TYPE: DNA
<213> ORGANISM: Artificial Sequence
<220> FEATURE:
<223> OTHER INFORMATION: oligonucleotide

<400> SEQUENCE: 120
ggccgcatat tctagagtta acgactta        28

<210> SEQ ID NO 121
<211> LENGTH: 28
<212> TYPE: DNA
<213> ORGANISM: Artificial Sequence
<220> FEATURE:
<223> OTHER INFORMATION: oligonucleotide

<400> SEQUENCE: 121
ctagtaagtc gttaactcta gaatatgc        28

<210> SEQ ID NO 122
<211> LENGTH: 24
<212> TYPE: DNA
<213> ORGANISM: Artificial Sequence
<220> FEATURE:
<223> OTHER INFORMATION: oligonucleotide

<400> SEQUENCE: 122
```

```
ggccgcatat tctagagtta acga                                      24

<210> SEQ ID NO 123
<211> LENGTH: 24
<212> TYPE: DNA
<213> ORGANISM: Artificial Sequence
<220> FEATURE:
<223> OTHER INFORMATION: oligonucleotide

<400> SEQUENCE: 123
ctagtcgtta actctagaat atgc                                      24

<210> SEQ ID NO 124
<211> LENGTH: 15
<212> TYPE: DNA
<213> ORGANISM: Artificial Sequence
<220> FEATURE:
<223> OTHER INFORMATION: Linker

<400> SEQUENCE: 124
ctagccgagc gctcg                                                15

<210> SEQ ID NO 125
<211> LENGTH: 15
<212> TYPE: DNA
<213> ORGANISM: Artificial Sequence
<220> FEATURE:
<223> OTHER INFORMATION: Linker

<400> SEQUENCE: 125
ctagcgagcw gctcg                                                15

<210> SEQ ID NO 126
<211> LENGTH: 9
<212> TYPE: PRT
<213> ORGANISM: Newcastle disease virus

<400> SEQUENCE: 126

Pro Asp Glu Gln Asp Tyr Gln Ile Arg
1               5

<210> SEQ ID NO 127
<211> LENGTH: 9
<212> TYPE: PRT
<213> ORGANISM: APMV-2

<400> SEQUENCE: 127

Asn Arg Thr Asp Ile Gln Gln Thr Ile
1               5

<210> SEQ ID NO 128
<211> LENGTH: 9
<212> TYPE: PRT
<213> ORGANISM: APMV-4

<400> SEQUENCE: 128

Pro Asp Pro Leu Gln Asp Gln Ile Leu
1               5

<210> SEQ ID NO 129
<211> LENGTH: 30
<212> TYPE: DNA
<213> ORGANISM: Artificial Sequence
<220> FEATURE:
<223> OTHER INFORMATION: Primer
```

```
<400> SEQUENCE: 129
gtagacgcgt aagagaggcc gccctcaat                                    30

<210> SEQ ID NO 130
<211> LENGTH: 57
<212> TYPE: DNA
<213> ORGANISM: Artificial Sequence
<220> FEATURE:
<223> OTHER INFORMATION: Primer

<400> SEQUENCE: 130
gatagtttgc tgtatatcag tccgattgca tgtgtcattg tatcgcttgt atatcac     57

<210> SEQ ID NO 131
<211> LENGTH: 57
<212> TYPE: DNA
<213> ORGANISM: Artificial Sequence
<220> FEATURE:
<223> OTHER INFORMATION: Primer

<400> SEQUENCE: 131
aatcggactg atatacagca aactatcatg gccaagtctt cgtataagcc tggagcc     57

<210> SEQ ID NO 132
<211> LENGTH: 15
<212> TYPE: RNA
<213> ORGANISM: Newcastle disease virus

<400> SEQUENCE: 132
ugguuugucu cuuag                                                   15

<210> SEQ ID NO 133
<211> LENGTH: 15
<212> TYPE: RNA
<213> ORGANISM: Newcastle disease virus

<400> SEQUENCE: 133
uuuagaaaca aacca                                                   15

<210> SEQ ID NO 134
<211> LENGTH: 15186
<212> TYPE: DNA
<213> ORGANISM: Newcastle disease virus LaSota

<400> SEQUENCE: 134
accaaacaga gaatccgtga gttacgataa aaggcgaagg agcaattgaa gtcgcacggg   60
tagaaggtgt gaatctcgag tgcgagcccg aagcacaaac tcgagaaagc cttctgccaa  120
catgtcttcc gtatttgatg agtacgaaca gctcctcgcg gctcagactc gccccaatgg  180
agctcatgga ggggagaaa aagggagtac cttaaaagta gacgtcccgg tattcactct  240
taacagtgat gacccagaag atagatggag ctttgtggta ttctgcctcc ggattgctgt  300
tagcgaagat gccaacaaac cactcaggca aggtgctctc atatctcttt tatgctccca  360
ctcacaggta atgaggaacc atgttgccat tgcagggaaa cagaatgaag ccacattggc  420
cgtgcttgag attgatggct tgccaacgc cacgccccag ttcaacaata ggagtggagt  480
gtctgaagag agagcacaga gatttgcgat gatagcagga tctctccctc gggcatgcag  540
caacggaacc ccgttcgtca cagccggggc agaagatgat gcaccagaag acatcaccga  600
taccctggag aggatcctct ctatccaggc tcaagtatgg gtcacagtag caaaagccat  660
gactgcgtat gagactgcag atgagtcgga acaaggcga atcaataagt atatgcagca  720
```

```
aggcagggtc caaaagaaat acatcctcta ccccgtatgc aggagcacaa tccaactcac    780
gatcagacag tctcttgcag tccgcatctt tttggttagc gagctcaaga gaggccgcaa    840
cacggcaggt ggtacctcta cttattataa cctggtaggg gacgtagact catacatcag    900
gaataccggg cttactgcat tcttcttgac actcaagtac ggaatcaaca ccaagacatc    960
agcccttgca cttagtagcc tctcaggcga catccagaag atgaagcagc tcatgcgttt   1020 gtatcgatg aaaggagata atgcgccgta catgacatta cttggtgata gtgaccagat    1080
gagctttgcg cctgccgagt atgcacaact ttactccttt gccatgggta tggcatcagt   1140
cctagataaa ggtactggga ataccaatt tgccagggac tttatgagca catcattctg    1200
gagacttgga gtagagtacg ctcaggctca gggaagtagc attaacgagg atatggctgc   1260
cgagctaaag ctaaccccag cagcaatgaa gggcctggca gctgctgccc aacgggtctc   1320
cgacgatacc agcagcatat acatgcctac tcaacaagtc ggagtcctca ctgggcttag   1380 cgagggggg tcccaagctc tacaaggcgg atcgaataga tcgcaagggc aaccagaagc    1440
cggggatggg gagacccaat tcctggatct gatgagagcg gtagcaaata gcatgaggga   1500
ggcgccaaac tctgcacagg gcactcccca atcggggcct cccccaactc ctgggccatc   1560
ccaagataac gacaccgact gggggtattg atggacaaaa cccagcctgc ttccacaaaa   1620
acatcccaat gccctcaccc gtagtcgacc cctcgatttg cggctctata tgaccacacc   1680
ctcaaacaaa catccccctc tttcctccct cccctgctg tacaactccg cacgccctag    1740
ataccacagg cacaatgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccaccttac agatgcagag atcgacgagc    1920
tatttgagac aagtggaact gtcattgaca acataattac agcccagggt aaaccagcag   1980
agactgttgg aaggagtgca atcccacaag gcaagaccaa ggtgctgagc gcagcatggg   2040
agaagcatgg gagcatccag ccaccggcca gtcaagacaa cccgatcga caggacagat    2100 ctgacaaaca accatccaca cccgagcaaa cgaccccgca tgacagcccg ccggccacat   2160
ccgccgacca gccccccacc caggccacag acgaagccgt cgacacacag ttcaggaccg   2220
gagcaagcaa ctctctgctg ttgatgcttg acaagctcag caataaatcg tccaatgcta   2280
aaaagggccc atggtcgagc ccccaagagg ggaatcacca acgtccgact caacagcagg   2340
ggagtcaacc cagtcgcgga aacagtcagg aaagaccgca gaaccaagtc aaggccgccc   2400
ctggaaacca gggcacagac gtgaacacag catatcatgg acaatgggag gagtcacaac   2460
tatcagctgg tgcaaccct catgctctcc gatcaaggca gagccaagac aatacccttg    2520
tatctgcgga tcatgtccag ccacctgtag actttgtgca agcgatgatg tctatgatgg   2580
aggcgatatc acagagagta agtaaggttg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acggcagtt gcccgatctc acccggtttt agtttcaggc cctggagacc    2820
cctctcccta tgtgacacaa ggaggcgaaa tggcacttaa taaactttcg caaccagtgc   2880
cacatccatc tgaattgatt aaacccgcca ctgcatgcgg gcctgatata ggagtggaaa   2940
aggacactgt ccgtgcattg atcatgtcac gcccaatgca cccgagttct tcagccaagc   3000
tcctaagcaa gttagatgca gccgggtcga tcgaggaaat caggaaaatc aagcgccttg   3060
```

-continued

```
ctctaaatgg ctaattacta ctgccacacg tagcgggtcc ctgtccactc ggcatcacac    3120
ggaatctgca ccgagttccc ccccgcagac ccaaggtcca actctccaag cggcaatcct    3180
ctctcgcttc ctcagcccca ctgaatggtc gcgtaaccgt aattaatcta gctacattta    3240
agattaagaa aaaatacggg tagaattgga gtgccccaat tgtgccaaga tggactcatc    3300
taggacaatt gggctgtact ttgattctgc ccattcttct agcaacctgt tagcatttcc    3360
gatcgtccta caaggcacag gagatgggaa gaagcaaatc gccccgcaat ataggatcca    3420
gcgccttgac ttgtggactg atagtaagga ggactcagta ttcatcacca cctatggatt    3480
catctttcaa gttgggaatg aagaagccac tgtcggcatg atcgatgata acccaagcg     3540 cgagttactt tccgctgcga tgctctgcct aggaagcgtc ccaaataccg agaccttat     3600 tgagctggca agggcctgtc tcactatgat agtcacatgc aagaagagtg caactaatac    3660
tgagagaatg gtttctcag tagtgcaggc accccaagtg ctgcaaagct gtagggttgt     3720
ggcaaacaaa tactcatcag tgaatgcagt caagcacgtg aaagcgccag agaagattcc    3780
cgggagtgga accctagaat acaaggtgaa ctttgtctcc ttgactgtgg taccgaagaa    3840
ggatgtctac aagatcccag ctgcagtatt gaaggtttct ggctcgagtc tgtacaatct    3900
tgcgctcaat gtcactatta atgtggaggt agacccgagg agtcctttgg ttaaatcttt    3960
gtctaagtct gacagcggat actatgctaa cctcttcttg catattggac ttatgaccac    4020
cgtagatagg aaggggaaga agtgacatt tgacaagctg gaaaagaaaa taggagcct     4080 tgatctatct gtcgggctca gtgatgtgct cgggccttcc gtgttggtaa aagcaagagg    4140
tgcacggact aagcttttgg caccttttctt ctctagcagt gggacagcct gctatcccat   4200
agcaaatgct tctcctcagg tggccaagat actctgagt caaaccgcgt gcctgcggag    4260
cgttaaaatc attatccaag caggtaccca acgcgctgtc gcagtgaccg ccgaccacga    4320
ggttacctct actaagctgg agaagggca cacccttgcc aaatacaatc cttttaagaa     4380
ataagctgcg tctctgagat tgcgctccgc ccactcaccc agatcatcat gacacaaaaa    4440
actaatctgt cttgattatt tacagttagt ttacctgtct atcaagttag aaaaaacacg    4500
ggtagaagat tctggatccc ggttggcgcc ctccaggtgc aagatgggct ccagaccttc    4560
taccaagaac ccagcaccta tgatgctgac tatccgggtt gcgctggtac tgagttgcat    4620
ctgtccggca aactccattg atggcaggcc tcttgcagct gcaggaattg tggttacagg    4680
agacaaagcc gtcaacatat acacctcatc ccagacagga tcaatcatag ttaagctcct    4740
cccgaatctg cccaaggata aggaggcatg tgcgaaagcc ccttggatg catacaacag     4800 gacattgacc acttgctca cccccttgg tgactctatc cgtaggatac aagagtctgt      4860
gactacatct ggagggggga gacagggcg ccttataggc gccattattg gcggtgtggc     4920 tcttgggtt gcaactgccg cacaaataac agcggccgca gctctgatac aagccaaaca     4980
aaatgctgcc aacatcctcc gacttaaaga gagcattgcc gcaaccaatg aggctgtgca    5040
tgaggtcact gacggattat cgcaactagc agtggcagtt gggaagatgc agcagtttgt    5100
taatgaccaa tttaataaaa cagctcagga attagactgc atcaaaattg cacagcaagt    5160
tggtgtagag ctcaacctgt acctaaccga attgactaca gtattcggac cacaaatcac    5220
ttcacctgct ttaaacaagc tgactattca ggcactttac aatctagctg gtggaaatat    5280
ggattactta ttgactaagt taggtgtagg gaacaatcaa ctcagctcat taatcggtag    5340
cggcttaatc accggtaacc ctattctata cgactcacag actcaactct gggtatacca    5400
ggtaactcta ccttcagtcg ggaacctaaa taatatgcgt gccacctact tggaaacctt    5460
```

```
atccgtaagc acaaccaggg gatttgcctc ggcacttgtc cccaaagtgg tgacacaggt    5520
cggttctgtg atagaagaac ttgacacctc atactgtata gaaactgact tagatttata    5580
ttgtacaaga atagtaacgt tccctatgtc ccctggtatt tattcctgct tgagcggcaa    5640
tacgtcggcc tgtatgtact caaagaccga aggcgcactt actacaccat acatgactat    5700
caaaggttca gtcatcgcca actgcaagat gacaacatgt agatgtgtaa accccccggg    5760
tatcatatcg caaaactatg gagaagccgt gtctctaata gataaacaat catgcaatgt    5820
tttatcctta ggcgggataa ctttaaggct cagtggggaa ttcgatgtaa cttatcagaa    5880
gaatatctca atacaagatt ctcaagtaat aataacaggc aatcttgata tctcaactga    5940
gcttgggaat gtcaacaact cgatcagtaa tgctttgaat aagttagagg aaagcaacag    6000
aaaactagac aaagtcaatg tcaaactgac tagcacatct gctctcatta cctatatcgt    6060
tttgactatc atatctcttg tttttggtat acttagcctg attctagcat gctacctaat    6120
gtacaagcaa aaggcgcaac aaaagacctt attatggctt gggaataata ctctagatca    6180
gatgagagcc actacaaaaa tgtgaacaca gatgaggaac gaaggtttcc ctaatagtaa    6240
tttgtgtgaa agttctggta gtctgtcagt tcagagagtt aagaaaaaac taccggttgt    6300
agatgaccaa aggacgatat acgggtagaa cggtaagaga ggccgcccct caattgcgag    6360
ccaggcttca aacctccgt tctaccgctt caccgacaac agtcctcaat catggaccgc    6420
gccgttagcc aagttgcgtt agagaatgat gaaagagagg caaaaaatac atggcgcttg    6480
atattccgga ttgcaatctt attcttaaca gtagtgacct tggctatatc tgtagcctcc    6540
cttttatata gcatgggggc tagcacacct agcgatcttg taggcatacc gactaggatt    6600
tccagggcag aagaaaagat tacatctaca cttggttcca atcaagatgt agtagatagg    6660
atatataagc aagtggccct tgagtctccg ttggcattgt taaatactga gaccacaatt    6720
atgaacgcaa taacatctct ctcttatcag attaatggag ctgcaaacaa cagtgggtgg    6780
ggggcaccta tccatgaccc agattatata ggggggatag gcaaagaact cattgtagat    6840
gatgctagtg atgtcacatc attctatccc tctgcatttc aagaacatct gaattttatc    6900
ccggcgccta ctacaggatc aggttgcact cgaatacccct catttgacat gagtgctacc    6960
cattactgct acacccataa tgtaatattg tctggatgca gagatcactc acattcatat    7020
cagtatttag cacttggtgt gctccggaca tctgcaacag ggagggtatt ctttctact    7080 ctgcgttcca tcaacctgga cgacacccaa aatcggaagt cttgcagtgt gagtgcaact    7140
cccctgggtt gtgatatgct gtgctcgaaa gtcacggaga cagaggaaga agattataac    7200
tcagctgtcc ctacgcggat ggtacatggg aggttagggt tcgacggcca gtaccacgaa    7260
aaggacctag atgtcacaac attattcggg gactgggtgg ccaactaccc aggagtaggg    7320
ggtggatctt ttattgacag ccgcgtatgg ttctcagtct acggagggtt aaaacccaat    7380
tcacccagtg acactgtaca ggaagggaaa tatgtgatat acaagcgata caatgacaca    7440
tgcccagatg agcaagacta ccagattcga atggccaagt cttcgtataa gcctggacgg    7500
tttggtggga acgcataca gcaggctatc ttatctatca aggtgtcaac atccttaggc    7560
gaagacccgg tactgactgt accgcccaac acagtcacac tcatggggc cgaaggcaga    7620 attctcacag tagggacatc tcatttcttg tatcaacgag ggtcatcata cttctctccc    7680
gcgttattat atcctatgac agtcagcaac aaaacagcca ctcttcatag tccttataca    7740
ttcaatgcct tcactcggcc aggtagtatc ccttgccagg cttcagcaag atgccccaac    7800
```

-continued

| | | | | |
|---|---|---|---|---|
| tcgtgtgtta | ctggagtcta | tacagatcca | tatcccctaa | tcttctatag aaaccacacc 7860 |
| ttgcgagggg | tattcgggac | aatgcttgat | ggtgtacaag | caagacttaa ccctgcgtct 7920 |
| gcagtattcg | atagcacatc | ccgcagtcgc | attactcgag | tgagttcaag cagtaccaaa 7980 |
| gcagcataca | caacatcaac | ttgttttaaa | gtggtcaaga | ctaataagac ctattgtctc 8040 |
| agcattgctg | aaatatctaa | tactctcttc | ggagaattca | gaatcgtccc gttactagtt 8100 |
| gagatcctca | aagatgacgg | ggttagagaa | gccaggtctg | gctagttgag tcaattataa 8160 |
| aggagttgga | aagatggcat | tgtatcacct | atcttctgcg | acatcaagaa tcaaaccgaa 8220 |
| tgccggcgcg | tgctcgaatt | ccatgttgcc | agttgaccac | aatcagccag tgctcatgcg 8280 |
| atcagattaa | gccttgtcat | taatctcttg | attaagaaaa | aatgtaagtg gcaatgagat 8340 |
| acaaggcaaa | acagctcatg | gtaaataata | cgggtaggac | atggcgagct ccggtcctga 8400 |
| aagggcagag | catcgagatta | tcctaccaga | gccacacctg | tcttcaccat tggtcaagca 8460 |
| caaactactc | tattactgga | aattaactgg | gctaccgctt | cctgatgaat gtgacttcga 8520 |
| ccacctcatt | ctcagccgac | aatggaaaaa | aatacttgaa | tcggcctctc ctgtactga 8580 |
| gagaatgata | aaactcggaa | gggcagtaca | ccaaactctt | aaccacaatt ccagaataac 8640 |
| cggagtgctc | cacccaggt | gtttagaaca | actggctaat | attgaggtcc cagattcaac 8700 |
| caacaaattt | cggaagattg | agaagaagat | ccaaattcac | aacacgagat atggagaact 8760 |
| gttcacaagg | ctgtgtacgc | atatagaaa | gaaactgctg | gggtcatctt ggtctaacaa 8820 |
| tgtccccgg | tcagaggagt | tcagcagcat | tcgtacggat | ccggcattct ggtttcactc 8880 |
| aaaatggtcc | acagccaagt | ttgcatggct | ccatataaaa | cagatccaga ggcatctgat 8940 |
| ggtggcagct | aagacaaggt | ctgcggccaa | caaattggtg | atgctaaccc ataaggtagg 9000 |
| ccaagtcttt | gtcactcctg | aacttgtcgt | tgtgacgcat | acgaatgaga acaagttcac 9060 |
| atgtcttacc | caggaacttg | tattgatgta | tgcagatatg | atggagggca gagatatggt 9120 |
| caacataata | tcaaccacgg | cggtgcatct | cagaagctta | tcagagaaaa ttgatgacat 9180 |
| tttgcggtta | atagacgctc | tggcaaaaga | cttgggtaat | caagtctacg atgttgtatc 9240 |
| actaatggag | ggatttgcat | acggagctgt | ccagctactc | gagccgtcag gtacatttgc 9300 |
| aggagatttc | ttcgcattca | acctgcagga | gcttaaagac | attctaattg gcctcctccc 9360 |
| caatgatata | gcagaatccg | tgactcatgc | aatcgctact | gtattctctg gtttagaaca 9420 |
| gaatcaagca | gctgagatgt | tgtgtctgtt | gcgtctgtgg | ggtcacccac tgcttgagtc 9480 |
| ccgtattgca | gcaaaggcag | tcaggagcca | aatgtgcgca | ccgaaaatgg tagactttga 9540 |
| tatgatcctt | caggtactgt | ctttcttcaa | gggaacaatc | atcaacgggt acagaaagaa 9600 |
| gaatgcaggt | gtgtggccgc | gagtcaaagt | ggatacaata | tatgggaagg tcattgggca 9660 |
| actacatgca | gattcagcag | agatttcaca | cgatatcatg | ttgagagagt ataagagttt 9720 |
| atctgcactt | gaatttgagc | catgtataga | atatgaccct | gtcaccaacc tgagcatgtt 9780 |
| cctaaaagac | aaggcaatcg | cacacccaa | cgataattgg | cttgcctcgt ttaggcggaa 9840 |
| ccttctctcc | gaagaccaga | agaaacatgt | aaaagaagca | acttcgacta atcgcctctt 9900 |
| gatagagttt | ttagagtcaa | atgatttga | tccatataaa | gagatggaat atctgacgac 9960 |
| ccttgagtac | cttagagatg | acaatgtggc | agtatcatac | tcgctcaagg agaaggaagt 10020 |
| gaaagttaat | ggacggatct | tcgctaagct | gacaaagaag | ttaaggaact gtcaggtgat 10080 |
| ggcggaaggg | atcctagccg | atcagattgc | accttcttt | cagggaaatg gagtcattca 10140 |
| ggatagcata | tccttgacca | agagtatgct | agcgatgagt | caactgtctt ttaacagcaa 10200 |

```
taagaaacgt atcactgact gtaaagaaag agtatcttca aaccgcaatc atgatccgaa   10260
aagcaagaac cgtcggagag ttgcaacctt cataacaact gacctgcaaa agtactgtct   10320
taattggaga tatcagacaa tcaaattgtt cgctcatgcc atcaatcagt tgatgggcct   10380
acctcacttc ttcgaatgga ttcacctaag actgatggac actacgatgt tcgtaggaga   10440
ccctttcaat cctccaagtg accctactga ctgtgacctc tcaagagtcc ctaatgatga   10500
catatatatt gtcagtgcca gaggggtat cgaaggatta tgccagaagc tatggacaat    10560
gatctcaatt gctgcaatcc aacttgctgc agctagatcg cattgtcgtg ttgcctgtat   10620
ggtacagggt gataatcaag taatagcagt aacgagagag gtaagatcag acgactctcc   10680
ggagatggtg ttgacacagt tgcatcaagc cagtgataat ttcttcaagg aattaattca   10740
tgtcaatcat ttgattggcc ataatttgaa ggatcgtgaa accatcaggt cagacacatt   10800
cttcatatac agcaaacgaa tcttcaaaga tggagcaatc ctcagtcaag tcctcaaaaa   10860
ttcatctaaa ttagtgctag tgtcaggtga tctcagtgaa acaccgtaa tgtcctgtgc    10920 caacattgcc tctactgtag cacggctatg cgagaacggg cttcccaaag acttctgtta   10980
ctatttaaac tatataatga gttgtgtgca gacatacttt gactctgagt tctccatcac   11040
caacaattcg cacccgatc ttaatcagtc gtggattgag gacatctctt ttgtgcactc    11100
atatgttctg actcctgccc aattaggggg actgagtaac cttcaatact caaggctcta   11160
cactagaaat atcggtgacc cggggactac tgcttttgca gagatcaagc gactagaagc   11220
agtgggatta ctgagtccta acattatgac taatatctta actaggccgc ctgggaatgg   11280
agattgggcc agtctgtgca acgacccata ctctttcaat tttgagactg ttgcaagccc   11340
aaatattgtt cttaagaaac atacgcaaag agtcctattt gaaacttgtt caaatcccct   11400
attgtctgga gtgcacacag aggataatga ggcagaagag aaggcattgg ctgaattctt   11460
gcttaatcaa gaggtgattc atccccgcgt tgcgcatgcc atcatggagg caagctctgt   11520
aggtaggaga aagcaaattc aagggcttgt tgacacaaca aacaccgtaa ttaagattgc   11580
gcttactagg aggccattag gcatcaagag gctgatgcgg atagtcaatt attctagcat   11640
gcatgcaatg ctgtttagag acgatgtttt ttcctccagt agatccaacc accccttagt   11700
ctcttctaat atgtgttctc tgacactggc agactatgca cggaatagaa gctggtcacc   11760
tttgacggga ggcaggaaaa tactgggtgt atctaatcct gatacgatag aactcgtaga   11820
gggtgagatt cttagtgtaa gcggagggtg tacaagatgt gacagcggag atgaacaatt   11880
tacttggttc catcttccaa gcaatataga attgaccgat gacaccagca agaatcctcc   11940
gatgagggta ccatatctcg ggtcaaagac acaggagagg agagctgcct cacttgcaaa   12000
aatagctcat atgtcgccac atgtaaaggc tgccctaagg gcatcatccg tgttgatctg   12060
ggcttatggg gataatgaag taaattggac tgctgctctt acgattgcaa atctcggtg    12120 taatgtaaac ttagagtatc ttcggttact gtccccttta cccacggctg ggaatcttca   12180
acatagacta gatgatggta taactcagat gacattcacc cctgcatctc tctacaggtg   12240
tcaccttaca ttcacatatc caatgattct caaaggctgt tcactgaaga aggagtcaaa   12300
gaggggaatg tggtttacca acagagtcat gctcttgggt ttatctctaa tcgaatcgat   12360
ctttccaatg acaacaacca ggacatatga tgagatcaca ctgcacctac atagtaaatt   12420
tagttgctgt atcagagaag cacctgttgc ggttcctttc gagctacttg gggtggtacc   12480
ggaactgagg acagtgacct caaataagtt tatgtatgat cctagccctg tatcggaggg   12540
```

```
agactttgcg agacttgact tagctatctt caagagttat gagcttaatc tggagtcata   12600
tcccacgata gagctaatga acattctttc aatatccagc gggaagttga ttggccagtc   12660
tgtggtttct tatgatgaag atacctccat aaagaatgac gccataatag tgtatgacaa   12720
tacccgaaat tggatcagtg aagctcagaa ttcagatgtg gtccgcctat ttgaatatgc   12780
agcacttgaa gtgctcctcg actgttctta ccaactctat tacctgagag taagaggcct   12840
agacaatatt gtcttatata tgggtgattt atacaagaat atgccaggaa ttctactttc   12900
caacattgca gctacaatat ctcatcccgt cattcattca aggttacatg cagtgggcct   12960
ggtcaaccat gacggatcac accaacttgc agatacggat tttatcgaaa tgtctgcaaa   13020
actattagta tcttgcaccc gacgtgtgat ctccggctta tattcaggaa ataagtatga   13080
tctgctgttc ccatctgtct tagatgataa cctgaatgag aagatgcttc agctgatatc   13140
ccggttatgc tgtctgtaca cggtactctt tgctacaaca agagaaatcc cgaaaataag   13200
aggcttaact gcagaagaga atgttcaat actcactgag tatttactgt cggatgctgt   13260
gaaaccatta cttagccccg atcaagtgag ctctatcatg tctcctaaca taattacatt   13320
cccagctaat ctgtactaca tgtctcggaa gagcctcaat ttgatcaggg aaagggagga   13380
cagggatact atcctggcgt tgttgttccc ccaagagcca ttattagagt tcccttctgt   13440
gcaagatatt ggtgctcgag tgaaagatcc attcacccga caacctgcgg cattttttgca  13500 agagttagat ttgagtgctc cagcaaggta tgacgcattc acacttagtc agattcatcc   13560
tgaactcaca tctccaaatc cggaggaaga ctacttagta cgatacttgt tcagagggat   13620
agggactgca tcttcctctt ggtataaggc atctcatctc ctttctgtac ccgaggtaag   13680
atgtgcaaga cacgggaact cccttatactt agctgaaggg agcggagcca tcatgagtct   13740
tctcgaactg catgtaccac atgaaactat ctattacaat acgctctttt caaatgagat   13800 gaacccccg caacgacatt tcgggccgac cccaactcag tttttgaatt cggttgttta   13860
taggaatcta caggcggagg taacatgcaa agatggattt gtccaagagt tccgtccatt   13920
atggagagaa aatacagagg aaagtgacct gacctcagat aaagcagtgg ggtatattac   13980
atctgcagtg ccctacagat ctgtatcatt gctgcattgt gacattgaaa ttcctccagg   14040
gtccaatcaa agcttactag atcaactagc tatcaattta tctctgattg ccatgcattc   14100
tgtaagggag ggcgggtag taatcatcaa agtgttgtat gcaatgggat actactttca   14160
tctactcatg aacttgtttg ctccgtgttc cacaaaagga tatattctct ctaatggtta   14220
tgcatgtcga ggagatatgg agtgttacct ggtatttgtc atgggttacc tgggcgggcc   14280
tacatttgta catgaggtgg tgaggatggc aaaaactctg gtgcagcggc acggtacgct   14340
cttgtctaaa tcagatgaga tcacactgac caggttattc acctcacagc ggcagcgtgt   14400
gacagacatc ctatccagtc ctttaccaag attaataaag tacttgagga agaatattga   14460
cactgcgctg attgaagccg ggggacagcc cgtccgtcca ttctgtgcgg agagtctggt   14520
gagcacgcta gcgaacataa ctcagataac ccagattatc gctagtcaca ttgacacagt   14580
tatccggtct gtgatatata tggaagctga gggtgatctc gctgacacag tatttctatt   14640
taccccttac aatctctcta ctgacgggaa aaagaggaca tcacttatac agtgcacgag   14700
acagatccta gaggttacaa tactaggtct tagagtcgaa aatctcaata aaataggcga   14760
tataatcagc ctagtgctta aaggcatgat ctccatggag gaccttatcc cactaaggac   14820
atacttgaag catagtacct gccctaaata tttgaaggct gtcctaggta ttaccaaact   14880
caaagaaatg tttacagaca cttctgtatt gtacttgact cgtgctcaac aaaaattcta   14940
```

-continued

```
catgaaaact ataggcaatg cagtcaaagg atattacagt aactgtgact cttaacgaaa    15000
atcacatatt aataggctcc ttttttggcc aattgtattc ttgttgattt aatcatatta    15060
tgttagaaaa aagttgaacc ctgactcctt aggactcgaa ttcgaactca aataaatgtc    15120
ttaaaaaaag gttgcgcaca attattcttg agtgtagtct cgtcattcac caaatctttg    15180
tttggt                                                               15186
```

<210> SEQ ID NO 135
<211> LENGTH: 7
<212> TYPE: PRT
<213> ORGANISM: Newcastle disease virus LaSota

<400> SEQUENCE: 135

Gly Gly Arg Gln Gly Arg Leu
1               5

<210> SEQ ID NO 136
<211> LENGTH: 7
<212> TYPE: PRT
<213> ORGANISM: Newcastle disease virus - virulent

<400> SEQUENCE: 136

Gly Arg Arg Gln Arg Arg Phe
1               5

<210> SEQ ID NO 137
<211> LENGTH: 63
<212> TYPE: DNA
<213> ORGANISM: Newcastle disease virus

<400> SEQUENCE: 137

```
ttagaaaaaa gttgaaccct gactccttag gactcgaatt cgaactcaaa taaatgctta    60
aaa                                                                  63
```

<210> SEQ ID NO 138
<211> LENGTH: 54
<212> TYPE: DNA
<213> ORGANISM: canine distemper virus

<400> SEQUENCE: 138

```
atacgaaaaa aaacaacggt tattaataag ttatcatacc cagctttgtc tggt          54
```

<210> SEQ ID NO 139
<211> LENGTH: 51
<212> TYPE: DNA
<213> ORGANISM: Measles virus

<400> SEQUENCE: 139

```
attaaagaaa actttgaaaa tacgaagttt ctattcccag ctttgtctgg t             51
```

<210> SEQ ID NO 140
<211> LENGTH: 51
<212> TYPE: DNA
<213> ORGANISM: Rinderpest virus

<400> SEQUENCE: 140

```
actaaagaaa acttcaaaga tgtgaagttt ctatcccag ctttgtctgg t              51
```

<210> SEQ ID NO 141
<211> LENGTH: 55
<212> TYPE: DNA

-continued

<213> ORGANISM: Bovine parainfluenza virus

<400> SEQUENCE: 141
agtaagaaaa acatataata tatatatacc aaacagagtt tttctcttgt ttggt 55

<210> SEQ ID NO 142
<211> LENGTH: 55
<212> TYPE: DNA
<213> ORGANISM: Human parainfluenza virus

<400> SEQUENCE: 142
agtaagaaaa acatgtaata tatatatacc aaacagagtt cttctcttgt ttggt 55

<210> SEQ ID NO 143
<211> LENGTH: 60
<212> TYPE: DNA
<213> ORGANISM: Sendai virus

<400> SEQUENCE: 143
aaacttacaa gaagacaaga aaatttaaaa ggatacatat ctcttaaact cttgtctggt 60

<210> SEQ ID NO 144
<211> LENGTH: 60
<212> TYPE: DNA
<213> ORGANISM: Newcastle disease virus

<400> SEQUENCE: 144
aaaggttgcg cacaattatt cttgagtgta gtctcgtcat tcaccaaatc tttgtttggt 60

<210> SEQ ID NO 145
<211> LENGTH: 32
<212> TYPE: DNA
<213> ORGANISM: Human parainfluenza virus

<400> SEQUENCE: 145
tttaagaaaa acatattgat tttccccttg gt 32

<210> SEQ ID NO 146
<211> LENGTH: 35
<212> TYPE: DNA
<213> ORGANISM: Mumps virus

<400> SEQUENCE: 146
ttaagaaaaa attgatttta ctttctcccc ttggt 35

<210> SEQ ID NO 147
<211> LENGTH: 30
<212> TYPE: DNA
<213> ORGANISM: Simian virus 41

<400> SEQUENCE: 147
ttaagaaaaa atatccgttc tccccttggt 30

<210> SEQ ID NO 148
<211> LENGTH: 42
<212> TYPE: DNA
<213> ORGANISM: Simian virus 5

<400> SEQUENCE: 148
ttaagaaaaa agaagaggat taatcttggt tttccccttg gt 42